United States Patent
Jung et al.

(10) Patent No.: US 8,340,944 B2
(45) Date of Patent: *Dec. 25, 2012

(54) COMPUTATIONAL AND/OR CONTROL SYSTEMS AND METHODS RELATED TO NUTRACEUTICAL AGENT SELECTION AND DOSING

(75) Inventors: Edward K. Y. Jung, Bellevue, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Livermore, CA (US)

(73) Assignee: The Invention Science Fund I, LLC, Bellevue, WA (US)

(*) Notice: Subject to any disclaimer, the term of this patent is extended or adjusted under 35 U.S.C. 154(b) by 1498 days.

This patent is subject to a terminal disclaimer.

(21) Appl. No.: 11/515,357

(22) Filed: Sep. 1, 2006

(65) Prior Publication Data

US 2007/0214008 A1    Sep. 13, 2007

Related U.S. Application Data

(63) Continuation-in-part of application No. 11/453,571, filed on Jun. 14, 2006, and a continuation-in-part of application No. 11/486,998, filed on Jul. 14, 2006, and a continuation-in-part of application No. 11/478,341, filed on Jun. 28, 2006, and a continuation-in-part of application No. 11/478,296, filed on Jun. 28, 2006, and a continuation-in-part of application No. 11/486,973, filed on Jul. 14, 2006, and a continuation-in-part of application No. 11/474,109, filed on Jun. 23, 2006, and a continuation-in-part of application No. 11/314,945, filed on Dec. 20, 2005, and a continuation-in-part of application No. 11/291,482, filed on Nov. 30, 2005.

(51) Int. Cl.
*G06Q 40/00* (2012.01)
(52) U.S. Cl. .............................................. 703/2; 703/3
(58) Field of Classification Search ...................... 703/2
See application file for complete search history.

(56) References Cited

U.S. PATENT DOCUMENTS

| | | | |
|---|---|---|---|
| 4,009,078 | A | 2/1977 | Wilkins et al. |
| 4,257,041 | A | 3/1981 | Masucci |
| 4,436,378 | A | 3/1984 | Kirkman |
| 4,567,185 | A | 1/1986 | Sackner |
| H201 | H | 1/1987 | Yager |
| 4,729,636 | A | 3/1988 | Te Velde et al. |
| 4,807,967 | A | 2/1989 | Veenvliet et al. |
| 4,838,275 | A | 6/1989 | Lee |

(Continued)

FOREIGN PATENT DOCUMENTS

JP     61002060 A     1/1986

(Continued)

OTHER PUBLICATIONS

U.S. Appl. No. 11/637,638, Jung et al.

(Continued)

*Primary Examiner* — Valerie Lubin
*Assistant Examiner* — Reginald R Reyes

(57) ABSTRACT

The present disclosure relates to computational and/or control systems and methods related to nutraceutical agent selection and dosing.

28 Claims, 36 Drawing Sheets

U.S. PATENT DOCUMENTS

| | | | |
|---|---|---|---|
| 4,847,764 A * | 7/1989 | Halvorson | 700/231 |
| 4,857,716 A | 8/1989 | Gombrich et al. | |
| 5,006,343 A | 4/1991 | Benson et al. | |
| 5,054,493 A | 10/1991 | Cohn et al. | |
| 5,093,268 A | 3/1992 | Leventis et al. | |
| 5,284,656 A | 2/1994 | Platz et al. | |
| 5,300,302 A | 4/1994 | Tachon et al. | |
| 5,307,263 A | 4/1994 | Brown | |
| 5,354,934 A | 10/1994 | Pitt et al. | |
| 5,412,560 A | 5/1995 | Dennison | |
| 5,490,962 A | 2/1996 | Cima et al. | |
| 5,654,011 A | 8/1997 | Jackson et al. | |
| 5,672,154 A | 9/1997 | Sillén et al. | |
| 5,686,429 A | 11/1997 | Lin et al. | |
| 5,692,502 A | 12/1997 | Alpert | |
| 5,700,998 A | 12/1997 | Palti | |
| 5,704,350 A | 1/1998 | Williams, III | |
| 5,719,123 A | 2/1998 | Morley et al. | |
| 5,737,539 A | 4/1998 | Edelson et al. | |
| 5,747,349 A | 5/1998 | van den Engh et al. | |
| 5,758,095 A | 5/1998 | Albaum et al. | |
| 5,758,096 A | 5/1998 | Barsky et al. | |
| 5,765,606 A | 6/1998 | Takemasa et al. | |
| 5,770,226 A | 6/1998 | Hughes, Jr. et al. | |
| 5,780,014 A | 7/1998 | Eljamal et al. | |
| 5,807,579 A | 9/1998 | Vilkov et al. | |
| 5,820,876 A | 10/1998 | Hoffmann | |
| 5,824,494 A | 10/1998 | Feldberg | |
| 5,837,196 A | 11/1998 | Pinkel et al. | |
| 5,839,438 A | 11/1998 | Graettinger et al. | |
| 5,873,369 A | 2/1999 | Laniado et al. | |
| 5,882,931 A | 3/1999 | Petersen | |
| 5,907,291 A | 5/1999 | Chen et al. | |
| 5,940,801 A | 8/1999 | Brown | |
| 5,945,115 A | 8/1999 | Dunn et al. | |
| 5,954,640 A | 9/1999 | Szabo | |
| 5,955,269 A | 9/1999 | Ghai et al. | |
| 5,958,458 A | 9/1999 | Norling et al. | |
| 5,972,710 A | 10/1999 | Weigl et al. | |
| 5,993,783 A | 11/1999 | Eljamal et al. | |
| 5,995,938 A | 11/1999 | Whaley | |
| 6,021,202 A | 2/2000 | Anderson et al. | |
| 6,023,916 A | 2/2000 | Bouthiette | |
| 6,024,699 A | 2/2000 | Surwit et al. | |
| 6,035,230 A | 3/2000 | Kang et al. | |
| 6,087,090 A | 7/2000 | Mascarenhas | |
| 6,090,545 A | 7/2000 | Wohlstadter et al. | |
| 6,117,073 A | 9/2000 | Jones et al. | |
| 6,128,534 A * | 10/2000 | Park et al. | 607/17 |
| 6,139,494 A | 10/2000 | Cairnes | |
| 6,161,095 A * | 12/2000 | Brown | 705/2 |
| 6,169,068 B1 | 1/2001 | Levin et al. | |
| 6,188,988 B1 | 2/2001 | Barry et al. | |
| 6,194,900 B1 | 2/2001 | Freeman et al. | |
| 6,221,677 B1 | 4/2001 | Wu et al. | |
| 6,227,371 B1 | 5/2001 | Song | |
| 6,280,771 B1 | 8/2001 | Monkhouse et al. | |
| 6,287,595 B1 | 9/2001 | Loewy et al. | |
| 6,295,506 B1 | 9/2001 | Heinonen et al. | |
| 6,317,719 B1 | 11/2001 | Schrier et al. | |
| 6,335,021 B1 | 1/2002 | Cavazza | |
| 6,379,929 B1 | 4/2002 | Burns et al. | |
| 6,383,136 B1 | 5/2002 | Jordan | |
| 6,397,190 B1 | 5/2002 | Goetz | |
| 6,421,650 B1 | 7/2002 | Goetz et al. | |
| 6,451,286 B1 | 9/2002 | Modi | |
| 6,454,945 B1 | 9/2002 | Weigl et al. | |
| 6,468,805 B1 | 10/2002 | Smith | |
| 6,482,306 B1 | 11/2002 | Yager et al. | |
| 6,510,430 B1 | 1/2003 | Oberwager et al. | |
| 6,529,446 B1 | 3/2003 | de la Huerga | |
| 6,541,213 B1 | 4/2003 | Weigl et al. | |
| 6,541,478 B1 | 4/2003 | O'Malley et al. | |
| 6,565,841 B1 | 5/2003 | Niven et al. | |
| 6,565,874 B1 | 5/2003 | Dunn et al. | |
| 6,576,267 B2 | 6/2003 | Gelber et al. | |
| 6,582,987 B2 | 6/2003 | Jun et al. | |
| 6,589,169 B1 * | 7/2003 | Surwit et al. | 600/300 |
| 6,605,454 B2 | 8/2003 | Barenburg et al. | |
| 6,616,606 B1 | 9/2003 | Petersen et al. | |
| 6,630,155 B1 | 10/2003 | Chandrashekar et al. | |
| 6,656,507 B2 | 12/2003 | Petereit et al. | |
| 6,671,818 B1 | 12/2003 | Mikurak | |
| 6,695,147 B1 | 2/2004 | Yager et al. | |
| 6,699,193 B2 | 3/2004 | Crutchfield et al. | |
| 6,709,676 B2 | 3/2004 | Cho | |
| 6,709,869 B2 | 3/2004 | Mian et al. | |
| 6,759,062 B2 | 7/2004 | Gelber et al. | |
| 6,764,831 B2 | 7/2004 | Cameron, Sr. et al. | |
| 6,773,714 B2 | 8/2004 | Dunn et al. | |
| 6,773,721 B1 | 8/2004 | Wong et al. | |
| 6,787,164 B2 | 9/2004 | Gelber et al. | |
| 6,790,198 B1 | 9/2004 | White et al. | |
| 6,793,942 B2 | 9/2004 | Gelber et al. | |
| 6,794,196 B2 | 9/2004 | Fonash et al. | |
| 6,812,458 B2 | 11/2004 | Gregori et al. | |
| 6,818,435 B2 | 11/2004 | Carvalho et al. | |
| 6,838,076 B2 | 1/2005 | Patton et al. | |
| 6,841,544 B2 | 1/2005 | Gelber et al. | |
| 6,849,396 B2 | 2/2005 | Schneider | |
| 6,852,206 B2 | 2/2005 | Pawliszyn et al. | |
| 6,878,755 B2 | 4/2005 | Singh et al. | |
| 6,881,425 B2 | 4/2005 | Pushpangadan et al. | |
| 6,888,095 B2 | 5/2005 | Khan | |
| 6,921,527 B2 | 7/2005 | Platz et al. | |
| 6,946,144 B1 | 9/2005 | Jordan | |
| 6,951,545 B2 | 10/2005 | Smith et al. | |
| 6,955,873 B1 | 10/2005 | Blum | |
| 6,958,216 B2 | 10/2005 | Kelley et al. | |
| 6,962,720 B2 | 11/2005 | Haridas et al. | |
| 6,979,463 B2 | 12/2005 | Kou | |
| 6,979,471 B1 | 12/2005 | Khanuja et al. | |
| 6,979,679 B2 | 12/2005 | Marcum | |
| 6,980,958 B1 | 12/2005 | Surwit et al. | |
| 7,005,447 B2 | 2/2006 | Ahotupa et al. | |
| 7,016,752 B1 | 3/2006 | Ruben et al. | |
| 7,022,288 B1 | 4/2006 | Boss | |
| 7,029,441 B2 | 4/2006 | Dodds | |
| 7,030,989 B2 | 4/2006 | Yager et al. | |
| 7,041,317 B2 | 5/2006 | Sekiya et al. | |
| 7,041,670 B2 | 5/2006 | Boojamra et al. | |
| 7,041,840 B2 | 5/2006 | Gandhi | |
| 7,045,145 B1 | 5/2006 | Chien | |
| 7,045,159 B1 | 5/2006 | Ilic et al. | |
| 7,046,357 B2 | 5/2006 | Weinberger et al. | |
| 7,048,945 B2 | 5/2006 | Percel et al. | |
| 7,049,312 B1 | 5/2006 | Rafferty et al. | |
| 7,049,433 B2 | 5/2006 | Fan et al. | |
| 7,053,107 B2 | 5/2006 | Borchardt et al. | |
| 7,056,951 B2 | 6/2006 | Spireas | |
| 7,074,311 B1 | 7/2006 | Cunningham | |
| 7,074,583 B2 | 7/2006 | Yoshizato et al. | |
| 7,112,444 B2 | 9/2006 | Beebe et al. | |
| 7,135,616 B2 | 11/2006 | Heard et al. | |
| 7,136,820 B1 | 11/2006 | Petrus | |
| 7,151,982 B2 | 12/2006 | Liff et al. | |
| 7,169,432 B2 | 1/2007 | Tanaka et al. | |
| 7,172,897 B2 | 2/2007 | Blackburn et al. | |
| 7,193,128 B2 | 3/2007 | Copenhaver et al. | |
| 7,197,492 B2 | 3/2007 | Sullivan | |
| 7,206,605 B2 | 4/2007 | Hattori | |
| 7,215,887 B2 | 5/2007 | Ternullo et al. | |
| 7,216,343 B2 | 5/2007 | Das et al. | |
| 7,218,900 B2 | 5/2007 | Suzuki | |
| 7,227,956 B1 | 6/2007 | Onishi | |
| 7,236,595 B1 | 6/2007 | Bean et al. | |
| 7,245,894 B2 | 7/2007 | Sekiguchi et al. | |
| RE39,785 E | 8/2007 | Fuse | |
| 7,254,160 B2 | 8/2007 | Kawamoto et al. | |
| 7,257,327 B2 | 8/2007 | Small | |
| 7,260,155 B2 | 8/2007 | Stonick et al. | |
| 7,260,402 B1 | 8/2007 | Ahmed | |
| 7,260,764 B2 | 8/2007 | Chen | |
| 7,260,768 B1 | 8/2007 | Matsumoto et al. | |
| 7,280,975 B1 | 10/2007 | Donner | |
| 7,351,739 B2 | 4/2008 | Ho et al. | |
| 7,376,585 B2 | 5/2008 | Haller | |

| | | |
|---|---|---|
| 7,379,167 B2 | 5/2008 | Mawhirt et al. |
| 7,483,839 B2 | 1/2009 | Mayaud |
| 7,490,085 B2 | 2/2009 | Walker et al. |
| 7,502,666 B2 | 3/2009 | Siegel et al. |
| 7,635,594 B2 | 12/2009 | Holmes et al. |
| 2001/0003177 A1 | 6/2001 | Schena et al. |
| 2001/0022758 A1 | 9/2001 | Howard |
| 2001/0037220 A1 | 11/2001 | Merry et al. |
| 2002/0004749 A1 | 1/2002 | Froseth et al. |
| 2002/0016719 A1 | 2/2002 | Nemeth et al. |
| 2002/0019784 A1 | 2/2002 | Ritz |
| 2002/0027164 A1 | 3/2002 | Mault et al. |
| 2002/0032580 A1 | 3/2002 | Hopkins |
| 2002/0032582 A1 | 3/2002 | Feeney, Jr. et al. |
| 2002/0032620 A1 | 3/2002 | Benz et al. |
| 2002/0046948 A1 | 4/2002 | Chow et al. |
| 2002/0052763 A1 | 5/2002 | Jung Richardson |
| 2002/0055856 A1 | 5/2002 | Adams |
| 2002/0059030 A1 | 5/2002 | Otworth et al. |
| 2002/0065682 A1 | 5/2002 | Goldenberg |
| 2002/0070226 A1 | 6/2002 | Liff et al. |
| 2002/0077850 A1 | 6/2002 | McMenimen et al. |
| 2002/0091991 A1 | 7/2002 | Castro |
| 2002/0095238 A1 | 7/2002 | Ahlin et al. |
| 2002/0100762 A1 | 8/2002 | Liff et al. |
| 2002/0106429 A1 | 8/2002 | Mudar et al. |
| 2002/0128259 A1 | 9/2002 | Ghazzi et al. |
| 2002/0143434 A1 | 10/2002 | Greeven et al. |
| 2002/0147317 A1 | 10/2002 | Bentsen et al. |
| 2002/0156651 A1 | 10/2002 | Florio et al. |
| 2002/0156683 A1 | 10/2002 | Stoutenburg et al. |
| 2002/0173875 A1 | 11/2002 | Wallace et al. |
| 2002/0177763 A1 | 11/2002 | Burns et al. |
| 2002/0192310 A1 | 12/2002 | Bland et al. |
| 2002/0194226 A1 | 12/2002 | Sheth et al. |
| 2002/0194502 A1 | 12/2002 | Sheth et al. |
| 2003/0005445 A1 | 1/2003 | Schein et al. |
| 2003/0019165 A1 | 1/2003 | Gallant et al. |
| 2003/0028399 A1 | 2/2003 | Davis et al. |
| 2003/0032868 A1 | 2/2003 | Graskov et al. |
| 2003/0036683 A1 | 2/2003 | Kehr et al. |
| 2003/0055531 A1 | 3/2003 | Liff et al. |
| 2003/0061123 A1 | 3/2003 | McMenimen et al. |
| 2003/0065537 A1 | 4/2003 | Evans |
| 2003/0069757 A1 | 4/2003 | Greenberg |
| 2003/0073931 A1 | 4/2003 | Boecker et al. |
| 2003/0074218 A1 | 4/2003 | Liff et al. |
| 2003/0083685 A1 | 5/2003 | Freeman et al. |
| 2003/0088333 A1 | 5/2003 | Liff et al. |
| 2003/0092039 A1 | 5/2003 | Olson-Munoz et al. |
| 2003/0105552 A1 | 6/2003 | Lunak et al. |
| 2003/0121929 A1 | 7/2003 | Liff et al. |
| 2003/0125837 A1 | 7/2003 | Walace et al. |
| 2003/0135388 A1 | 7/2003 | Martucci et al. |
| 2003/0139655 A1 | 7/2003 | Dodds |
| 2003/0156724 A1 | 8/2003 | Mariano et al. |
| 2003/0158756 A1 | 8/2003 | Abramson |
| 2003/0171950 A1 | 9/2003 | Kilgannon et al. |
| 2003/0189058 A1 | 10/2003 | Liff et al. |
| 2003/0191670 A1 | 10/2003 | Hatcher et al. |
| 2003/0193185 A1 | 10/2003 | Valley et al. |
| 2003/0204412 A1 | 10/2003 | Brier |
| 2003/0207270 A1 | 11/2003 | Kung et al. |
| 2003/0214129 A1 | 11/2003 | Adler |
| 2003/0216831 A1 | 11/2003 | Hart et al. |
| 2003/0219812 A1 | 11/2003 | Quay et al. |
| 2003/0220848 A1 | 11/2003 | Behrendt |
| 2003/0229455 A1 | 12/2003 | Bevilacqua et al. |
| 2003/0233250 A1 | 12/2003 | Joffe et al. |
| 2004/0032330 A1 | 2/2004 | Hoffman |
| 2004/0033553 A1 | 2/2004 | Littarru et al. |
| 2004/0053290 A1 | 3/2004 | Terbrueggen et al. |
| 2004/0064342 A1 | 4/2004 | Browne et al. |
| 2004/0075272 A1 | 4/2004 | Kaufman |
| 2004/0078236 A1 | 4/2004 | Stoodley et al. |
| 2004/0081023 A1 | 4/2004 | Ho |
| 2004/0086872 A1 | 5/2004 | Childers et al. |
| 2004/0107022 A1 | 6/2004 | Gomez |
| 2004/0111298 A1 | 6/2004 | Schoenberg |
| 2004/0121767 A1 | 6/2004 | Simpson et al. |
| 2004/0122707 A1 | 6/2004 | Sabol et al. |
| 2004/0122790 A1 | 6/2004 | Walker et al. |
| 2004/0133705 A1 | 7/2004 | Broussard et al. |
| 2004/0138921 A1 | 7/2004 | Broussard et al. |
| 2004/0138926 A1 | 7/2004 | Ishikawa et al. |
| 2004/0143403 A1 | 7/2004 | Brandon et al. |
| 2004/0151629 A1 | 8/2004 | Pease et al. |
| 2004/0154688 A1 | 8/2004 | Geltser et al. |
| 2004/0158507 A1 | 8/2004 | Meek, Jr. et al. |
| 2004/0176984 A1 | 9/2004 | White et al. |
| 2004/0188523 A1 | 9/2004 | Lunak et al. |
| 2004/0188524 A1 | 9/2004 | Lunak et al. |
| 2004/0193316 A1 | 9/2004 | Lunak et al. |
| 2004/0210341 A1 | 10/2004 | Wallace et al. |
| 2004/0215486 A1 | 10/2004 | Braverman |
| 2004/0220498 A1 | 11/2004 | Li et al. |
| 2004/0224916 A1 | 11/2004 | Dahl et al. |
| 2004/0225203 A1 | 11/2004 | Jemison et al. |
| 2004/0243437 A1 | 12/2004 | Grace et al. |
| 2004/0243441 A1 | 12/2004 | Bocionek et al. |
| 2005/0010416 A1 | 1/2005 | Anderson et al. |
| 2005/0013863 A1 | 1/2005 | Lim et al. |
| 2005/0021413 A1 | 1/2005 | Berry et al. |
| 2005/0033606 A1 | 2/2005 | Miller |
| 2005/0038558 A1 | 2/2005 | Keene |
| 2005/0053650 A1 | 3/2005 | Chalmers |
| 2005/0060188 A1 | 3/2005 | Valley |
| 2005/0062238 A1 | 3/2005 | Broadfield et al. |
| 2005/0065645 A1 | 3/2005 | Liff et al. |
| 2005/0101841 A9 | 5/2005 | Kaylor et al. |
| 2005/0102159 A1 | 5/2005 | Mondshine |
| 2005/0110268 A1 | 5/2005 | Schone |
| 2005/0118202 A1 | 6/2005 | Yamashita et al. |
| 2005/0147667 A1 | 7/2005 | Rines |
| 2005/0158401 A1 | 7/2005 | Morris |
| 2005/0192487 A1 | 9/2005 | Cosentino et al. |
| 2005/0216313 A1 | 9/2005 | Claud et al. |
| 2005/0216390 A1 | 9/2005 | Snider et al. |
| 2005/0218152 A1 | 10/2005 | Simon |
| 2005/0240305 A1 | 10/2005 | Bogash et al. |
| 2005/0260679 A1 | 11/2005 | Kellerman et al. |
| 2005/0261255 A1 | 11/2005 | Serhan et al. |
| 2005/0267356 A1 | 12/2005 | Ramasubramanian et al. |
| 2005/0271596 A1 | 12/2005 | Friedman et al. |
| 2005/0285746 A1 | 12/2005 | Sengupta et al. |
| 2006/0015016 A1 | 1/2006 | Thornton |
| 2006/0028727 A1 | 2/2006 | Moon et al. |
| 2006/0047538 A1 | 3/2006 | Condurso et al. |
| 2006/0064250 A1 | 3/2006 | Goldstein |
| 2006/0073484 A1 | 4/2006 | Mathies et al. |
| 2006/0090765 A1 | 5/2006 | Surina |
| 2006/0097516 A1 | 5/2006 | Kozlowski et al. |
| 2006/0099310 A1 | 5/2006 | Koekkoek |
| 2006/0111944 A1 | 5/2006 | Sirmans, Jr. et al. |
| 2006/0129324 A1 | 6/2006 | Rabinoff et al. |
| 2006/0177637 A1 | 8/2006 | Kimura |
| 2006/0240150 A1 * | 10/2006 | Delaney et al. ............ 426/74 |
| 2006/0254580 A1 | 11/2006 | Chalmers et al. |
| 2006/0260679 A1 | 11/2006 | Aratani et al. |
| 2006/0264780 A1 | 11/2006 | Holmes et al. |
| 2006/0280307 A1 | 12/2006 | Ikushima et al. |
| 2007/0087048 A1 | 4/2007 | Abrams et al. |
| 2007/0136092 A1 | 6/2007 | Jung et al. |
| 2007/0161076 A1 | 7/2007 | Halden |
| 2008/0097784 A1 | 4/2008 | Miller et al. |
| 2008/0299013 A1 | 12/2008 | Trieu et al. |

FOREIGN PATENT DOCUMENTS

| | | |
|---|---|---|
| WO | WO 99/45354 | 9/1999 |
| WO | WO 99/45354 A2 | 9/1999 |
| WO | WO 99/45354 A3 | 9/1999 |
| WO | WO 00/60362 | 10/2000 |
| WO | WO 00/60362 A1 | 10/2000 |
| WO | WO 01/79529 A1 | 10/2001 |
| WO | WO 03/084395 A1 | 10/2003 |
| WO | WO 2004/061085 A3 | 7/2004 |
| WO | WO 2005/041105 A1 | 5/2005 |

| WO | WO 2005/062849 A2 | 7/2005 |
| WO | WO 2006/032044 A3 | 3/2006 |
| WO | WO 2007/061838 A2 | 5/2007 |

OTHER PUBLICATIONS

U.S. Appl. No. 11/637,616, Jung et al.
U.S. Appl. No. 11/523,809, Jung et al.
U.S. Appl. No. 11/523,766, Jung et al.
U.S. Appl. No. 11/518,540, Jung et al.
Chen, Haibin; Sholl, David S.; "Predictions of Selectivity and Flux for $CH_4/H_2$ Separations Using Single Walled Carbon Nanotubes as Membranes"; Journal of Membrane Science; Bearing dates of 2005 and 2006; pp. 152-160; vol. 269; Elsevier B.V.; located at: www.sciencedirect.com and www.elsevier.com/locate/memsci.
Demello, Andrew J.; "Microfluidics: DNA Amplification Moves on"; Nature; Bearing dates of Mar. 6, 2003 and 2003; pp. 28-29; vol. 422; Nature Publishing Group; located at: www.nature.com/nature.
Fan, Chunhai; Plaxco, Kevin W.; Heeger, Alan J.; "Electrochemical interrogation of conformational changes as a reagentless method for the sequence-specific detection of DNA"; PNAS; Bearing a date of Aug. 5, 2003; pp. 9134-9137; vol. 100, No. 16; located at: www.pnas.org/cgi/doi/10.1073/pnas.1633515100.
Gao, Huajian; Kong, Yong; "Simulation of DNA-Nanotube Interactions"; Annual Review of Materials Research.; Bearing a date of 2004; pp. 123-150 (33 total pages); vol. 34; Annual Reviews.
Gruenewald, Tara L.; Seeman, Teresa E.; Ryff, Carol D.; Karlamangla, Arun S.; Singer, Burton H.; "Combinations of biomarkers predictive of later life mortality"; PNAS; Bearing dates of Sep. 19, 2006 and 2006; pp. 14158-14163; vol. 103, No. 38; The National Academy of Sciences of the USA; located at http://www.pnas.org/cgi/doi/10.1073/pnas.0606215103.
Heller, Daniel A.; Jeng, Esther S.; Yeung, Tsun-Kwan; Martinez, Brittany M.; Moll, Anthonie E.; Gastala, Joseph B.; Strano, Michael S.; "Optical Detection of DNA Conformational Polymorphism on Single-Walled Carbon Nanotubes"; Science; Bearing a date of Jan. 27, 2006; pp. 508-511; vol. 311; located at: www.sciencemag.org.
Holt, Jason K.; Park, Hyung Gyu; Wang, Yinmin; Stadermann, Michael; Artyukhin, Alexander B.; Grigoropoulos, Costas P.; Noy, Aleksandr; Bakajin, Olgica; "Fast Mass Transport Through Sub-2Nanometer Carbon Nanotubes"; Science; Bearing a date of May 19, 2006; pp. 1034-1037; vol. 312; located at: www.sciencemag.org.
Jain, KK; "Conference Scene: Lab-on-a-Chip and Microarrays: Discovery and Development"; Pharmacogenomics; Bearing a date of 2003; pp. 123-125; vol. 4, No. 2; Ashley Publications Ltd; located at: www.pharmaco-genomics.com.
Jarvius, Jonas; DNA Tools and Microfluidic Systems for Molecular Analysis; Digital Comprehensive Summaries of Uppsala Dissertations from the Faculty of Medicine 161; Bearing a date of 2006; pp. 1-66; ISBN 91-554-6616-8; Acta Universitatis Upsaliensis Uppsala.
"Nano World: Fast Flow Through Nanotube Membranes (Update)"; Physorg.com; Bearing a date of 2006; pp. 1-2; United Press International; located at: www.physorg.com/news67262683.html.
Sambrook, Joseph; Russell, David W.; "Molecular Cloning: A Laboratory Manual"; Bearing a date of Jan. 15, 2001; 2,344 pages; 3 Edition; ISBN 0-87969-577-3; Cold Spring Harbor Laboratory Press (not provided).
Sholl, David S.; Johnson, J. Karl; "Materials Science: Making High-Flux Membranes with Carbon Nanotubes"; Science; Bearing a date of May 19, 2006; pp. 1003-1004; vol. 312; AAAS; located at: www.sciencemag.org.
Singh-Zocchi, Mukta; Dixit, Sanhita; Ivanov, Vassili; Zocchi, Giovanni; "Single-Molecule Detection of DNA Hybridization"; Bearing a date of Jun. 24, 2003; pp. 7605-7610; vol. 100, No. 13; located at: www.pnas.org/cgi/doi/10.1073/pnas.1337215100.
Wang, J.; Li, J.; Baca, AJ.; Hu, J.; Zhou, F.; Yan, W.; Pang, DW.; "Amplified Voltammetric Detection of DNA Hybridization via Oxidation of Ferrocene Caps on Gold Nanoparticle/Streptavidin Conjugates"; Anal. Chem.; Bearing a date of Aug. 1, 2003; pp. 3941-3945 (p. 1); vol. 75, No. 15; PubMED; located at: http://www.ncbi.nlm.nih.gov/entrez/query.fcgi?cmd=Retrieve&db=PubMed&list_uids.=14572067&dopt=Abstract; printed on Nov. 29, 2006.
Xiao, Yl; Lubin, Arica A.; Baker, Brian R.; Plaxco, Kevin W.; Heeger, Alan J.; "Single-Step Electronic Detection of Femtomolar DNA by Target-Induced Strand Displacement in an Electrode-Bound Duplex"; PNAS; Bearing a date of Nov. 7, 2006; pp. 16677-16680; vol. 103, No. 45; located at: www.pnas.org/cgi/doi/10.1073/pnas.0607693103.
U.S. Appl. No. 12/011,008, Jung et al.
U.S. Appl. No. 11/977,174, Jung et al.
PCT International Search Report; International App. No. PCT/US 06/47436; Jan. 30, 2008; pp. 1-2.
Evans, R. Scott, Ph.D. et al., "A Computer-Assisted Management Program for Antibiotics and Other Antiinfective Agents"; The New England Journal of Medicine; bearing a date of Jan. 22, 1998; pp. 232-238; vol. 338, No. 4; The Departments of Clinical Epidemiology (R.S.E., S.L.P., D.C.C., J.F.L., J.P.B.), Critical Care (T.P.C., L.K.W., J.F.O.,), and Medical Informatics (R.S.E.), LDS Hospital, Salt Lake City, UT.
U.S. Appl. No. 11/824,604, Jung et al.
U.S. Appl. No. 11/824,529, Jung et al.
Aihara, K; Kajimoto, O; Hirata, H; Takahashi, R; Nakamura, Y; "Effect of powdered fermented milk with Lactobacillus helveticus on subjects with high-normal blood pressure or mild hypertension"; J. Am. Coll. Nutr.; Bearing a date of Aug. 2005; pp. 257-265 (pp. 1-2); vol. 24, No. 4; PubMed; located at: http://www.ncbi.nlm.nih.gov/sites/entrez?db=pubmed&list_uids=16093403&cmd=Retrieved&indexed=google; printed on Jun. 25, 2007.
Bassaganya-Riera, J.; Hontecillas, R.; Wannemuehler, M.; "Nutrition impact of conjugated linoleic acid: A model functional food ingredient"; In Vitro Cellular and Development Biology-Plant; May 2002; pp. 241-246 (pp. 1-2); vol. 38, No. 3; Online ISSN 1475-2689; Springer; located at: http://www.ingentaconnect.com/content/klu/ivp/2002/00000038/00000003/02002295?crawler=true; printed on Jun. 25, 2007.
Blum, K; Meshkin, B; Downs, BW; "DNA based customized Nutraceutical 'gene therapy' utilizing a genoscore: a hypothesized paradigm shift of a novel approach to the diagnosis, stratification, prognosis and treatment of inflammatory processes in the human"; Med. Hypotheses; Bearing dates of 2006 and Jan. 5, 2006; pp. 1008-1018 (pp. 1-2); vol. 66, No. 5; PubMed; located at: http://www.ncbi.nlm.nih.gov/sites/entrez?db=pubmed; printed on Jun. 11, 2007.
Chen, ZP; Schell, JB; Ho, CT; Chen, KY; "Green tea epigallocatechin gallate shows a pronounced growth inhibitory effect on cancerous cells but not on their normal counterparts"; Cancer Lett.; Jul. 17, 1998; pp. 173-179 (pp. 1-2); vol. 129, No. 2; PubMed; located at: http://www.ncbi.nlm.nih.gov/sites/entrez?db=pubmed;.printed on Jun. 22, 2007.
Dumont, Yannick; D'A mours, Martin; Lebel, Marcel; Larivière, Richard; "Original Article: Supplementation with a low dose of L-arginine reduces blood pressure and endothelin-1 production in hypertensive uraemic rats"; Nephrol Dial Transplant; Bearing a date of 2001; pp. 746-754; vol. 16; European Renal Association-European Dialysis and Transplant Association.
Gosslau, A; Chen, M; Ho, CI-T; Chen, KY; "Translational Therapeutics: A methoxy derivative of resveratrol analogue selectively induced activation of the mitochondrial apoptotic pathway in transformed fibroblasts"; British Journal of Cancer; Bearing dates of 2005 and Jan. 25, 2005; pp. 513-521 (pp. 1-2); vol. 92; Online ISSN: 1532-1827; Cancer Research UK; located at: http://www.nature.com/bjc/journal/v92/n3/abs/6602300a.html; printed on Jun. 22, 2007.
Hobbs, Charlotte, A.; Sherman, Stephanie, L.; YI, Ping; Hopkins, Sarah E.; Torfs, Claudine P.; Hine, R. Jean; Pogribna, Marta; Rozen, Rima; James, S. Jill; "Polymorphisms in Genes Involved in Folate Metabolism as Maternal Risk Factors for Down Syndrome"; Am. J. Hum. Genet.; Bearing a date of 2000; pp. 623-630; vol. 67; The American Society of Human Genetics.
Hodgson, JM; Watts, GF; Playford, DA; Burke, V; Croft, KD; "Original Communication-Coenzyme $Q_{10}$ improves blood pressure and glycaemic control: a controlled trial in subjects with type 2 diabetes"; European Journal of Clinical Nutrition; Bearing a date of 2002; pp. 1137-1142; vol. 56; Nature Publishing Group; located at: www.nature.com/ejcn.

James, S. Jill; Pogribna, Marta; Pogribny, Igor P.; Melnyk, Stepan; Hine, R. Jean; Gibson, James B.; Yi, Ping; Tafoya, Dixie L.; Swenson, David H.; Wilson, Vincent L.; Gaylor, David W.; "Abnormal folate metabolism and mutation in the methylenetetrahydrofolate reductase gene may be maternal risk factors for Down syndrome"; The American Journal of Clinical Nutrition; Bearing a date of 1999; pp. 495-501; vol. 70; American Society for Clinical Nutrition; located at: www.ajcn.org; printed on Jun. 11, 2007.

Kanauchi, O; Igarashi, K; Ogata, R; Mitsuyama, K; Andoh, A; "A yeast extract high in bioactive peptides has a blood-pressure lowering effect in hypertensive model"; Curr. Med. Chem.; Bearing a date of 2005; pp. 3085-3090 (p. 1); vol. 12, No. 26; PubMed; located at: http://www.ncbi.nlm.nih.gov/sites/entrez?db=pubmed; printed on May 17, 2007.

Katan, Martijn B.; "Editorial: Health claims for functional foods"; BMJ; Bearing a date of Jan. 24, 2004; pp. 180-181 (pp. 1-3); vol. 328; BMJ Publishing Group Ltd.; located at: http://www.bmj.com/cgi/content/full/328/7433/180; printed on Jun. 11, 2007.

Khosh, Farhang; Khosh, Mehdi; "Natural Approach to Hypertension"; Alternative Medicine Review; Bearing a date of 2001; pp. 590-600; vol. 6, No. 6; Thorne Research, Inc.

Kitajka, Klára; Sinclair, Andrew J.; Weisinger, Richard S.; Weisinger, Harrison S.; Mathai, Michael; Jayasooriya, Anura P.; Halver, John E.; Puskás, László G.; "Biochemistry: Effects of dietary omega-3 polyunsaturated fatty acids on brain gene expression"; PNAS; Bearing a date of Jul. 27, 2004; pp. 10931-10936; vol. 101, No. 30; The National Academy of Sciences of the USA; located at: www.pnas.org/cgi/doi/10.1073/pnas.0402342101.

Lu, Jiebo; Ho, Chi-Tang; Ghai, Geetha; Chen, Kuang Yu; "Differential Effects of Theaflavin Monogallates on Cell Growth, Apoptosis, and Cox-2 Gene Expression in Cancerous versus Normal Cells"; Cancer Research; Bearing a date of Nov. 15, 2000; pp. 6465-6471; vol. 60.

Lu, Jiebo; Ho, Chi-Tang; Ghai, Geetha; Chen, Kuang Yu; "Resveratrol analog, 3,4,5,4,'-tetrahydroxystilbene, differentially induces pro-apoptotic p53/Bax gene expression and inhibits the growth of transformed cells but not their normal counterparts"; Carcinogenesis; Bearing a date of 2001; pp. 321-328; vol. 22, No, 2; Oxford University Press.

Lucock, Mark; "Clinical Review: Science, Medicine, and the future—Is folic acid the ultimate functional food component for disease prevention?" BMJ; Bearing a date of Jan. 24, 2004; pp. 211-214 (pp. 1-9); vol. 328; BMJ Publishing Group Ltd.; located at: http://www.bmj.com/cgi/content/full/328/7433/211; printed on Jun. 22, 2007.

Ma, Jing; Stampfer, Meir J.; Giovannucci, Edward; Artigas, Carmen; Hunter, David J.; Fuchs, Charles; Willett, Walter C.; Selhub, Jacob; Hennekens, Charles H.; Rozen, Rima; "Methylenetetrahydrofolate Reductase Polymorphism, Dietary Interactions, and Risk of Colorectal Cancer"; Cancer Research; Bearing a date of Mar. 15, 1997; pp. 1098-1102; vol. 57.

Malnick, Stephen; Goland, Sorel; "Folic acid as ultimate in disease prevention Beware of vitamin B12 deficiency"; BMJ; Bearing a date of Mar. 27, 2004; pp. 1-2; vol. 328, No. 769; BMJ Publishing Group Ltd.; located at: http://www.bmj.com/cgi/content/full/328/7442/769; printed on Jun. 25, 2007.

Mills, JL; Kirke, PN; Molloy AM; Burke, H; Conley, MR; Lee, YJ; Mayne, PD; Weir, DG; Scott, JM; "Methylenetetrahydrofolate reductase thermolabile variant and oral clefts"; Am. J. Med. Genet.; Bearing a date of Sep. 3, 1999; pp. 71-74 (p. 1); vol. 86, No. 1; PubMed; located at: http://www.ncbi.nlm.nih.gov/sites/entrez; printed on Jun. 25, 2007.

Mullan, Brian A.; Young, Ian S.; Fee, Howard; McCance, David R.; "Ascorbic Acid Reduces Blood Pressure and Arterial Stiffness in Type 2 Diabetes"; Hypertension—Journal of the American Heart Association; Bearing dates of Oct. 21, 2002 and 2002; pp. 804-809 (pp. 1-7); vol. 40; Online ISSN 1524-4563; American Heart Association, Inc.; located at: http://hyper.ahajournals.org/cgi/content/full/40/6/804; printed on May 17, 2007.

Park, YK; Kim, JSs; Kang, MH; "Concord grape juice supplementation reduces blood pressure in Korean hypertensive men: double-blind, placebo controlled intervention trial"; Biofactors; Bearing a date of 2004; pp. 145-147 (p. 1); vol. 22, Nos. 1-4; PubMed; located at: http://www.ncbi.nlm.nih.gov/sites/entrez?cmd=Retrieve&db=PubMed&dopt=Citation.&list uids=15630270; printed on May 17, 2007.

Shizuka, F; Kido, Y; Nakazawa, T; Kitajima, H; Aizawa, C; Kayamura, H; Ichijo, N; "Antihypertensive effect of gamma-amino butyric acid enriched soy products in spontaneously hypertensive rats"; Biofactors; Bearing a date of 2004; pp. 165-167 (p. 1); vol. 22, Nos. 1-4; PubMed; located at: http://www.ncbi.nlm.nih.gov/sites/entrez?cmd=Retrieve&db=PubMed&list_uids=15630275 &dopt=Abstract; printed on May 17, 2007.

Steenge, Gery R.; Verhoef, Petra; Katan, Martijn B.; "Human Nutrition and Metabolism—Betaine Supplementation Lowers Plasma Homocysteine in Healthy Men and Women"; The Journal of Nutrition; Bearing a date of 2003; pp. 1291-1295; vol. 133; American Society for Nutritional Sciences; located at: jn.nutrition.org; printed on May 17, 2007.

Subbiah, MT; "Nutrigenetics and Nutraceuticals: the next wave riding on personalized medicine"; Transl Res.; Bearing a date of Feb. 2007; pp. 55-61 (pp. 1-2); vol. 149, No. 2; PubMed; located at: http://www.ncbi.nlm.nih.gov/sites/entrez; printed on Jun. 25, 2007.

Vieira Da Costa, VA; Vianna, LM; "Effect of alpha-tocopherol supplementation on blood pressure and lipidic profile in streptozotocin-induced diabetes mellitus in spontaneously hypertensive rats"; Clin. Chim. Acta.; Bearing a date of Jan. 2005; pp. 101-104 (p. 1); vol. 351, Nos. 1-2; PubMed; located at: http://www.ncbi.nlm.nili.gov/sites/entrez; printed on May 17, 2007.

Wan, Ruiqian; Camandola, Simonetta; Mattson, Mark P.; "Dietary supplementation with 2-deoxy-d-glucose improves cardiovascular and neuroendocrine stress adaptation in rats"; Am. J. Physiol Heart Circ. Physiol; Bearing dates of Oct. 10, 2003 and Apr. 26, 2004; pp. 1-13; vol. 287; American Physiological Society; located at: http://ajpheart.physiology.org/cgi/content/full/287/3/H11186; printed on May 17, 2007.

West, SG; Likos-Krick, A; Brown, P; Mariotti, F; "Oral L-arginine improves hemodynamic responses to stress and reduces plasma homocysteine in hypercholesterolemic men"; J. Nutr.; Bearing a date of Feb. 2005; pp. 212-217 (p. 1-2); vol. 135, No. 2; PubMed; located at: http://www.ncbi.nlm.nih.gov/sites/entrez?cmd=Retrieve&db=pubmed&dopt=Abstract &list_uids=15671215; printed on Jun. 25, 2007.

Wilson, A; Platt, R; WU, Q; Leclerc, D; Christensen, B; Yang, H; Gravel, RA; Rozen, R; "A common variant in methionine synthase reductase combined with low cobalamin (vitamin B12) increases risk for spina bifida"; Mol. Genet. Metab.; Bearing a date of Aug. 1999; pp. 317-323 (p. 1); vol. 67, No. 4; PubMed; located at: http://www.ncbi.nlm.nih.gov/sites/entrez; printed on Jun. 25, 2007.

U.S. Appl. No. 11/524,084, Jung et al.
U.S. Appl. No. 11/904,016, Jung et al.
U.S. Appl. No. 11/906,112, Jung et al.
U.S. Appl. No. 11/355,517, Jung et al.
U.S. Appl. No. 11/339,316, Jung et al.
U.S. Appl. No. 11/314,949, Jung et al.
U.S. Appl. No. 11/314,764, Jung et al.
U.S. Appl. No. 11/291,532, Jung et al.
U.S. Appl. No. 11/285,753, Jung et al.
U.S. Appl. No. 11/285,500, Jung et al.
U.S. Appl. No. 11/283,548, Jung et al.
PCT International Search Report; International App. No. PCT/US 06/44664; Apr. 14, 2008; pp. 1-3.
PCT International Search Report; International App. No. PCT/ US 06/44269; Sep. 18, 2007; pp. 1-2.
Lagally, E.T. et al.; "Integrated Portable Genetic Analysis Microsystem for Pathogen/Infectious Disease Detection"; Analytical Chemistry; bearing a date of Jun. 1, 2004; pp. 3162-3170; vol. 76, No. 11; © 2004 American Chemical Society.
Leibovici, Leonard et al.; "A Causal Probabilistic Network for Optimal Treatment of Bacterial Infections"; IEEE Transactions on Knowledge and Data Engineering; bearing a date of Jul./Aug. 2000; pp. 517-528; vol. 12, No. 4; © 2000 IEEE.
PCT International Search Report; International App. No. PCT/US07/25379; May 13, 2008; 1-2.

PCT International Search Report; International App. No. PCT/US07/25417; May 14, 2008; pp. 1-3.

PCT International Search Report; International App. No. PCT/US07/25417; May 19, 2008; pp. 1-2.

PCT International Search Report; International App. No. PCT/US2007/025450; May 23, 2008; pp. 1-2.

PCT International Search Report; International App. No. PCT/US06/47835; Jul. 14, 2008; pp. 1-2.

"A 1C At-Home Test Kit-Introductory Offer (1 per customer, first time buyers Only)"; Amazon.com; bearing dates of 1996-2006; pp. 1-4; Amazon.com, Inc.; located at: http://www.amazon.com/gp/product/B0006JMPRG/ref=sr_11_1/103-2429377-9250203?ie=UTF8; printed on Jul. 10, 2006.

Abrams, Bernard; "Standing Rx packaging on its head"; Packagingdigest.com; bearing a date of Jun. 2005; pp. 1-3; located at http://www.packagingdigest.com/articles/200506/38.php; printed on Jun. 21, 2006.

Actis-Goretta, Lucas; Ottaviani, Javier I.; Fraga, Cesar G.; "Inhibition of Angiotensin Converting Enzyme Activity by Flavanol-Rich Foods"; Journal of Agricultural and Food Chemistry; bearing a date of 2006; pp. 229-234; vol. 54; American Chemical Society.

"Anemia Tests"; Home Health Testing; bearing dates of Dec. 1, 2005 and 2000; pp. 1-3; AbDiagnostics, Inc.; located at: http://www.homehealthtesting.com/anemia-tests.htm; printed on Jul. 24, 2006.

"Antioxidant Tests"; Home Health Testing; bearing dates of Dec. 1, 2005 and 2000; pp. 1-2; AbDiagnostics, Inc.; located at: http://www.homehealthtesting.com/antioxidant-tests.htm; printed on Jul. 24, 2006.

Appleton, David; Lockwood, Brian; "Building Bones with Nutraceuticals"; The Pharmaceutical Journal; bearing a date of Jul. 15, 2006; pp. 78-83; vol. 277; located at: http://www.pjonline.com/pdf/articles/pj_20060715_bones.pdf; printed on Aug. 22, 2006.

"Blood Testing and Sampling Kits"; BloodBook.com; bearing dates of Nov. 19, 2005 and 2000-2005; pp. 1-2; located at: http://www.bloodbook.com/test-kits.html; printed on Jul. 10, 2006.

"Body Balance: AntiOxidant Check"; Health HomeTest.com; bearing dates of 2003-2005; pp. 1-4; B Scientific, Inc.; located at: http://www.healthhometest.com/product_info.php?products_id=39; printed on Jul. 24, 2006.

"Body Balance: FemaleCheck / Estradiol, Progesterone & Testosterone"; Health HomeTest.com; bearing dates of 2003-2005; pp. 1-5; B Scientific, Inc.; located at: http://www.healthhometest.com/product_info.php?products_id=36; printed on Jul. 24, 2006.

"Body Balance: MaleCheck / Testosterone & DHEA"; Health HomeTest.com; bearing dates of 2003-2005; pp. 1-4; B Scientific, Inc.; located at: http://www.healthhometest.com/product_info.php?manufacturers_id=10&products_id=40; printed on Jul. 24, 2006.

"Body Balance: Mineral Check"; Health HomeTest.com; bearing dates of 2003-2005; pp. 1-8; B Scientific, Inc.; located at: http://www.healthhometest.com/product_info.php?products_id=35; printed on Jul. 24, 2006.

"Body Balance: Performance Check"; Health HomeTest.com; bearing dates of 2003-2005; pp. 1-7; B Scientific, Inc.; located at: http://www.healthhometest.com/product_info.php?products_id=82; printed on Jul. 24, 2006.

"Body Balance: Sleep Check / Melatonin"; Health HomeTest.com; bearing dates of 2003-2005; pp. 1-4; B Scientific, Inc.; located at: http://www.healthhometest.com/product_info.php?products_id=46; printed on Jul. 24, 2006.

"Body Balance: Stress Check / DHEA & Cortisol"; Health HomeTest.com; bearing dates of 2003-2005; pp. 1-6; B Scientific, Inc.; located at: http://www.healthhometest.com/product_info.php?products_id=43; printed on Jul. 24, 2006.

"Body Building Hormone Tests"; Home Health Testing; bearing dates of Dec. 1, 2005 and 2000; pp. 1-3; AbDiagnostics, Inc.; located at: http://www.homehealthtesting.com/performance-hormone-tests.htm; printed on Jul. 24, 2006.

Bridges, Andrew; "HIV/AIDS patients get $1^{st}$ once-daily pill"; Associated Press; bearing a date of 2006; pp. 1-3; Yahoo! Inc.; located at http://news.yahoo.com/s/ap/20060712/ap_on_he_me/hiv$_{13}$_one_pill; printed on Jul. 12, 2006.

"Browse by: Product Category"; Hach.com; bearing a date of 2006; pp. 1-2; Hach Company; located at: http://www.hach.com/hc/browse.exploded.product.category/PREVIOUS_BREADCRUMB_ID=/SESSIONID|BzFOVFUzTnpZME1URTBOQ1puZFdWemRFMUNTZz09QTFOVU1URQ==|; printed on Jul. 14, 2006.

Chiu, KM; Keller, ET; Crenshaw, TD; Gravenstein, S.; "Carnitine and dehydroepiandrosterone sulfate induce protein synthesis in porcine primary osteoblast-like cells"; Calcified Tissue International; bearing a date of Jun. 1999; pp. 527-533 (pp. 1-2); vol. 64, Issue 6; PubMed; located at: http://www.ncbi.nlm.nih.gov/entrez/query.fcgi?cmd=Retrieve&db=PubMed&list_uids=103410267dopt=Abstract; printed on Aug. 22, 2006.

"CLEARRX System: Body"; pp. 1-4; located at http://www.index2005.dk/Members/tenamikesy/bodyObject; printed on Jun. 21, 2006.

"Clinical Laboratory: Beckman Coulter clinical systems help to simplify and automate laboratory processes"; Beckman Coulter.com; bearing dates of 1998-2006; p. 1; Beckman Coulter, Inc.; located at: http://www.beckmancoulter.com/products/pr_clinical_lab.asp; printed on Jul. 14, 2006.

Colucci, S; Mori, G; Vaira, S; Brunetti, G; Greco, G; Mancini, L; Simone, GM; Sardelli, F; Koverech, A; Zallone, A; Grano, M; "L-carnitine and isovaleryl L-carnitine fumarate positively affect human osteoblast proliferation and differentiation in vitro"; Calcified Tissue International; bearing a date of Jun. 2005; pp. 458-465 (pp. 1-2); vol. 76, Issue 6; PubMed; located at: http://www.ncbi.nlm.nih.gov/entrez/query.fcgi?cmd=Retrieve&db=PubMed&list_uids=15906015&dopt=Abstract; printed on Aug. 22, 2006.

"Confidential Home DNA Infidelity Testing, Infidelity Test Kit"; Gtldna.com; bearing dates of Jul. 10, 2006 and 2002-2005; pp. 1-3; The Genetic Testing Laboratories, Inc.; located at: http://www.gtldna.com/infidelity.html; printed on Jul. 10, 2006.

Davidow, Julie; "Surge in home diagnostic kits provides doctor in a box"; Seattlepi.com; bearing dates of Mar. 29, 2006 and 1996-2006; pp. 1-4; Seattle Post-Intelligencer; located at: http://seattlepi.nwsource.com/health/264716_hometesting29.html; printed on Jul. 10, 2006.

"Direct to Consumer Blood Test Index"; PreventiveLabs.com; bearing a date of 2004; pp. 1-6; Preventive Services, LLC; located at: http://www.preventivelabs.com/lab_test/blood_test.cfm; printed on Jul. 10, 2006.

"Dr / 2400 Portable Spectrophotometer, 115 Vac"; Hach.com; bearing a date of 2006; p. 1; Hach Company; located at: http://www.hach.com/hc/search.product.details.invoker/PackagingCode=5940000/NewLinkLabel=DR%26frasl%3B2400+Portable+Spectrophotometer%2C+115+Vac/PREVIOUS_BREADCRUMB_ID=HC_SEARCH_KEYWORD/SESSIONID|BzFOVFUzTnpFMk56WXINU1puZFdWemRFTk9-Vdz09QTFsTk1URQ==|; printed on Jul. 14, 2006.

"DR 5000 UV-VIS Spectrophotometer (115 Vac)"; Hach.com; bearing a date of 2006; p. 1; Hach Company; located at: http://www.hach.com/hc/search.product.details.invoker/PackagingCode=DR5000-01/NewLinkLabel=DR+5000+UV-Vis+Spectrophotometer%2C+115+Vac/PREVIOUS_BREADCRUMB_ID=HC_SEARCH_BROWSE_PRODUCTSpectrophotometersColorimeters/SESSIONID|B3hOVFUxTnpjeE5qYzNakVtWjNWbGMzUkRUZz09QWxOWIRURQ==|; printed on Jul. 14, 2006.

"Drugstore.com-online pharmacy & drugstore, prescriptions filled"; drugstore.com; bearing dates of 1999-2006; pp. 1 (Sheets 1-3), pp. 2 (Sheets 1-4), pp. 3 (Sheets 1-2) (pp. total 1-9); drugstore.com, inc.; located at: http://www.drugstore.com/search/search.asp?searchtype=1&trx=28198&trxpl=60&ipp=20&srchtree=1&search=home+test+kit&Go.x=17&Go.y=16; printed on Jul. 10, 2006.

Duffy, Sj; Vita, JA; "Effects of phenolics on vascular endothelial function"; Current Opinion in Lipidology; bearing a date of Feb. 2003; pp. 21-27 (p. 1); vol. 14, Issue 1; PubMed; located at: http://www.ncbi.nlm.nih.gov/entrez/query.fcgi?cmd=Retrieve&db=PubMed&list_uids=12544657&dopt=Abstract; printed on Aug. 22, 2006.

Eskin, N. A. Michael; Dictionary of Nutraceuticals and Functional Foods (Functional Foods and Nutraceuticals); bearing a date of Dec. 19, 2005; 520 pp.; ISBN No. 0849315727; CRC Press (not provided).

"Family Age Groups"; testsymptomsathome.com; pp. 1-4; located at: http://www.testsymptomsathome.com/family_age_groups.asp; printed on Jul. 10, 2006.

"FDA OKs 3-Drug Combo Pill to Treat HIV"; bearing a date of Jun. 30, 2006; pp. 1-2; FoxNews.com; located at http://www.foxnews.corn/wires/2006Jun30/0.4670,AIDSRelief,00.html;.printed on Jun. 30, 2006.

Felkey, Bill G.; Berger, Bruce A.; Krueger, Kem P.; "The Pharmacist's Role in Treatment Adherence —Part 5: The Impact of Pharmacy-Specific Technology"; U.S. Pharmacist; bearing dates of 2005, 2000- 2005; and a posted date of Aug. 18, 2005; pp. 36-39 (pp. 1-6); vol. 30:08; Jobson Publishing, L.L.C.; located at: http://www.uspharmacist.com/index.asp?show=article&page=8_1547.htm; printed on.Nov. 13, 2005.

"Female Hormone Tests"; Home Health Testing; bearing dates of Dec. 1, 2005 and 2000; pp. 1-3; AbDiagnostics, Inc.; located at: http://www.homehealthtesting.com/female-hormone-tests.htm; printed on Jul. 24, 2006.

Fitzgerald, Katherine A.; O'Neill, Luke A.J.; Gearing, Andy J.H.; Callard, Robin E.; "The Cytokine Factsbook"; bearing a date of Sep. 2001; 515 pages; 2nd Edition; ISBN No. 0121551423; Academic Press; San Francisco, CA (not provided).

Gennaro, Alfonso R. (Ed); Remington: the Science and Practice of Pharmacy; bearing a date of Dec. 15, 2000; 2077 pages.; $20^{th}$ Edition; ISBN No. 0683306472; Lippincott Williams and Wilkins; Philadelphia, PA (not provided).

"Heart-Help's Handbook . . . Living with CM & CHF (Cardiomyopathy Heart Failure)"; bearing a date of Sep. 23, 2001; pp. 1-5; located at: http://www.heart-help.net/handbook.html; printed on Nov. 13, 2005.

"Home Allergy Tests"; Home Health Testing; bearing dates of Dec. 1, 2005 and 2000; pp. 1-3; AbDiagnostics, Inc.; located at: http://www.homehealthtesting.com/allergy-tests.htm; printed on Jul. 24, 2006.

"Home DNA Maternity Testing, Test Kit, Blood Paternity Testing"; Gtldna.com; bearing dates of 2002-2005; pp. 2-5; The Genetic Testing Laboratories, Inc.; located at: http://www.gtldna.com/maternitytest.html; printed on Jul. 10, 2006.

"Home DNA Prenatal Paternity, Maternity, Siblingship Test, Twin Zygosity, Kinship, Immigration DNA Testing"; Gtldna.com; bearing dates of Jul. 10, 2006 and 2002-2005; pp. 1-5; The Genetic Testing Laboratories, Inc.; located at: http://www.gtldna.com/dnatests.html; printed on Jul. 10, 2006.

"Home Test Kits, Blood Groups, Diabetes, Menopause, Prostate, Osteoporosis"; WorldWideShoppingMall.co.uk; pp. 1-2; World Wide Shopping Mall (WWSM); located at: http://www.worldwideshoppingmall.co.uk/Body-Soul/shelves/home . . . ; printed on Jul. 10, 2006.

"Home Test Kits, Hepatitis Test, HIV Test, Blood Type Test"; Quick Medical: Professional and Home Health Products; bearing a date of 2006; pp. 1-2; located at: http://www.quickmedical.com/monitors/blood testing/; printed on Jul. 10, 2006.

"Home Test Kits"; PriceGrabber.com; pp. 1 (Sheets 1-5), pp. 2 (Sheets 1-4), pp. 3 (1-5), pp. 4 (Sheets 1-3) (pp. total 1-17); PriceGrabber.com, Inc.; located at: http://www.pricegrabber.com/search_attrib.php/page_id=1970; printed on Jul. 10, 2006.

"Hormone Tests"; Home Health Testing; bearing dates on Dec. 1, 2005 and 2000; pp. 1-2; AbDiagnostics, Inc.; located at: http://www.homehealthtesting.com/hormone-tests.htm?gcnd-civ; printed on Jul. 24, 2006.

"Hormone Test Kit-Blood"; The Official Web Site of John R. Lee, MD: Your Information Source for Natural Hormone Balance and Natural HRT; pp. 1-3; Hormones Etc.; located at: http://www.johnleemd.com/store/prod_btest.html; printed on Jul. 10, 2006.

"Instant Anemia Test"; Health HomeTest.com; bearing dates of 2003-2005; pp. 1-9; B Scientific, Inc.; located at: http://www.health-hometest.com/product_info.php?products_id=81; printed on Jul. 24, 2006.

"Introducing Integrated Instrument +Reagent Analysis: Hach DR 5000™ UV-VIS Spectrophotometer and DR 2800™ Portable Spectrophotometer +new Hach TNTplus™ Vial Reagents"; Hach.com; bearing a date of 2006; pp. 1-3; Hach Company; located at: http://www.hach.com/photometry; printed on Jul. 14, 2006.

Keung, WM; "Anti-dipsotropic isoflavones: the potential therapeutic agents for alcohol dependence"; Medicinal Research Reviews; bearing a date of Nov. 2003; pp. 669-696 (pp. 1-2); vol. 23, Issue 6; PubMed; located at: http://www.ncbi.nlm.nih.gov/entrez/query.fcgi?cmd=Retrieve&db=PubMed&list_uids=12939789&dopt=Abstract; printed on Aug. 22, 2006.

Klinge, CM; Blankenship, KA; Risinger, KE; Bhatnagar, S; Noisin, EL; Sumanasekera, WK; Zhao, L; Brey, DM; Keynton, RS; "Resveratrol and estradiol rapidly activate MAPK signaling through estrogen receptors alpha and beta in endothelial cells"; The Journal of Biological Chemistry; bearing a date of Mar. 4, 2005; pp. 7460-7468 (pp. 1-2); vol. 280, Issue 9; PubMed; located at: http://www.ncbi.nlm.nih.gov/entrez/query.fcgi?cmd=Retrieve&db=Pub Med&list_uids=15615701&dopt=Abstract; printed on Aug. 22, 2006.

Li, JX; Xue, B; Chai, Q; Liu, ZX; Zhao, AP; Chen, LB; "Antihypertensive effect of total flavonoid fraction of Astragalus complanatus in hypertensive rats"; tThe Chinese Journal of Physiology; bearing a date of Jun. 30, 2005; pp. 101-106 (pp. 1-2); vol. 48, Issue 2; PubMed; located at: http://www.ncbi.nlm.nih.gov/entrez/query.fcgi?cmd=Retrieve&db=PubMed&list_uids=16201455&dopt=Abstract; printed on Aug. 22, 2006.

Lin, RC; Guthrie, S; Xie, CY; Mai, K; Lee, DY; Lumeng, L; Li, TK; "Isoflavonoid compounds extracted from Pueraria lobata suppress alcohol preference in a pharmacogenetic rat model of alcoholism"; Alcoholism, Clinical & Experimental Research; bearing a date of Jun. 1996; pp. 659-663 (pp. 1-2); vol. 20, Issue 4; PubMed; located at: http://www.ncbi.nlm.nih.gov/entrez/query.fcgi?CMD=Display&DB=pubmed; printed on Aug. 22, 2006.

Machha, A; Mustafa, MR; "Chronic treatment with flavonoids prevents endothelial dysfunction in spontaneously hypertensive rat aorta"; Journal of Cardiovascular Pharmacology; bearing a date of Jul. 2005; pp. 36-40 (p. 1); vol. 46, Issue 1; PubMed; located at: http://www.ncbi.nlm.nih.gov/entrez/query.fcgi?CMD=Display&DB=pubmed; printed on Aug. 22, 2006.

"Male Hormone Tests"; Home Health Testing; bearing dates of Dec. 1, 2005 and 2000; pp. 1-2; AbDiagnostics, Inc.; located at: http:www.homehealthtesting.com/male-hormone-tests.htm; printed on Jul. 24, 2006.

Mangels, Reed; "Vitamin B12 in the Vegan Diet"; The Vegetarian Resource Group: Nutrition; bearing dates of 1996-2003 and Jun. 20, 2006; pp. 1-3; The Vegetarian Resource Group; located at http://www.vrg.org/nutrition/b12.htm; printed on Jul. 7, 2006.

McClatchey, Kenneth D.; "Clinical Laboratory Medicine"; bearing a date of Jan. 15, 2002; 1693 pages; 2nd Edition; ISBN No. 0683307517; Lippincott Williams & Wilkins; Philadelphia, PA (not provided).

"Mineral & Toxic Element Tests"; Home Health Testing; bearing dates of Dec. 1, 2005 and 2000; pp. 1-3; AbDiagnostics, Inc.; located at: http://www.homehealthtesting.com/mineral-tests.htm; printed on Jul. 24, 2006.

Morrow, Daniel G.; Leirer, Von O.; Andrassy, Jill M.; "Using icons to convey medication schedule information"; Abstract; Science Direct; bearing dates of Aug. 1996, May 3, 1999 and 2000; pp. 1-2; vol. 27, Issue 4; Elsevier Ltd.; located at http://www.sciencedirect.com/science?_ob=ArticleURL&_udi=B6V1W-3WCSSG5-5&_coverDate=08%2F31%2F1996&_alid=413837048&_rdoc=1&_fmt=&_orig=sear ch&_qd=1&_cdi=5685&_sort=d&view=c&_acct=C000050221&_version=1&_urlVersion=0&_userid=10&md5=8a92d091167ef0d84c80fe26ae9fdbae; printed on Jun. 7, 2006.

Morrow, Daniel G.; Weiner, Michael; Young, James; Steinley, Douglas; Deer, Melissa; Murray, Michael D.; "Improving Medication Knowledge Among Older Adults with Heart Failure: A Patient-Centered Approach to Instruction Design"; The Gerontologist; bearing a date of 2005; pp. 545-552; vol. 45, No. 4; Practice Concepts; The Gerontological Society of America.

Nissen, David (Ed); Mosby's Drug Guide; bearing a date of 2004; ISBN No. 0-323-02872-1; Mosby, Inc: Elsevier; St. Louis, MO (not provided).

"Occult Blood (stool)—Take-Home Test Kit—$25" St. Vincent Healthcare; bearing a date of 2006; p. 1; located at http://www.svh-mt.org/services/akk_health/labcheck/occult_blood.htm; printed on Jul. 10, 2006.

"OnTime-Rx Medication Reminders"; bearing dates on 2000-2004; pp. 1-4; AmeliaPlex, Inc.; Orlando, FL; located at http://www.ontimerx.com/PDA/index.asp; printed on Nov. 13, 2005.

"Ovulation Predictor: Home Testing Kits"; Pharm.uky.edu; pp. 1-2; located at: http://www.pharm.uky.edu/hometest/Ovulate/OHP.html; printed on Jul. 10, 2006.

"Pain Relief / Injuries / Home Test Kits"; Round-Earth.com; pp. 1-2; Round Earth Publishing; located at: http://roundearth.stores.yahoo.net/relaxers.html; printed on Jul. 10, 2006.

"Personal Test Kits: Hormone Saliva Test, Home Hormone Test Kit"; Womenshealth.com; bearing a date of 2005; pp. 1-3; Women's Health America, Inc.; located at: http://www.womenshealth.com/personaltestkit.html; printed on Jul. 10, 2006.

Physicians' Desk Reference; the PDR Family Guide to Nutritional Supplements: An Authoritative A-to-Z Resource on the 100 Most Popular Nutritional Therapies and Nutraceuticals; bearing a date of Nov. 2003; 3000 pp.; $58^{th}$ Edition; ISBN No. 1563634724; Thomson PDR; Montvale, NJ (not provided).

Physicians' Desk Reference; the PDR Family Guide to Nutritional Supplements: An Authoritative A-to-Z Resource on the 100 Most Popular Nutritional Therapies and Nutraceuticals; bearing a date of Nov. 27, 2001; 352 pages; $1_{st}$ Edition; ISBN No. 0345433769; Ballantine Books (not provided).

Pregnancy Test, Ovulation Test, Drug Test by Medimpex; bearing a date of 2002; pp. 1-3; Medimpex United Inc., at: http://www.meditests.com/; printed on Jul. 10, 2006.

"Probiotics Basics"; bearing a date of 2004; pp. 1-11; CDRF, Dairy & Food Culture Technologies; located at: http://www.usprobiotics.org/basics/; printed on Jul. 7, 2006.

"Quality Standards Issued for Testing Herbal Products"; ScienceDaily; bearing dates of Apr. 18, 2006 and 1995-2006; pp. 1-2; ScienceDaily LLC; located at: http://www.sciencedaily.com/releases/2006/04/060418011332.htrn; printed on Jul. 14, 2006.

Rapport, Lisa; Lockwood, Brian; Nutraceuticals; bearing a date of Dec. 2001; 184 pages; $1^{st}$ Edition; ISBN No. 085369 503 2; Pharmaceutical Press (not provided).

Roberts, Arthur J.; Subak-Sharpe, Genelle; O'Brien, Mary E.; Nutraceuticals: The Complete Encyclopedia of Supplements, Herbs, Vitamins, and Healing Foods; bearing a date of Jan. 9, 2001; 669 pages; $1^{st}$ Edition; ISBN No. 0399526323; Perigee Trade (not provided).

Samuel, Buck S.; Gordon, Jeffrey I.; "A Humanized Gnotobiotic Mouse Model of Host-Archaeal-Bacterial Mutualism"; PNAS; bearing dates of 2006, Mar. 16, 2006, May 17, 2006 and Jun. 27, 2006; pp. 10011-10016; vol. 103, No. 26; The National Academy of Sciences of the USA; located at: www.pnas.org/cgi/doi/10.1073/pnas.0602187103.

Sarkar, FH; Adsule, S; Padhye, S; Kulkarni, S; Li, Y; "The role of genistein and synthetic derivatives of isoflavone in cancer prevention and therapy"; Mini Reviews in Medicinal Chemistry; bearing a date of Apr. 2006; pp. 401-407 (pp. 1-2); vol. 6, Issue 4; PubMed; located at: http://www.ncbi.nlm.nih.gov/entrez/query.fcgi?CMD=Display&DB=pubmed; printed on Aug. 22, 2006.

"Search Results"; Health HomeTest.com; bearing dates of 2003-2005; pp. 1-2; B Scientific, Inc.; located at: http://www.health-hometest.com/index.php?cPath=40; printed on Jul. 24, 2006.

"Single Parameter Test Kits"; Hach.com; bearing a date of 2006; pp. 1-9; Hach Company; located at: http://www.hach.com/hc/browse.exploded.product.category.catalog/PRODCAT0033/NewLinkLabel=Single+Parameter+Test+Kits/PREVIOUS_BREADCRUMB_ID=HC_SEARCH_BROWSE/SESSIONID|BkUxTlRVMO5UQTVPVFEzTONabmRXVnpkRT-VEVWc9PUEwdFhNVA==; printed on Jul. 14, 2006.

"Sleep Hormone Tests"; Home Health Testing; bearing dates of Dec. 1, 2005 and 2000; pp. 1-3; AbDiagnostics, Inc.; located at: http://www.homehealthtesting.com/sleep-tests.htm; printed on Jul. 24, 2006.

Smith, Ann; Heckelman, Patricia E.; O'Neil, Maryadele J. (Ed); Budavari, Susan (Ed); The Merck Index: An Encyclopedia of Chemicals, Drugs and Biologicals; bearing a date of Oct. 2001; 2564 pages; $13^{th}$ Edition; ISBN No. 0911910131; John Wiley and Sons and Merck & Co. Inc.; Whitehouse Station, NJ (not provided).

Sojourner, Russell J.; Wogalter, Michael S.; "The Influence of Pictorials on Evaluations of Prescription Medication Instructions"; Drug Information Journal; bearing a date of 1997; pp. 963-972; vol. 31; Drug Information Association, Inc.

"Spectrophotometers and Colorimeters"; Hach.com; bearing a date of 2006; pp. 1-2; Hach Company; located at: http://www.hach.com/hc/browse.exploded.product.category.catalog/PRODCAT0001/NewLinkLabel=Spectrophotometers+%26+Colorimeters/PREVIOUS_BREADCRUMB_ID=HC_SEARCH_BROWSE/SESSIONID|A3INVE14TnpJeU1TWm5kVIZ6ZEZCWIQxZEIN-VEUxTIE9PUNUTQ==|; printed on Jul. 14, 2006.

"Stress Hormone Tests"; Home Health Testing; bearing dates of Dec. 1, 2005 and 2000; pp. 1-3; AbDiagnostics, Inc., located at: http://www.homehealthtesting.com/stress-hormone-tests.htm; printed on Jul. 24, 2006.

"Talking Medicine Identifiers"; bearing a date of Jul. 10, 2003; pp. 1-5.

"UV-Vis-NIR Advantage Note"; bearing a date of May 2005; No. 1; pp. 1-3; Varian, Inc.; located at: www.varianinc.com/image/vimage/docs/applications/apps/uv_an1.pdf; printed on Jul. 14, 2006.

"UV-Vis-IR-Raman Spectrophotometers"; Micro Photonics; bearing a date of Dec. 7, 2005; pp. 1-2; Micro Photonics, Inc.; located at: http://www.microphotonics.com/spectrophotometer.html; printed on Jul. 14, 2006.

Wallerath, T; Deckert, G; Ternes, T; Anderson, H; Li, H; Witte, K; Forstermann, U; "Resveratrol, a polyphenolic phytoalexin present in red wine, enhances expression and activity of endothelial nitric oxide synthase"; Circulation; bearing a date of Sep. 24, 2002; pp. 1652-1658 (pp. 1-2); vol. 106, Issue 13; PubMed; located at: http://www.ncbi.nlm.nih.gov/entrez/query.fcgi?cmd=Retrieve&db=PubMed&list_uids=12270858&dopt=Abstract; printed on Aug. 22, 2006.

Walji, Rishma; "Acidophilus Effects, Benefits and Other Information"; About: Alternative Medicine; bearing a date of 2006; p. 1; About, Inc., A part of *The New York Times Company*; located at http://altmedicine.about.com/cs/digestiveproblems/a/Acidophilus.htm; printed on Jul. 7, 2006.

Walji, Rishma; "What are Probiotics?"; About: Alternative Medicine; bearing a date of 2006; p. 1; Abount, Inc., A part of *The New York Times Company*; located at: http://altmedicine.about.com/cs/digestiveproblems/a/Acidophilus_2.htm; printed on Jul. 7, 2006.

"What are Probiotics?"; USProbiotics; bearing a date of 2004; 1 p.; CDFR, Dairy & Food Culture Technologies; located at: http://www.usprobiotics.org/mainpageframe.htm; printed on Jul. 7, 2006.

Widdershoven, J.; Van Munster, P.; De Abreu, R.; Bosman, H.; Van Lith, TH.; Van Der Putten-Van Meyel, M.; Motohara, K.; Matsuda, I.; "Four Methods Compared for Measuring Des-Carboxy-Prothrombin (PIVKA-II)"; Clinical Chemistry; bearing a date of 1987; pp. 2074-2078; vol. 33, No. 11.

Wildman, Robert E.C.; Handbook of Nutraceuticals and Functional Foods; bearing a date of Nov. 10, 2000; 568 pages; $1^{st}$ Edition; ISBN No. 0849387345; CRC Press (not provided).

Wynn, Susan G.; Emerging Therapies: Using Herbs and Nutraceuticals for Small Animals; bearing a date of 1999; 160 pages; $1^{st}$ Edition; ISBN No. 1583260102; American Animal Hospital Assn Press (not provided).

Wald, NJ; Law, MR; "A strategy to reduce cardiovascular disease by more than 80%"; BMJ; Jun. 28, 2003; pp. 1-6; vol. 326; located at: www.bmj.com.

Smith, Stevie; "New Chip Identifies Bird Flu in Humans"; The Tech Herald.com, WOTR Limited; 2008; located at: www.thetechherald.com/article/php200813/520/new-chip-identifies-bird-flu-in-humans; Bearing a date of Mar. 25, 2008; printed on Sep. 8, 2008; pp. 1-6.

PCT International Search Report; International App. No. PCT/US07/25451; Sep. 15, 2008; pp. 1-2.

PCT International Search Report; International App. No. PCT/US07/20272; Sep. 15, 2008; pp. 1-2.

PCT International Search Report; International App. No. PCT/US07/20305; Sep. 11, 2008; pp. 1-2.

PCT International Search Report; International App. No. PCT/US07/20283; Sep. 11, 2008; pp. 1-2.

PCT International Search Report; International App. No. PCT/US07/14994; Sep. 9, 2008; pp. 1-2.

PCT International Search Report; International App. No. PCT/US08/07993; Sep. 8, 2008; pp. 1-3.
PCT International Search Report; International App. No. PCT/US06/47451; Sep. 5, 2008; pp. 1-2.
PCT International Search Report; International App. No. PCT/US06/44658; Aug. 29, 2008; pp. 1-2.
PCT International Search Report; International App. No. PCT/US06/44279; Aug. 19, 2008; pp. 1-3.
PCT International Search Report; International App. No. PCT/US06/44283; Aug. 18, 2008; pp. 1-2.
PCT International Search Report; International App. No. PCT/US07/14266; Jul. 21, 2008; pp. 1-2.
Edible Science; bearing dates of 2005—2010; pp. 1-2; located at: http://www.ediblescience.com; printed on May 13, 2010.
Fightermins; bearing a date of 2010; 1 page; located at: http://www.figtermins.com/index.isp; printed on May 13, 2010.
Ideal Health; "Custom Essentials"; "The Priva Test"; bearing a date of 2010; total of 5 pages; located at: http://www.idealhealth.com; printed on May 13, 2010; The Trump Network.
I-Vita; bearing a date of 2009; 1 page; located at: http://www.mynutrapack.com/index.html; printed on May 13, 2010.
LifeScript; bearing dates of 1998—2010; 1 page; located at: http://vitamins.lifescript.com/Begin.asp?BID=14971&PROMO=zluswiec; printed on May 13, 2010.
Mindell, Earl, Dr.; Vitaganic "Custom-Made Multivitamins"; bearing dates of 2005-2010; 1 page; located at: http://drmindell.vitaganic.com/; printed on May 13, 2010.
My Vitamin Clinic; bearing a date of 2010; 1 page; located at: http://www.myvitaminclinic.com/index.jsp; printed on May 13, 2010.
MyNutraPack; 1 page; located at http://www.mynutrapack.com/index.html; printed on May 25, 2010.
MyVitaminRx; bearing a date of 2007; 1 page; located at: http://www.myvitaminsrx.com/CustomNutrition.aspx?ID=MoonlightSpa; printed on May 13, 2010.
Nature Made; pp. 1-2; located at: http://www.naturemade.com; printed on May 13, 2010.
NutriHerb; bearing dates of 2001-2009; pp. 1-2; Nutri Herb, Inc.; located at: http://www.nutriherb.net/custom_made_to_order_herbal_vitamins_supplements.html; printed on May 13, 2010.
Pharmative LLC; 1 page; located at: http://www.pharmavite.com/index.asp; printed on May 13, 2010.
"Pharmavite LLC Launches New Direct-To-Consumer Company" Press Release; Pharmavite LLC; bearing a date of Sep. 4, 2009; 1 page; located at: http:www.pharmavite.com/MediaCenter/MC_PR.asp?ID=164; printed on May 13, 2010.
Signature Supplements; bearing a date of 2009; pp. 1-2; located at: http://www.signaturesupplements.com/jsp/main/index.jsp; printed on May 13, 2010; Signature Supplements.
SOYJOY®; bearing a date of 2010; 1 page; located at: http://www.soyjoy.com/index.aspx; printed on May 13, 2010; Pharmavite LLC.
Total Health Nutrients; pp. 1-2; located at: http://www.totalthealthnutrients.com/ph/index.html; printed on May 13, 2010.
VitaminID.com; bearing a date of 2010; 1 page; located at: http://www.vitaminid.com/webapp/wcs/stores/servlet/StoreView?storeId=201&langId =-1; printed on May 25, 2010; Pharmavite Direct LLC.
Vitamins on Demand; bearing a date of 2010; 1 page; located at: http://www.vitaminsondemand.com/?gclid=CNbygPut9aACFRYhDQodyGkivw; printed on May 13, 2010.

VitaXact; bearing a date of 2009; 1 page; located at http://www.vitaxact.com; printed on May 13, 2010.
Weil, Andrew, M.D.; "Dr. Weil's Vitamin Advisor & Complete Program Supplements"; bearing a date of 2010; 1 page; located at: https://www.drweilvitaminadvisor.com/drw/ecs/Va2/land_goog_08girl.html?aid=999910&aparam=TSAsGOOGLEApr10VA_vitamins&refcd—GO000000101882154s_vitamins&tsacr=GO3784957603&gclig=CM3NpLzm9aACFRYhDQodyGkivw; printed on May 13, 2010; Weil Lifestyle Custom Pak.
U.S. Appl. No. 12/924,700, Jung et al.
U.S. Appl. No. 13/374,765, Jung et al.
Mullett, Charles J. et al.; "Computerized antimicrobial decision support: an offline evaluation of a database-driven empiric antimicrobial guidance program in hospitalized patients with a bloodstream infection"; International Journal of Medical Informatics; 2004; pp. 455-460; vol. 73; Elsevier Ireland Ltd.
Sriskanthan, N. and Subramanian, K. R.; "Braille Display Terminal for Personal Computers"; IEEE Transactions on Consumer Electronics; May 1990; pp. 121-128; vol. 36, No. 2; IEEE.
UK Intellectual Property Office Examination Report Under Section 18(3); App. No. GB1000316.8; Jul. 26, 2011; pp. 1-3.
U.S. Appl. No. 11/900,660, Jung et al.
U.S. Appl. No. 11/900,649, Jung et al.
U.S. Appl. No. 11/900,637, Jung et al.
U.S. Appl. No. 11/893,608, Jung et al.
U.S. Appl. No. 11/893,606, Jung et al.
U.S. Appl. No. 11/893,605, Jung et al.
U.S. Appl. No. 11/888,627, Jung et al.
U.S. Appl. No. 11/888,614, Jung et al.
U.S. Appl. No. 11/888,613, Jung et al.
Brüssow, Harald; "Phage Therapy: the *Escherichia coli* experience"; Microbiology; 2005; pp. 2133-2140; vol. 151.
Merril, Carl R.; Biswas, Biswajit; Carlton, Richard; Jensen, Nicole C.; Creed, G. Joseph; Zullo, Steve; Adhya, Sankar; "Long-circulating bacteriophage as antibacterial agents"; Proc. Natl. Acad. Sci.; Apr. 1996; pp. 3188-3192; vol. 93.
PCT International Search Report; International App. No. PCT/US2005/033347; Aug. 23, 2006; 4 pages.
PCT International Search Report; International App. No. PCT/US03/41466; Aug. 26, 2004; 2 pages.
PCT International Search Report; International App. No. PCT/US01/09745; Aug. 2, 2001; 1 page.
PCT International Search Report; International App. No. PCT/IL99/00122; Aug. 30, 1999; 2 pages.
"Smart Pillbox Goes Direct to Consumer"; Health Data Management; Bearing dates of Aug. 28, 2007 and Aug. 29, 2007; pp. 1-2; Health Data Management and SourceMedia, Inc.; located at: http://healthdatamanagement.com/html/news/NewsStory.cfm?articleId=15652; printed on Aug. 29, 2007.
Woolley, AT et al.; "Functional integration of PCR amplification and capillary electrophoresis in a microfabricated DNA analysis device"; Anal Chem; Bearing a date of Dec. 1, 1996; pp. 4081-4086 (p. 1); vol. 68, No. 23; PubMed; located at: hup://www.ncbi.nlm.nih.gov; printed on Aug. 2, 2007.

\* cited by examiner

COMPUTATIONAL AND/OR CONTROL SYSTEMS AND METHODS RELATED TO NUTRACEUTICAL AGENT SELECTION AND DOSING

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/453,571, entitled INDIVIDUALIZED PHARMACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 14 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/478,341, entitled COMPUTATIONAL AND/OR CONTROL SYSTEMS RELATED TO INDIVIDUALIZED NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood Jr. as inventors, filed 28 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/478,296, entitled COMPUTATIONAL AND/OR CONTROL SYSTEMS RELATED TO INDIVIDUALIZED NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood Jr. as inventors, filed 28 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/486,998, entitled COMPUTATIONAL AND/OR CONTROL SYSTEMS RELATED TO INDIVIDUALIZED PHARMACEUTICAL AND NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood Jr. as inventors, filed 14 Jul. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/486,973, entitled COMPUTATIONAL AND/OR CONTROL SYSTEMS RELATED TO INDIVIDUALIZED PHARMACEUTICAL AND NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood Jr. as inventors, filed 14 Jul. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/474,109, entitled CUSTOMIZED VISUAL MARKING FOR MEDICATION LABELING, naming Edward K. Y. Jung, Royce A. Levien, Robert W. Lord, Mark A. Malamud, John D. Rinaldo, Jr., and Lowell L. Wood Jr. as inventors, filed 23 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/314,945, entitled GENERATING A REQUEST FROM A NUTRACEUTICAL INVENTORY, naming Edward K. Y. Jung, Royce A. Levien, Robert W. Lord, Mark A. Malamud, John D. Rinaldo, Jr., Clarence T. Tegreene, and Lowell L. Wood Jr. as inventors, filed 20 Dec. 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/291,482, entitled GENERATING A NUTRACEUTICAL REQUEST FROM AN INVENTORY, naming Edward K. Y. Jung, Royce A. Levien, Robert W. Lord, Mark A. Malamud, John D. Rinaldo, Jr., Clarence T. Tegreene, and Lowell L. Wood Jr. as inventors, filed 30 Nov. 2005, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to computational and/or control systems and methods related to nutraceutical agent selection and dosing.

SUMMARY

In some embodiments a method is provided that includes accepting data related to one or more specified goals of an individual; intaking information linked to one or more parameters associated with the one or more specified goals of the individual; selecting one or more nutraceutical agents in response to the intaking the information linked to the one or more parameters associated with the one or more specified goals of the individual; and indicating one or more dosages of the one or more nutraceutical agents in response to the selecting the one or more nutraceutical agents in response to the intaking the information linked to the one or more parameters associated with the one or more specified goals of the individual. In addition to the foregoing, other method aspects are described in the claims, drawings, and/or text forming a part of the present disclosure.

In some embodiments a method is provided that includes accepting data related to one or more specified goals of an individual; intaking information linked to one or more parameters associated with the one or more specified goals of the individual; and transmitting one or more signals in response to the intaking the information linked to the one or more parameters associated with the one or more specified goals of the individual. In addition to the foregoing, other method aspects are described in the claims, drawings, and/or text forming a part of the present disclosure.

In some embodiments a method is provided that includes receiving one or more signals transmitted in response to intaking information linked to one or more parameters associated with one or more specified goals of an individual; selecting one or more nutraceutical agents in response to the receiving the one or more signals transmitted in response to the intaking the information linked to the one or more parameters associated with the one or more specified goals of the individual; and indicating one or more dosages of the one or more nutraceutical agents in response to the selecting the one or more nutraceutical agents in response to the receiving the one or more signals transmitted in response to the intaking the information linked to the one or more parameters associated with the one or more specified goals of the individual. In addition to the foregoing, other method aspects are described in the claims, drawings, and/or text forming a part of the present disclosure.

In some embodiments a system is provided that includes circuitry for accepting data related to one or more specified goals of an individual; circuitry for intaking information linked to one or more parameters associated with the one or more specified goals of the individual; circuitry for selecting one or more nutraceutical agents responsive to the circuitry for intaking the information linked to the one or more parameters associated with the one or more specified goals of the individual; and circuitry for indicating one or more dosages of the one or more nutraceutical agents responsive to the circuitry for selecting the one or more nutraceutical agents responsive to the circuitry for intaking the information linked to the one or more parameters associated with the one or more specified goals of the individual. In addition to the foregoing, other system aspects are described in the claims, drawings, and/or text forming a part of the present disclosure.

In some embodiments a system is provided that includes circuitry for accepting data related to one or more specified goals of an individual; circuitry for intaking information linked to one or more parameters associated with the one or more specified goals of the individual; and circuitry for transmitting one or more signals responsive to the circuitry for intaking the information linked to the one or more parameters associated with the one or more specified goals of the individual. In addition to the foregoing, other system aspects are described in the claims, drawings, and/or text forming a part of the present disclosure.

In some embodiments a system is provided that includes circuitry for receiving one or more signals transmitted in response to intaking information linked to one or more parameters associated with one or more specified goals of an individual; circuitry for selecting one or more nutraceutical agents responsive to the circuitry for receiving the one or more signals transmitted in response to intaking the information linked to the one or more parameters associated with the one or more specified goals of the individual; and circuitry for indicating one or more dosages of the one or more nutraceutical agents responsive to the circuitry for selecting the one or more nutraceutical agents responsive to the circuitry for receiving the one or more signals transmitted in response to intaking the information linked to the one or more parameters associated with the one or more specified goals of the individual. In addition to the foregoing, other system aspects are described in the claims, drawings, and/or text forming a part of the present disclosure.

In some embodiments a system is provided that includes means for accepting data related to one or more specified goals of an individual; means for intaking information linked to one or more parameters associated with the one or more specified goals of the individual; means for selecting one or more nutraceutical agents responsive to the means for intaking the information linked to the one or more parameters associated with the one or more specified goals of the individual; and means for indicating one or more dosages of the one or more nutraceutical agents responsive to the means for selecting the one or more nutraceutical agents responsive to the means for intaking the information linked to the one or more parameters associated with the one or more specified goals of the individual. In addition to the foregoing, other system aspects are described in the claims, drawings, and/or text forming a part of the present disclosure.

In some embodiments a system is provided that includes means for accepting data related to one or more specified goals of an individual; means for intaking information linked to one or more parameters associated with the one or more specified goals of the individual; and means for transmitting one or more signals responsive to the means for intaking the information linked to the one or more parameters associated with the one or more specified goals of the individual. In addition to the foregoing, other system aspects are described in the claims, drawings, and/or text forming a part of the present disclosure.

In some embodiments a system is provided that includes means for receiving one or more signals transmitted in response to intaking information linked to one or more parameters associated with one or more specified goals of an individual; means for selecting one or more nutraceutical agents responsive to the means for receiving the one or more signals transmitted in response to intaking the information linked to the one or more parameters associated with the one or more specified goals of the individual; and means for indicating one or more dosages of the one or more nutraceutical agents responsive to the means for selecting the one or more nutraceutical agents responsive to the means for receiving the one or more signals transmitted in response to intaking the information linked to the one or more parameters associated with the one or more specified goals of the individual. In addition to the foregoing, other system aspects are described in the claims, drawings, and/or text forming a part of the present disclosure.

In some embodiments a system is provided that includes a signal-bearing medium bearing: one or more instructions for accepting data related to one or more specified goals of an individual; one or more instructions for intaking information linked to one or more parameters associated with the one or more specified goals of the individual; one or more instructions for selecting one or more nutraceutical agents in response to the intaking the information linked to the one or more parameters associated with the one or more specified goals of the individual; and one or more instructions for indicating one or more dosages of the one or more nutraceutical agents in response to the selecting the one or more nutraceutical agents in response to the intaking the information linked to the one or more parameters associated with the one or more specified goals of the individual. In addition to the foregoing, other system aspects are described in the claims, drawings, and/or text forming a part of the present disclosure.

In some embodiments a system is provided that includes a signal-bearing medium bearing: one or more instructions for accepting data related to one or more specified goals of an individual; one or more instructions for intaking information linked to one or more parameters associated with the one or more specified goals of the individual; and one or more instructions for transmitting one or more signals in response to the intaking the information linked to the one or more parameters associated with the one or more specified goals of the individual. In addition to the foregoing, other system aspects are described in the claims, drawings, and/or text forming a part of the present disclosure.

In some embodiments a system is provided that includes a signal-bearing medium bearing: one or more instructions for receiving one or more signals transmitted in response to intaking information linked to one or more parameters associated with one or more specified goals of an individual; one or more instructions for selecting one or more nutraceutical agents in response to the receiving the one or more signals transmitted in response to the intaking the information linked to the one or more parameters associated with the one or more specified goals of the individual; and one or more instructions for indicating one or more dosages of the one or more nutraceutical agents in response to the selecting the one or more nutraceutical agents in response to the receiving the one or more signals transmitted in response to the intaking the information linked to the one or more parameters associated with the one or more specified goals of the individual. In addition to the foregoing, other system aspects are described in the claims, drawings, and/or text forming a part of the present disclosure.

In some embodiments, means include but are not limited to circuitry and/or programming for effecting the herein-referenced functional aspects; the circuitry and/or programming can be virtually any combination of hardware, software, and/or firmware configured to effect the herein-referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

DETAILED DESCRIPTION

Figure 1:
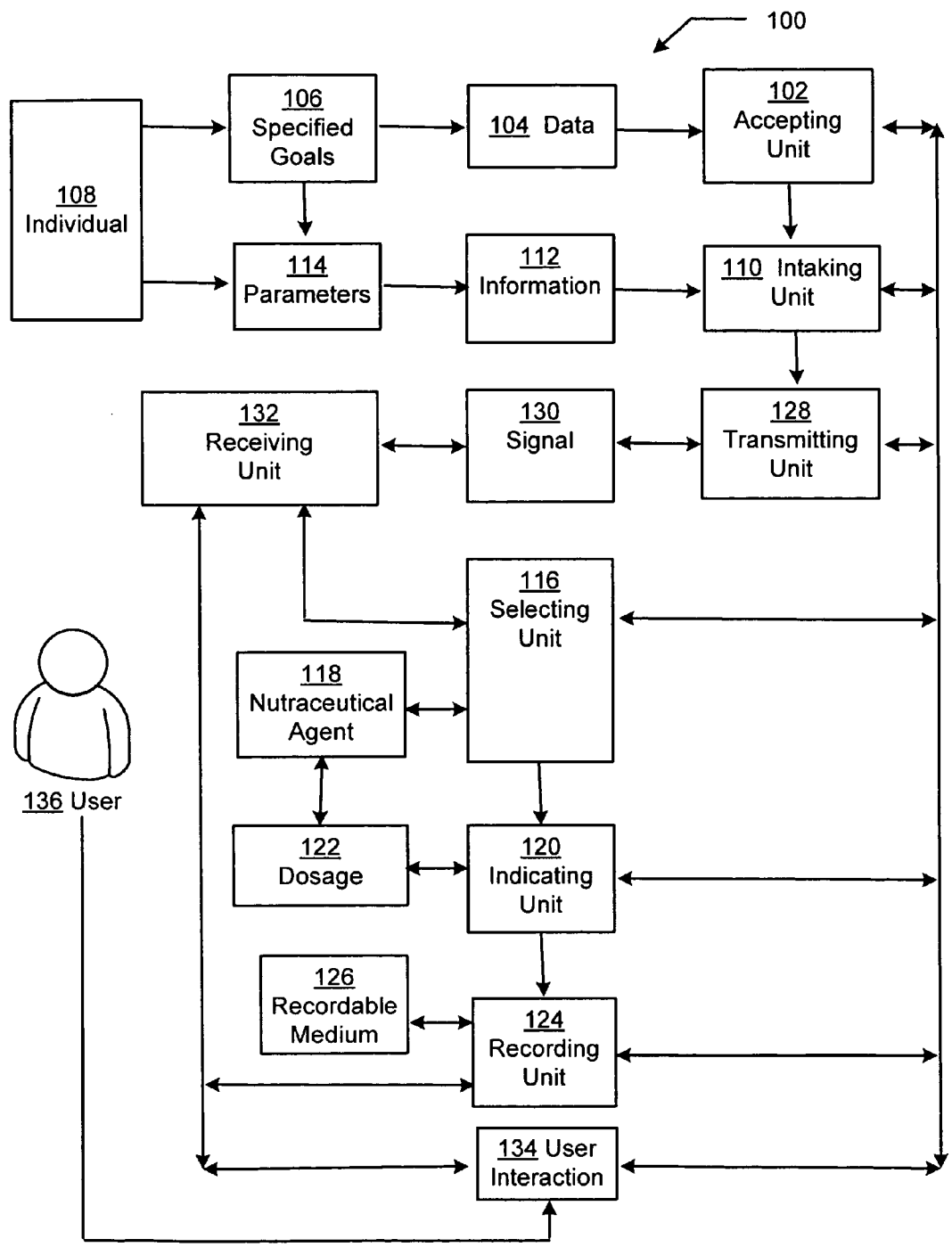
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates an example system 100 in which embodiments may be implemented. In some embodiments, the system 100 is operable to provide a method and system for nutraceutical agent 118 selection and dosing. In some embodiments, the system 100 may be used by one or more individuals 108 to achieve one or more specified goals 106. In some embodiments, one or more accepting units 102 accept data 104 related to one or more specified goals 106 of one or more individuals 108. In some embodiments, one or more intaking units 110 intake information 112 linked to one or more parameters 114 associated with one or more specified goals 106 of an individual 108. In some embodiments, one or more selecting units 116 select one or more nutraceutical agents 118 in response to intaking information 112 linked to one or more parameters 114 associated with one or more specified goals 106 of an individual 108. In some embodiments, one or more indicating units 120 indicate one or more dosages 122 of one or more nutraceutical agents 118 in response to selecting the one or more nutraceutical agents 118 in response to intaking information 112 linked to one or more parameters 114 associated with the one or more specified goals 106 of the individual 108. In some embodiments, one or more recording units 124 record the results of: accepting data 104 related to one or more specified goals 106 of an individual 108, intaking information 112 linked to one or more parameters 114 associated with the one or more specified goals 106 of the individual 108, selecting one or more nutraceutical agents 118 in response to intaking information 112 linked to one or more parameters 114 associated with the one or more specified goals 106 of the individual 108, indicating one or more dosages 122 of the one or more nutraceutical agents 118 in response to selecting one or more nutraceutical agents 118 in response to intaking information 112 linked to one or more parameters 114 associated with the one or more specified goals 106 of the individual 108, or substantially any combination thereof, on a recordable-medium 126. In some embodiments, one or more transmitting units 128 transmit one or more signals 130 in response to intaking information 112 linked to one or more parameters 114 associated with one or more specified goals 106 of an individual 108. In some embodiments, one or more receiving units 132 receive one or more signals 130 transmitted in response to intaking information 112 linked to one or more parameters 114 associated with one or more specified goals 106 of the individual 108. In some embodiments, system 100 provides for user interaction 134 with one or more users 136. In some embodiments, such user interaction 134 can occur with one or more recording units 124, one or more indicating units 120, one or more selecting units 116, one or more receiving units 132, one or more transmitting units 128, one or more intaking units 110, one or more accepting units 102, and substantially any combination thereof. In some embodiments of system 100, one or more recording units 124, one or more indicating units 120, one or more selecting units 116, one or more receiving units 132, one or more transmitting units 128, one or more intaking units 110, and one or more accepting units 102, are hardwired together in substantially any combination. In some embodiments of system 100, one or more recording units 124, one or more indicating units 120, one or more selecting units 116, one or more receiving units 132, one or more transmitting units 128, one or more intaking units 110, and one or more accepting units 102, may communicate through wireless connection. Numerous technologies may be used to establish and maintain wireless connections. In some embodiments of system 100, one or more recording units 124, one or more indicating units 120, one or more selecting units 116, one or more receiving units 132, one or more transmitting units 128, one or more intaking units 110, and one or more accepting units 102, may communicate through wireless connection and hardwired connections in substantially any combination. In some embodiments, user interaction 134 is provided through hardwired connections. In some embodiments, user interaction 134 is provided through wireless connections. In some embodiments, user interaction 134 is provided through hardwired and wireless connections.

Accepting Unit 102

The system 100 can include one or more accepting units 102. In some embodiments, one or more accepting units 102 can be used to accept data 104 related to one or more specified goals 106 of one or more individuals 108. In some embodiments, one or more accepting units 102 can include a physical device with allows data 104 entry, such as a touchpad, keypad, hardwired telephone, and the like. In some embodiments, one or more accepting units 102 can include a wireless connection that allows the one or more accepting units 102 to accept data 104 from one or more individuals 108 through a wireless connection. For example, in some embodiments, one or more accepting units 102 may accept data 104 from one or more individuals 108 through use of a cellular telephone, a personal digital assistant, a wireless computer, and the like.

Data 104/Specified Goals 106

The system 100 can include data 104 related to one or more specified goals 106 of an individual 108. In some embodiments, the data 104 can be related to one or more physical characteristics of an individual 108. In some embodiments, the data 104 can be related to one or more mental characteristics of an individual 108. In some embodiments, the data 104 can be related to one or more physiological characteristics of an individual 108. In some embodiments, the data 104 can be related to one or more performance characteristics of an individual 108. In some embodiments, the data 104 can be related to one or more psychological characteristics of an individual 108. Data 104 can be related to numerous types of specified goals 106. For example, in some embodiments, the data 104 can be related to attentiveness, alertness, test performance, relaxation, pain, fever, attractiveness, anxiety, fall, injury, accident, bite, bleeding, inflammation, infection, drowsiness, insomnia, discomfort, stress, grooming, appearance, capability, performance, improvement, enhancement, curtailment, wellbeing, vitality, vigor, disability, phobia, malady, psychosis, environmental extremes, environmental exposure, dysfunction, disease symptom, chronic condition, mental acuity, emotional behavior, physical prowess, addiction, obsession, therapy, remedy, behavior, nutrition, diet (includes weight-loss), exercise, immunization, prevention, diagnosis, subscription, regimen, social performance, social interaction, endurance, sexual attribute, sexual performance, age-related attribute, age-related condition, prophylaxis, treatment, and substantially any combination thereof.

Individual 108

The system 100 can include one or more individuals 108. In some embodiments, an individual 108 may be afflicted with a diagnosed condition. For example, in some embodiments, an individual 108 may be afflicted with depression, anemia, obesity, insomnia, lower hormone levels, and the like. In some embodiments, an individual 108 may be afflicted with an undiagnosed condition. In some embodiments, such an undiagnosed condition may be an actual condition or a perceived condition.

Intaking Unit 110

The system 100 can include one or more intaking units 110. In some embodiments, one or more intaking units 110 can be used to intake information 112 linked to one or more parameters 114 associated with one or more specified goals 106 of an individual 108. In some embodiments, one or more intaking units 110 include instrumentation that can be used to assay one or more samples linked to an individual 108. In some embodiments, one or more intaking units 110 can be used to determine one or more levels of one or more metabolic indicators linked to an individual 108. In some embodiments, one or more intaking units 110 can be used to determine one or more levels of one or more metabolic activities linked to the individual 108. In some embodiments, one or more intaking units 110 can be used to determine one or more levels of one or more nutraceutical agents 118 linked to the individual 108. In some embodiments, one or more intaking units 110 can be used to determine one or more levels of one or more pharmaceutical agents linked to the individual 108. In some embodiments, one or more intaking units 110 can intake information 112 from another device. For example, in some embodiments, one or more intaking units 110 can intake information 112 provided by a diagnostic device. Such diagnostic devices include, but are not limited to, devices used to analyze bodily samples obtained from an individual 108 (i.e., blood, urine, saliva, synovial fluid, pleural fluid, peritoneal fluid, breath, skin, tissue, tears, mucus, genital products, hair, fecal material, and the like), devices used to analyze the appearance of an individual 108 (i.e., eye color, skin color, hair color, the presence or absence of bags under the eyes, presence or absence of hair, and the like), devices used to analyze a characteristic of the individual 108 (i.e., speech, reaction time, reflexes, temperature, eye dilation, retinal profile, height, weight, waistline, and the like), and other devices used to diagnose and/or analyze an individual 108. In some embodiments, one or more intaking units 110 can be included within system 100 through use of a hardwired connection. In some embodiments, one or more intaking units 110 can be included within system 100 through use of a wireless connection. In some embodiments, one or more intaking units 110 can be included within system 100 through use of a hardwired and a wireless connection. For example, in some embodiments, one or more intaking units 110 may intake information 112 from a diagnostic or analytical device that is hardwired to the intaking unit 110. In other embodiments, one or more intaking units 110 may intake information 112 from a diagnostic or analytical device through use of a wireless connection.

Selecting Unit 116

The system 100 can include one or more selecting units 116. In some embodiments, one or more selecting units 116 can be used to select one or more nutraceutical agents 118 in response to intaking information 112 linked to one or more parameters 114 associated with one or more specified goals 106 of an individual 108. In some embodiments, one or more selecting units 116 can be used to select one or more nutraceutical agents 118 to increase one or more levels of one or more components associated with the one or more specified goals 106 of the individual 108. In some embodiments, one or more selecting units 116 can be used to select one or more nutraceutical agents 118 to decrease one or more levels of one or more components associated with the one or more specified goals 106 of the individual 108. In some embodiments, one or more selecting units 116 can be used to select one or more nutraceutical agents 118 that stimulate one or more metabolic pathways linked to the individual 108. In some embodiments, one or more selecting units 116 can be used to select one or more nutraceutical agents 118 that inhibit one or more metabolic pathways linked to the individual 108. In some embodiments, one or more selecting units 116 can be used to select at least one vitamin, mineral, enzyme, amino acid, homeopathic supplement, toxin, homeopathic substance, traditional remedy, herbal supplement, glandular supplement, or substantially any combination thereof. In some embodiments, one or more selecting units 116 may access one or more databases that include information 112 with regard to nutraceutical agents 118, pharmaceutical agents, interaction of nutraceutical agents 118 with pharmaceutical agents, interaction of nutraceutical agents 118 and/or pharmaceutical agents with other substances, such as foods, beverages, over the counter drugs, and the like. In some embodiments, such databases may be included within one or more selecting units 116. In some embodiments, such databases may be remote from the one or more selecting units 116.

Numerous criteria may be used to select nutraceutical agents 118. Examples of such criteria include, but are not limited to, price, availability, dosage form, interactions with other substances, method of administration (i.e., oral, nasal, pulmonary, and the like), time of administration, time of effect, duration of effect, single or multiple administration, and the like. In some embodiments, one or more selecting units 116 can be included within system 100 through use of a hardwired connection. In some embodiments, one or more selecting units 116 can be included within system 100 through use of a wireless connection. In some embodiments, one or more selecting units 116 can be included within system 100 through use of a hardwired and a wireless connection.

Nutraceutical Agent 118

Nutraceutical agents 118 typically include natural, bioactive chemical compounds or any substance that is a plant, food, an extracted part of a food, that provides medical or health benefits but which generally fall outside regulations controlling pharmaceuticals. Included in this category of substances may be foods, isolated nutrients, supplements and herbs. Nutraceuticals are often referred to as phytochemicals or functional foods and include dietary supplements. Numerous nutraceuticals have been described (i.e., Roberts et al., Nutraceuticals: The Complete Encyclopedia of Supplements, Herbs, Vitamins, and Healing Foods, 1$^{st}$ Edition, Perigee Trade (2001) and Susan G. Wynn, Emerging Therapies: Using Herbs and Nutraceuticals for Small Animals, American Animal Hospital Assn Press (1999); and Handbook of Nutraceuticals and Functional Foods., edited by Robert E. C. Wildman, CRC Press (2001)). Examples of nutraceutical agents 118 include, but are not limited to, Amino Acids, Terpenoids, Carotenoid Terpenoids (Lycopene, Beta-Carotene, Alpha-Carotene, Lutein, Zeaxanthin, Astaxanthin), Herbal Supplements, Homeopathic Supplements, Glandular Supplements, Non-Carotenoid Terpeniods (Perillyl Alcohol, Saponins, Terpeneol, Terpene Limonoids), Polyphenolics, Flavonoid Polyphenolics (Anthocyanins, Catechins, Isoflavones, Hesperetin, Naringin, Rutin, Quercetin, Silymarin, Tangeretin, Tannins), Phenolic Acids (Ellagic Acid, Chlorogenic Acid, Para-Coumaric Acid, Phytic Acid, Cinnamic Acid), Other Non-Flavonoid Polyphenolics (Curcumin, Resveratrol, Lignans), Glucosinolates, Isothiocyanates (Phenethyl Isothiocyanate, Benzyl Isothiocyanate, Sulforaphane), Indoles (Indole-3-Carbinol (I3C), Thiosulfonates, Phytosterols (Beta-Sitosterol), Anthraquinones (Senna, Barbaloin, Hypericin), Capsaicin, Piperine, Chlorophyll, Betaine, Pectin, Oxalic Acid, Acetyl-L-Carnitine, Allantoin, Androsterondiol, Androsterondione, Betaine (Trimethylglycine), Caffeine, Calcium pyvurate (Pyruvic Acid), Carnitine, Carnosine, Carotene (alpha & beta), Carotenoid (Total for beadlets), Choline, Chlorogenic Acid, Cholic Acid (Ox Bile), Chondroitin Sulfate, Chondroitin Sulfate (Total Mucopolysaccharides), Cholestin, Chrysin, Coenzyme Q10 (Co-Q10), Conjugated Linoleic Acid (CLA), Corosolic Acid, Creatine, Dehydroepiandrosterone (DHEA), Dichlorophen, Diindolymethane (DIM), Dimethyglycine (DMG), Dimercapto Succinic Acid (DMSA), Ebselen, Ellagic Acid, Enzymes, Fisetin, Formonetin, Glucaric Acid (Glucarate), Glucosamine (HCl or Sulfate), Glucosamine (N-Acetyl), Glutathione (Reduced), Hesperidine, Hydroxy-3-Methylbutyric Acid (HMB), 5-Hydroxytryptophan (L-5-HTP), Indole-3-Carbinol, Inositol, Isothiocyanates, Linolenic Acid-Gamma (GLA), Lipoic Acid (alpha), Melatonin, Methylsulfonylmethane (MSM), Minerals, Naringin, Pancreatin, Para-aminobenzoic Acid (PABA), Paraben (methyl or propyl), Phenolics, Phosphatidylcholine (Lecithin), Phosphatidylserine, Phospholipids, Phytosterols, Pregersterone, Pregnenolone, Quercetin, Resveratrol, D-Ribose, Rutin, S-adenosylmethionine (SAM-e), Salicylic Acid, Sulforaphane, Tartaric Acid, Taxifolin, Tetrahydropalmatine, Thephyline, Theobromine, Tigogenin, Troxerutin, Tryptophan, Tocotrienol (alph, beta & gamma), Vitamins, Zeaxanthin, Gingo Biloba, Ginger, Cat's Claw, *Hypericum*, Aloe Vera, Evening Primrose, Garlic, *Capsicum*, Dong Quai, Ginseng, Feverview, Fenugreek, Echinacea, Green Tea, Marshmallow, Saw Palmetto, Tea Tree Oil, Payllium, Kava-Kava, Licorice Root, Manonia Aquifolium, Hawthorne, Hohimbr, Tumeric, Witch Hazel, Valerian, Mistletoe, Bilberry, Bee Pollen, Peppermint Oil, Beta-Carotene, Genistein, Lutein, Lycopene, the Polyphenols (bioflavonoids), and the like.

In some embodiments, nutraceutical agents 118 may include microbes (i.e., probiotics). Examples of such microbes include, but are not limited to, *Lactobacillus acidophilus, Lactobacillus plantarum, Lactobacillus casei, Bifidobacterium bifidum, Bifidobacterium longum, Saccharomyces boulardii, Saccharomyces cerevisiae*, and the like (i.e., Samuel and Gordon, A humanized gnotobiotic mouse model of host-archaeal-bacterial mutualism, PNAS, 103(26):10011-10016 (2006)). In some embodiments, nutraceutical agents 118 may include non-living microbes. For example, non-living *Saccharomyces cerevisiae* may be used as a source of vitamin B12. In some embodiments, recombinant microbes may be utilized as nutraceutical agents 118. For example, in some embodiments, microbes may be genetically modified to produce, or overexpress, one or more nutraceutical agents 118.

Indicating Unit 120

The system 100 can include one or more indicating units 120. In some embodiments, one or more indicating units 120 can be used to indicate one or more dosages 122 of one or more nutraceutical agents 118 in response to selecting one or more nutraceutical agents 118 in response to intaking information 112 linked to one or more parameters 114 associated with one or more specified goals 106 of an individual 108. In some embodiments, one or more indicating units 120 indicate one or more dosages 122 of one or more nutraceutical agents 118 in human-readable format. In some embodiments, one or more indicating units 120 indicate one or more dosages 122 of one or more nutraceutical agents 118 in machine-readable format. In some embodiments, one or more indicating units 120 deposit one or more dosages 122 of one or more nutraceutical agents 118 on one or more labels. In some embodiments, one or more indicating units 120 dispense one or more nutraceutical agents 118. In some embodiments, one or more indicating units 120 dispense one or more nutraceutical agents 118 in unit dosage form. In some embodiments, one or more indicating units 120 dispense two or more nutraceutical agents 118 in a single administration form. In some embodiments, one or more indicating units 120 can be included within system 100 through use of a hardwired connection. In some embodiments, one or more indicating units 120 can be included within system 100 through use of a wireless connection. In some embodiments, one or more indicating units 120 can be included within system 100 through use of a hardwired and a wireless connection.

Dosage 122

Dosages 122 may be expressed in numerous ways. In some embodiments, a dosage 122 may be expressed as an absolute quantity (i.e., 500 milligrams of a nutraceutical agent 118). In other embodiments, a dosage 122 may be expressed in accordance with the body weight of an individual 108 (i.e., 10 milligram nutraceutical agent 118 per kilogram body weight). In some embodiments, a dosage 122 may be expressed as a range of quantities (i.e., 10 milligrams to 100 milligrams of a nutraceutical agent 118). In some embodiments, a dosage 122 may be an amount of a nutraceutical agent 118 that produces a desired response when administered to a specific individual 108. For example, a dosage 122 of melatonin may be the amount of melatonin that induces sleep in a specific individual 108. The dosage 122 of a nutraceutical agent 118 may vary according to numerous considerations that include, but are not limited to, the route of administration, the age of the individual 108, the size of the individual 108, the metabolic characteristics of the individual 108, the condition of the individual 108, and the like. In some embodiments, the dosage 122 of a nutraceutical agent 118 may be determined that produces a measurable effect, such as a physical effect, a psychological effect, a physiological effect, and the like. Accordingly, in some embodiments, a dosage 122 may be expressed as an amount of a nutraceutical agent 118 that produces a mental response in an individual 108. For example, in some embodiments, a dosage 122 may be the amount of a nutraceutical agent 118 that produces a sensation of well-being when administered to an individual 108. In other embodiments, a dosage 122 may be the amount of a nutraceutical agent 118 that elevates the mood of an individual 108 to whom the nutraceutical is to be administered. Numerous additional criteria may be used to determine the dosage 122 of a nutraceutical for administration to an individual 108.

In some embodiments, one or more indicating units 120 can indicate one or more dosages 122 of one or more nutraceutical agents 118 and one or more formulations of the one or more nutraceutical agents 118. For example, in some embodiments, one or more indicating units 120 may indicate a formulation and dosage 122 of chromium. Presently, the most widely available chromium supplements are chromium salts such as chromium polynicotinate, chromium picolinate, and various chromium/amino acid chelates. Such formulations help increase the absorption and availability of chromium when compared to isolated chromium salts such as chromium chloride. The estimated safe and adequate daily dietary intake of chromium is 50-200 micrograms. Natural forms of supplemental chromium, such as chromium-rich yeast, may be absorbed somewhat more efficiently than inorganic forms of chromium, such as chromium chloride, found in some supplements. One ounce of brewer's yeast provides approximately 100-200 micrograms of chromium. Accordingly, in some embodiments, one or more indicating units 120 may indicate a dosage 122 of chromium and a corresponding formulation of the chromium. In another embodiment, one or more indicating units 120 may indicate a dosage 122 of vitamin A. For vitamin A deficiency syndromes, vitamin A may be orally supplemented at a dosage 122 of 600 micrograms for children aged 3 years or younger, 900 micrograms for children aged 4-8 years, 1700 micrograms for children aged 9-13 years, 2800 micrograms for persons aged 14-18 years, and 3000 micrograms for all adults. Therapeutic doses for severe disease include 60,000 micrograms, which has been shown to reduce child mortality rates by 35-70%. One or more indicating units 120 may indicate dosages 122 for numerous types of nutraceutical agents 118 that are formulated in numerous ways.

Transmitting Unit 128

The system 100 can include one or more transmitting units 128. In some embodiments, one or more transmitting units 128 can be used to transmit one or more signals 130 in response to intaking information 112 linked to one or more parameters 114 associated with one or more specified goals 106 of an individual 108. In some embodiments, one or more transmitting units 128 can be used to transmit one or more levels of one or more metabolic indicators linked to an individual 108. In some embodiments, one or more transmitting units 128 can be used to transmit one or more levels of one or more metabolic activities linked to an individual 108. In some embodiments, one or more transmitting units 128 can be used to transmit one or more levels of one or more nutraceutical agents 118 linked to an individual 108. In some embodiments, one or more transmitting units 128 can be used to transmit one or more levels of one or more pharmaceutical agents linked to an individual 108. In some embodiments, one or more transmitting units 128 can be used to transmit one or more parameters 114 associated with one or more specified goals 106 of an individual 108. In some embodiments, one or more transmitting units 128 can be used to transmit one or more instructions to select one or more nutraceutical agents 118 in response to intaking information 112 linked to one or more parameters 114 associated with one or more specified goals 106 of an individual 108. In some embodiments, one or more transmitting units 128 can be used to transmit one or more signals 130 to select one or more nutraceutical agents 118 to increase one or more levels of one or more components associated with one or more specified goals 106 of an individual 108. In some embodiments, one or more transmitting units 128 can be used to transmit one or more signals 130 to select one or more nutraceutical agents 118 to decrease one or more levels of one or more components associated with one or more specified goals 106 of an individual 108. In some embodiments, one or more transmitting units 128 can be used to transmit one or more signals 130 to select one or more nutraceutical agents 118 that stimulate one or more metabolic pathways linked to an individual 108. In some embodiments, one or more transmitting units 128 can be used to transmit one or more signals 130 to select one or more nutraceutical agents 118 that inhibit one or more metabolic pathways linked to an individual 108. In some embodiments, one or more transmitting units 128 can be used to transmit one or more signals 130 to select at least one vitamin, mineral, enzyme, amino acid, homeopathic supplement, toxin, homeopathic substance, traditional remedy, herbal supplement, glandular supplement, or substantially any combination thereof. In some embodiments, one or more transmitting units 128 can be included within system 100 through use of a hardwired connection. In some embodiments, one or more transmitting units 128 can be included within system 100 through use of a wireless connection. In some embodiments, one or more transmitting units 128 can be included within system 100 through use of a hardwired and a wireless connection.

Signal 130

The system 100 may include one or more signals 130. Numerous types of signals 130 may be transmitted. Examples of such signals 130 include, but are not limited to, hardwired signals 130, wireless signals 130, infrared signals 130, optical signals 130, radiofrequency (RF) signals 130, audible signals 130, digital signals 130, analog signals 130, or substantially any combination thereof.

Receiving Unit 132

The system 100 may include one or more receiving units 132. In some embodiments, one or more receiving units 132 receive one or more signals 130 transmitted in response to intaking information 112 linked to one or more parameters 114 associated with one or more specified goals 106 of an individual 108. In some embodiments, one or more receiving units 132 receive one or more signals 130 indicating one or more levels of one or more metabolic indicators linked to an individual 108. In some embodiments, one or more receiving units 132 receive one or more signals 130 indicating one or more metabolic activities linked to an individual 108. In some embodiments, one or more receiving units 132 receive one or more signals 130 indicating one or more levels of one or more nutraceutical agents 118 linked to an individual 108. In some embodiments, one or more receiving units 132 receive one or more signals 130 indicating one or more levels of one or more pharmaceutical agents linked to an individual 108. In some embodiments, one or more receiving units 132 receive one or more parameters 114 associated with one or more specified goals 106 of an individual 108. In some embodiments, one or more receiving units 132 receive one or more instructions to select one or more nutraceutical agents 118 in response to intaking information 112 linked to one or more parameters 114 associated with the one or more specified goals 106 of the individual 108. In some embodiments, one or more receiving units 132 receive one or more signals 130 to select one or more nutraceutical agents 118 to increase one or more levels of one or more components associated with one or more specified goals 106 of an individual 108. In some embodiments, one or more receiving units 132 receive one or more signals 130 to select one or more nutraceutical agents 118 to decrease one or more levels of one or more components associated with one or more specified goals 106 of an individual 108. In some embodiments, one or more receiving units 132 receive one or more signals 130 to select one or more nutraceutical agents 118 that stimulate one or more metabolic pathways linked to an individual 108. In some embodiments, one or more receiving units 132 receive one or more signals 130 to select one or more nutraceutical agents 118 that inhibit one or more metabolic pathways linked to an individual 108. In some embodiments, one or more receiving units 132 receive one or more signals 130 to select at least one vitamin, mineral, enzyme, amino acid, homeopathic supplement, toxin, homeopathic substance, traditional remedy, herbal supplement, glandular supplement, or substantially any combination thereof.

Receiving units 132 may receive numerous types of signals 130. Examples of such signals 130 include, but are not limited to, hardwired signals 130, wireless signals 130, infrared signals 130, optical signals 130, radiofrequency (RF) signals 130, auditory signals 130, digital signals 130, analog signals 130, or substantially any combination thereof.

Recording Unit 124

The system 100 may include one or more recording units 124. In some embodiments, one or more recording units 124 can communicate with one or more accepting units 102, one or more intaking units 110, one or more transmitting units 128, one or more receiving units 132, one or more selecting units 116, one or more indicating units 120, one or more users 136, and/or substantially any combination thereof. Many types of recording units 124 may be used within system 100. Examples of such recording devices include those that utilize a recordable medium 126 that includes, but is not limited to, many types of memory, optical disks, magnetic disks, magnetic tape, and the like.

User Interaction 134/User 136

The system 100 may provide for user interaction 134. In some embodiments, a user 136 may interact with one or more accepting units 102, one or more intaking units 110, one or more transmitting units 128, one or more receiving units 132, one or more selecting units 116, one or more indicating units 120, one or more recording units 124, and/or substantially any combination thereof. The user 136 can interact through use of numerous technologies. For example, user interaction 134 can occur through use of hardwired methods, such as through use of a keyboard, use of wireless methods, use of the internet, and the like. In some embodiments, a user 136 is a health-care worker. Examples of such health-care workers include, but are not limited to, physicians, nurses, dieticians, pharmacists, and the like. In some embodiments, users 136 may include those persons who work in health-related fields, such as coaches, personal trainers, clerks at food supplement stores, clerks at grocery stores, and the like. In some embodiments, a user 136 is not human.

Figure 2:
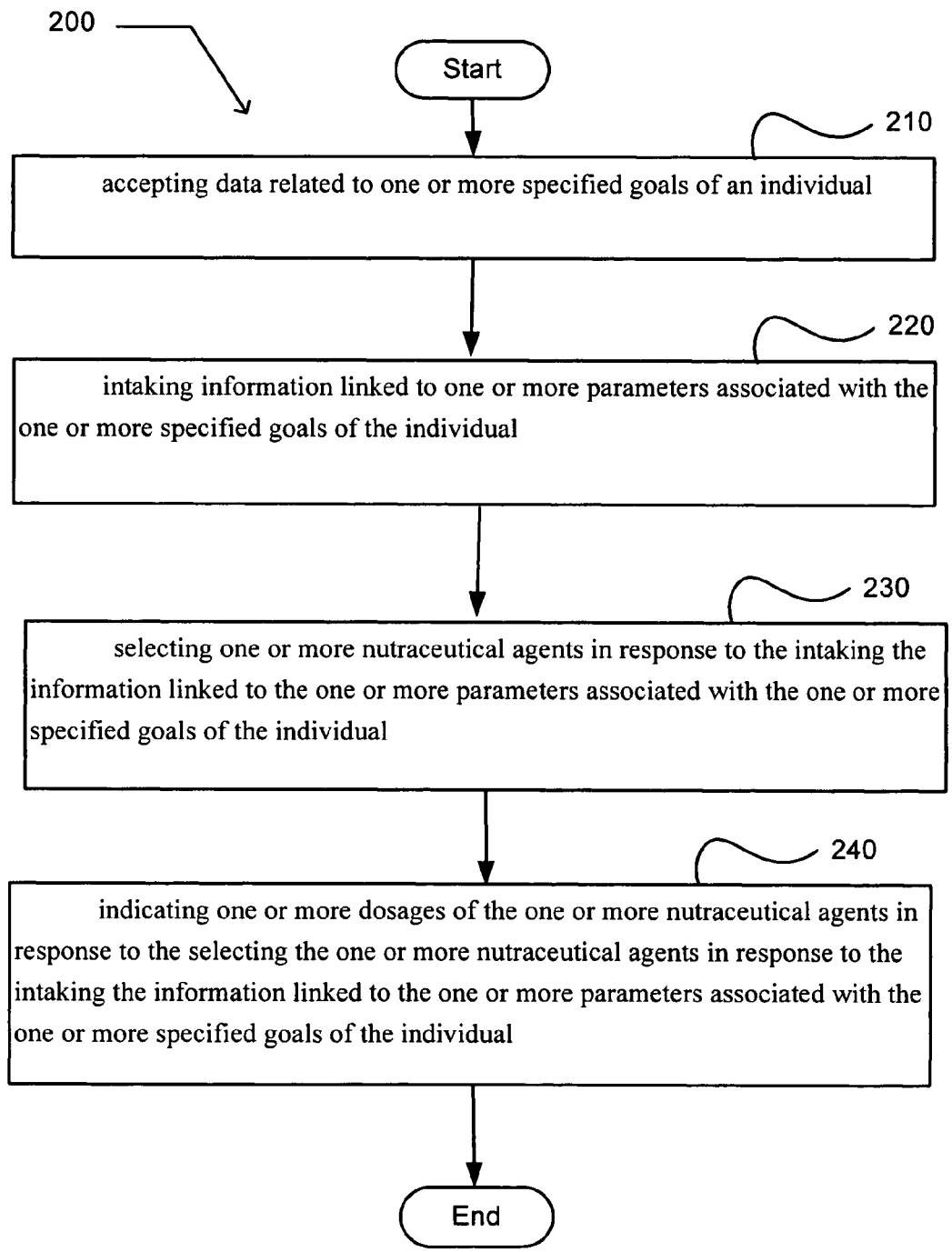
FIG. 2 illustrates an operational flow 200 representing example operations related to methods for nutraceutical agent selection and dosing.

FIG. 2 illustrates an operational flow 200 representing examples of operations that are related to the performance of a method for nutraceutical agent 118 and dosing. In FIG. 2 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 200 includes an accepting operation 210 involving accepting data related to one or more specified goals of an individual. In some embodiments, one or more accepting units 102 may accept data 104 related to one or more specified goals 106 of an individual 108. The one or more specified goals 106 may be virtually any goal to be achieved, or attempted by, an individual 108 that may be affected by administration of one or more nutraceutical agents 118 to the individual 108. In some embodiments, administration of one or more nutraceutical agents 118 to an individual 108 may assist the individual 108 to achieve one or more specified goals 106. In some embodiments, administration of one or more nutraceutical agents 118 to an individual 108 may stimulate the individual 108 to achieve one or more specified goals 106. In some embodiments, administration of one or more nutraceutical agents 118 to an individual 108 may reduce an inhibition coupled to the individual 108 to promote achieving one or more specified goals 106 by the individual 108. Numerous examples of specified goals 106 of an individual 108 exist. In some embodiments, specified goals 106 of an individual 108 may be related to attentiveness, alertness, test performance, relaxation, pain, fever, attractiveness, anxiety, fall, injury, accident, bite, bleeding, inflammation, infection, drowsiness, insomnia, discomfort, stress, grooming, appearance, capability, performance, improvement, enhancement, curtailment, wellbeing, vitality, vigor, disability, phobia, malady, psychosis, environmental extremes, environmental exposure, dysfunction, disease symptom, chronic condition, mental acuity, emotional behavior, physical prowess, addiction, obsession, therapy, remedy, behavior, nutrition, diet, exercise, immunization, prevention, diagnosis, subscription, regimen, social performance, social interaction, endurance, sexual attribute, sexual performance, age-related attribute, age-related condition, prophylaxis, treatment, and substantially any combination thereof. In some embodiments, data 104 may include identification of one or more of the specified goals 106 of an individual 108. In some embodiments, data 104 may include characteristics of an individual 108. Examples of such data 104 may include, but are not limited to, physical characteristics, metabolic characteristics, financial characteristics, and the like. In some embodiments, data 104 may include, an individual's 108 height, weight, gender, kidney function, liver function, level of physical fitness, age, allergic response, metabolic level (i.e., resting metabolic rate and/or activity-related metabolic rate), disease state, body fat percentage, body mass index, personal health habits (i.e., smoking, alcohol consumption, diet, illegal drug use, and the like), family health history, insurance coverage, food supplement usage, nutraceutical agent 118 usage, non-prescription drug use, prescription drug use, pregnancy status, and the like. In some embodiments, the one or more characteristics may be specifically associated with an individual 108. As such, in some embodiments, the one or more characteristics may be unique to the individual 108 as opposed to being common to a group. For example, in some embodiments, an individual 108 may be a member of a group of persons who are diabetic while exhibiting one or more characteristics, such as metabolic characteristics, that are unique to the individual 108. Accordingly, in some embodiments, data 104 may be input that provides for selection of nutraceutical agents 118 in accordance with one or more characteristics and specified goals 106 of an individual 108.

The operational flow 200 includes an intaking operation 220 involving intaking information linked to one or more parameters associated with the one or more specified goals of the individual. In some embodiments, one or more intaking units 110 may intake information 112 linked to one or more parameters 114 associated with the one or more specified goals 106 of the individual 108. Numerous parameters 114 may be associated with one or more specified goals 106 of an individual 108. Examples of such parameters 114 include, but are not limited to, blood sugar levels, blood insulin levels, blood iron levels, hormone levels (amine-derived hormones: such as catecholamines (adrenaline, dopamine, noradrenaline); tryptophan derivatives (melatonin, serotonin); tyrosine derivatives (thyroxine and triiodothyronine); peptide hormones such as antimullerian hormone, adiponectin, adrenocorticotropic hormone, angiotensinogen and angiotensin, antidiuretic hormone, atrial-natriuretic peptide, calcitonin, cholecystokinin, corticotropin-releasing hormone, erythropoietin, follicle-stimulating hormone, gastrin, ghrelin, glucagons, gonadotropin-releasing hormone, growth hormone-releasing hormone, human chorionic gonadotropin, growth hormone, inhibin, insulin, insulin-like growth factor, luteinizing hormone, melanocyte stimulating hormone, neuropeptide Y, oxytocin, parathyroid hormone, prolactin, relaxin, secretin, somatostatin, thrombopoietin, thyroid-stimulating hormone, thyrotropin-releasing hormone; steroid hormones: Glucocorticoids (cortisol); Mineralocorticoids (aldosterone); sex steroids: androgens (testosterone, dehydroepiandrosterone, dehydroepiandrosterone sulfate, androstenedione, dihydrotestosterone); estrogens (estradiol); progestagens (progesterone and progestins); sterol hormones: vitamin D derivatives (calcitriol); lipid hormones (prostaglandins, leukotrienes, prostacyclin, and thromboxane)), nutraceutical agent 118 levels, pharmaceutical agent levels, cytokine levels, and the like (i.e., Fitzgerald et al., The Cytokine Facts Book, Academic Press, San Francisco, Second Edition, (2001)). Methods to gain information 112 with regard to components of biological systems are known (i.e., Clinical Laboratory Medicine, Lippincott Williams and Wilkins, Philadelphia, Second Edition, 2002). In some embodiments, one or more intaking units 110 may include instrumentation that provides for analysis of a sample obtained from an individual 108. For example, in some embodiments, an intaking unit 110 may be configured to intake a blood sample obtained from an individual 108 and analyze the blood sample to determine one or more parameters 114 associated with one or more specified goals 106 of an individual 108 (i.e., determine the level of free testosterone or the level of melatonin in a blood sample obtained from an individual 108). Numerous analytical technologies are known and may be included within one or more intaking units 110. Examples of such technologies include, but are not limited to, gas chromatography, mass spectrometry, atomic absorption, immunoassay based methods, microfluidic based methods, spectrophotometry (i.e., infrared, ultraviolet, fluorescence, and the like), surface plasmon resonance, fluorescence resonance energy transfer, and the like. In some embodiments, one or more intaking units 110 may intake information 112 linked to one or more parameters 114 associated with the one or more specified goals 106 of an individual 108 from a source that is independent of the one or more intaking units 110. In some embodiments, one or more intaking units 110 may intake information 112 linked to one or more parameters 114 associated with the one or more specified goals 106 of an individual 108 from a source that is coupled to the one or more intaking units 110.

The operational flow 200 includes a selecting operation 230 involving selecting one or more nutraceutical agents in response to the intaking the information linked to the one or more parameters associated with the one or more specified goals of the individual. In some embodiments, one or more selecting units 116 may select one or more nutraceutical agents 118 in response to the intaking information 112 linked to one or more parameters 114 associated with the one or more specified goals 106 of the individual 108. In some embodiments, one or more selecting units 116 may select one or more nutraceutical agents 118 in response to one or more intaking units 110. In some embodiments, one or more selecting units 116 may select one or more nutraceutical agents 118 in response to one or more accepting units 102. In some embodiments, one or more selecting units 116 may select one or more nutraceutical agents 118 in response to one or more intaking units 110 and one or more accepting units 102. Accordingly, in some embodiments, one or more selecting units 116 may select one or more nutraceutical agents 118 with regard to one or more characteristics of the individual 108 and one or more parameters 114 associated with one or more specified goals 106 of the individual 108. For example, in some embodiments, one or more selecting units 116 may select one or more nutraceutical agents 118 based on the age of the individual 108 and the level of testosterone in the individual's 108 blood. In other embodiments, one or more selecting units 116 may select one or more nutraceutical agents 118 based on insurance coverage held by an individual 108 and a specified goal 106 of the individual 108. Accordingly, numerous combinations of information 112 and data 104 may be used by one or more selecting units 116 to select one or more nutraceutical agents 118.

The operational flow 200 includes an indicating operation 240 involving indicating one or more dosages of the one or more nutraceutical agents in response to the selecting the one or more nutraceutical agents in response to the intaking the information linked to the one or more parameters associated with the one or more specified goals of the individual. In some embodiments, one or more indicating units 120 may indicate one or more dosages 122 of the one or more nutraceutical agents 118 in response to the intaking information 112 linked to one or more parameters 114 associated with the one or more specified goals 106 of the individual 108. In some embodiments, one or more indicating units 120 may indicate one or more dosages 122 of one or more nutraceutical agents 118 in human-readable format. In some embodiments, one or more indicating units 120 may indicate one or more dosages 122 of one or more nutraceutical agents 118 in machine-readable format. In some embodiments, one or more indicating units 120 may deposit one or more dosages 122 of one or more nutraceutical agents 118 on one or more labels. In some embodiments, one or more indicating units 120 may dispense one or more nutraceutical agents 118. In some embodiments, one or more indicating units 120 may dispense one or more nutraceutical agents 118 in unit dosage form. In some embodiments, one or more indicating units 120 may dispense two or more of one or more nutraceutical agents 118 in a single administration form.

Figure 3:
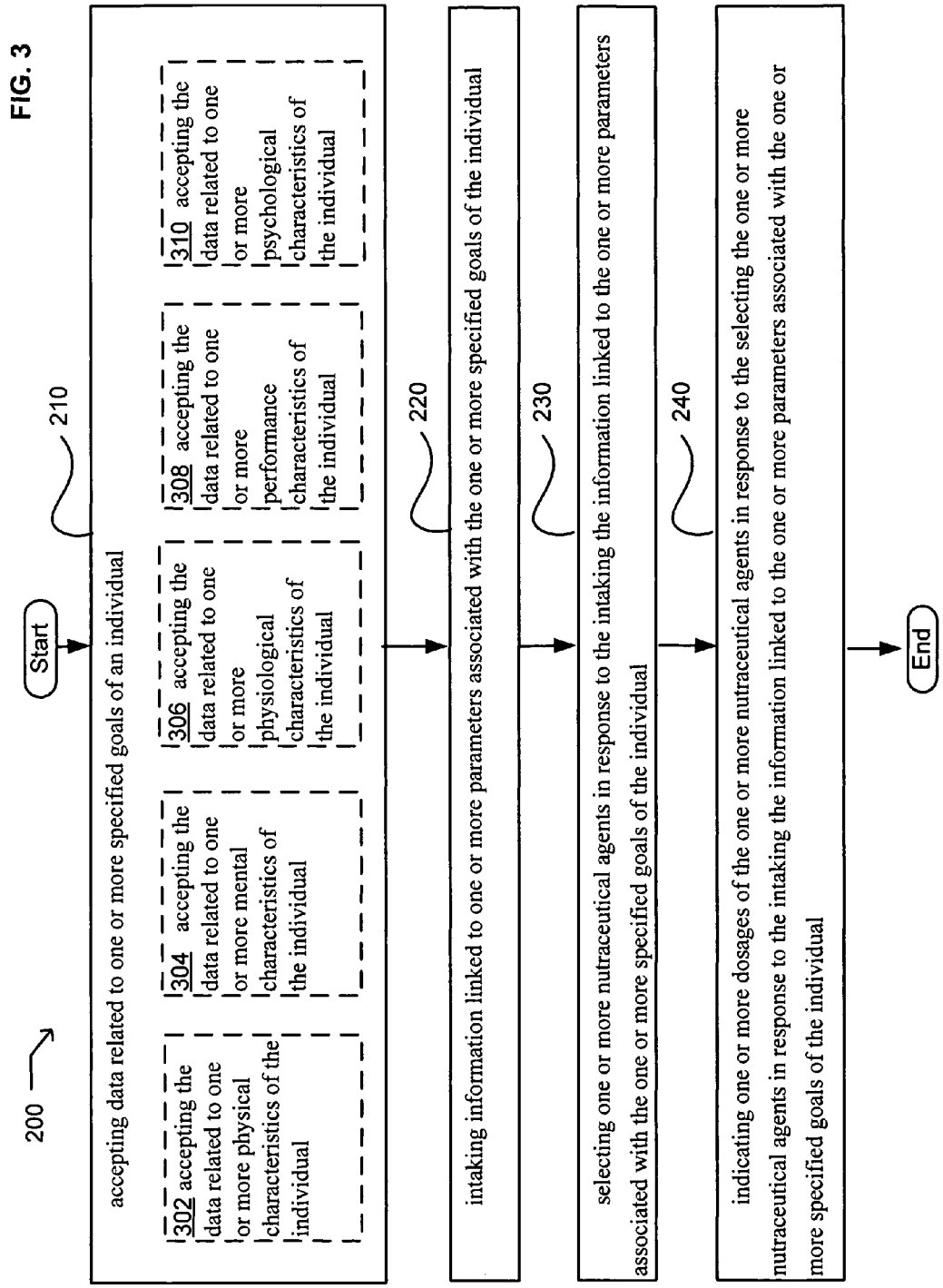
FIG. 3 illustrates alternative embodiments of the example operation flow of FIG. 2.

FIG. 3 illustrates alternative embodiments of the example operational flow 200 of FIG. 2. FIG. 3 illustrates example embodiments where the accepting operation 210 may include at least one additional operation. Additional operations may include an operation 302, an operation 304, an operation 306, an operation 308, and/or an operation 310.

At operation 302, the accepting operation 210 may include accepting the data related to one or more physical characteristics of the individual. In some embodiments, one or more accepting units 102 accept data 104 related to one or more physical characteristics of the individual 108.

One or more accepting units 102 may accept data 104 related to numerous physical characteristics of an individual 108. Examples of such physical characteristics include, but are not limited to, height, weight, gender, kidney function, liver function, level of physical fitness, age, allergic response, metabolic level (i.e., resting metabolic rate and/or activity-related metabolic rate), disease state, body fat percentage, body mass index, personal health habits (i.e., smoking, alcohol consumption, diet, illegal drug use, and the like), family health history, food supplement usage, nutraceutical agent 118 usage, non-prescription drug use, prescription drug use, pregnancy status, and the like. In some embodiments, such data 104 may be used to identify one or more nutraceutical agents 118 that are compatible with an individual 108. For example, if an individual 108 is taking a selective serotonin reuptake inhibitor (SSRI), one or more nutraceutical agents 118 should not be selected that would interfere with the serotonin reuptake inhibitor.

At operation 304, the accepting operation 210 may include accepting the data related to one or more mental characteristics of the individual. In some embodiments, one or more accepting units 102 accept data 104 related to one or more mental characteristics of the individual 108.

One or more accepting units 102 may accept data 104 related to numerous mental characteristics of an individual 108. Examples of such mental characteristics include, but are not limited to, daily time periods when the mental processes of an individual 108 are most acute or least acute (i.e., morning, afternoon, evening, night), an individual's 108 sleep schedule, an individual's 108 daily schedule of activities (i.e., meetings, presentations, travel, athletic activity), and the like.

At operation 306, the accepting operation 210 may include accepting the data related to one or more physiological characteristics of the individual. In some embodiments, one or more accepting units 102 accept data 104 related to one or more physiological characteristics of the individual 108.

One or more accepting units 102 may accept data 104 related to numerous physiological characteristics of an individual 108. Examples of such physiological characteristics include, but are not limited to, the ability of an individual 108 to metabolize one or more nutraceutical agents 118, the ability of an individual 108 to metabolize one or more pharmaceutical agents, the response of an individual 108 to one or more pharmaceutical agents, the response of an individual 108 to one or more nutraceutical agents 118, the concentration or level of one or more metabolites in one or more samples obtained from an individual 108, the concentration or level of one or more components of a sample obtained from an individual 108 that include, but are not limited to, concentrations or levels of: vitamins, minerals, metals, proteins, one or more hormones, hemoglobin, one or more neurotransmitters, metabolites, proteolytic products, antibodies, white blood cells, red blood cells, enzyme activities, lipids, lipoproteins, carbohydrates, phosphates, tumor markers, bacteria, fungi, viruses, parasites, and the like.

At operation 308, the accepting operation 210 may include accepting the data related to one or more performance characteristics of the individual. In some embodiments, one or more accepting units 102 accept data 104 related to one or more performance characteristics of the individual 108.

One or more accepting units 102 may accept data 104 related to numerous performance characteristics of an individual 108. Generally, performance characteristics relate to physical or mental activities in which an individual 108 engages. Examples of such performance characteristics include, but are not limited to, athletic ability, mental ability, sexual ability, ability to interact socially, and the like. For example, in some embodiments, data 104 related to giving a presentation may be accepted.

At operation 310, the accepting operation 210 may include accepting the data related to one or more psychological characteristics of the individual. In some embodiments, one or more accepting units 102 accept data 104 related to one or more psychological characteristics of the individual 108.

One or more accepting units 102 may accept data 104 related to numerous psychological characteristics of an individual 108. Examples of such psychological characteristics include, but are not limited to, the presence or absence of a psychological malady. Examples of psychological maladies include, but are not limited to, antisocial personal disorder, anxiety disorder, avoidant personality disorder, bipolar disorder, conduct disorder, depression, depressive disorder, drug addiction, insomnia, primary sleep disorders, schizophrenia, seasonal affective disorder, sexual disorder, sexual dysfunctions, social anxiety disorder, specific phobia, and the like.

Figure 4:
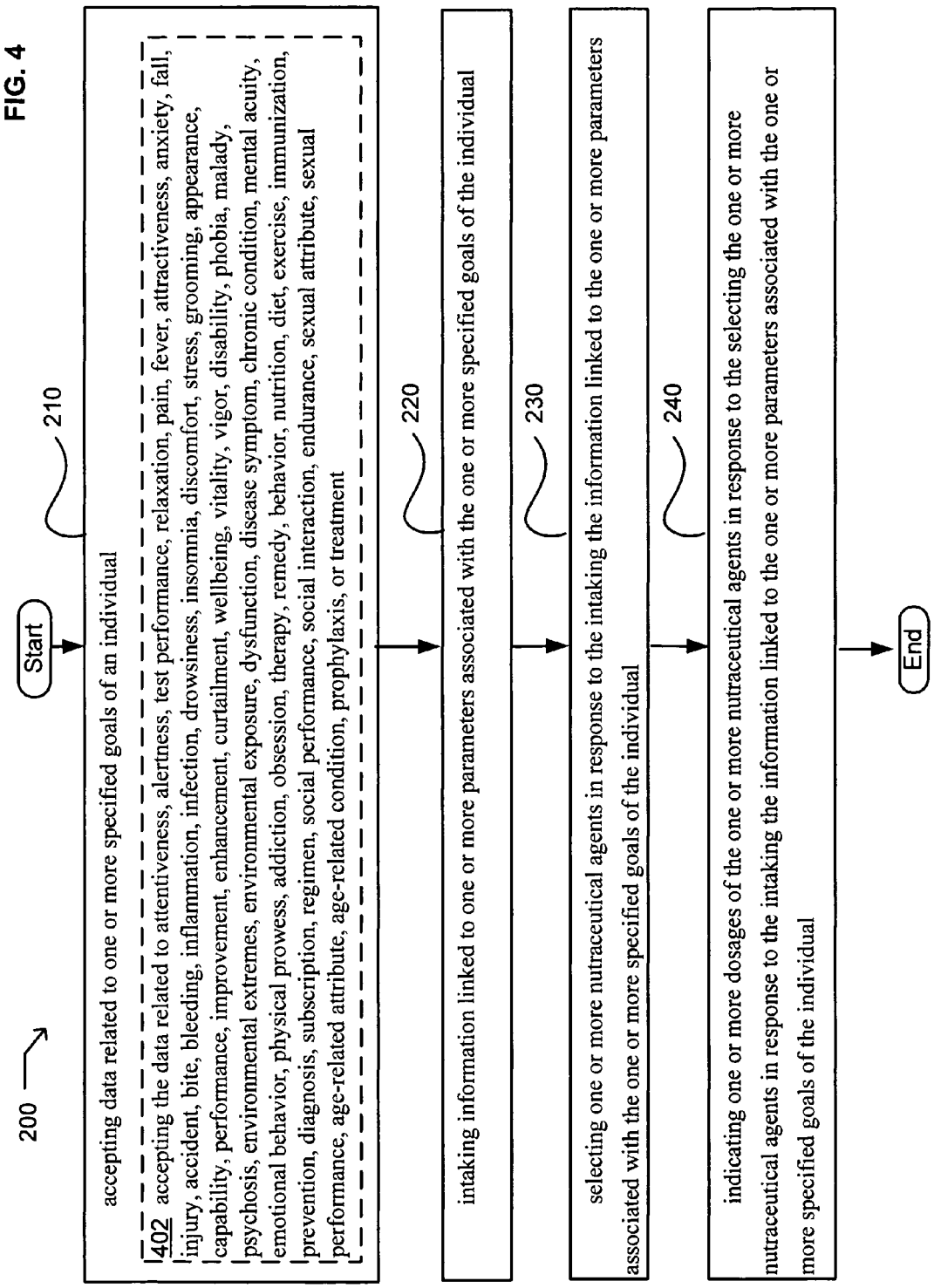
FIG. 4 illustrates alternative embodiments of the example operation flow of FIG. 2.

FIG. 4 illustrates alternative embodiments of the example operational flow 200 of FIG. 2. FIG. 4 illustrates example embodiments where the accepting operation 210 may include at least one additional operation 402.

At operation 402, the accepting operation 210 may include accepting the data related to attentiveness, alertness, test performance, relaxation, pain, fever, attractiveness, anxiety, fall, injury, accident, bite, bleeding, inflammation, infection, drowsiness, insomnia, discomfort, stress, grooming, appearance, capability, performance, improvement, enhancement, curtailment, wellbeing, vitality, vigor, disability, phobia, malady, psychosis, environmental extremes, environmental exposure, dysfunction, disease symptom, chronic condition, mental acuity, emotional behavior, physical prowess, addiction, obsession, therapy, remedy, behavior, nutrition, diet, exercise, immunization, prevention, diagnosis, subscription, regimen, social performance, social interaction, endurance, sexual attribute, sexual performance, age-related attribute, age-related condition, prophylaxis, or treatment. In some embodiments, one or more accepting units 102 accept data 104 related to attentiveness, alertness, test performance, relaxation, pain, fever, attractiveness, anxiety, fall, injury, accident, bite, bleeding, inflammation, infection, drowsiness, insomnia, discomfort, stress, grooming, appearance, capability, performance, improvement, enhancement, curtailment, wellbeing, vitality, vigor, disability, phobia, malady, psychosis, environmental extremes, environmental exposure, dysfunction, disease symptom, chronic condition, mental acuity, emotional behavior, physical prowess, addiction, obsession, therapy, remedy, behavior, nutrition, diet, exercise, immunization, prevention, diagnosis, subscription, regimen, social performance, social interaction, endurance, sexual attribute, sexual performance, age-related attribute, age-related condition, prophylaxis, or treatment.

Figure 5:
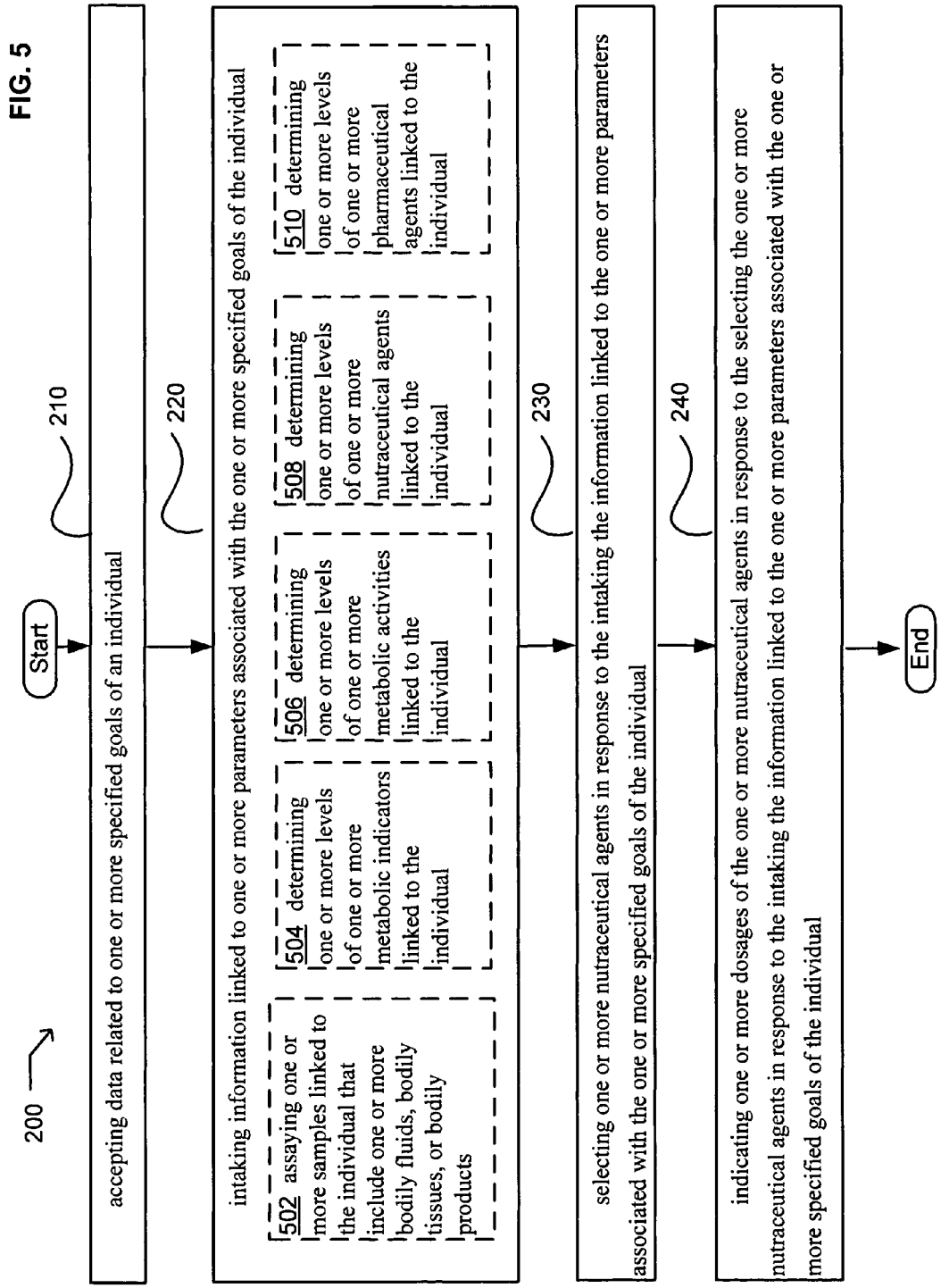
FIG. 5 illustrates alternative embodiments of the example operation flow of FIG. 2.

FIG. 5 illustrates alternative embodiments of the example operational flow 200 of FIG. 2. FIG. 5 illustrates example embodiments where the intaking operation 220 may include at least one additional operation. Additional operations may include an operation 502, an operation 504, an operation 506, an operation 508, and/or an operation 510.

At operation 502, the intaking operation 220 may include assaying one or more samples linked to the individual that include one or more bodily fluids, bodily tissues, or bodily products. In some embodiments, one or more intaking units 110 can assay one or more samples linked to the individual 108 that include one or more bodily fluids, bodily tissues, or bodily products. Examples of such samples include, but are not limited to, blood, urine, saliva, synovial fluid, pleural fluid, peritoneal fluid, tears, mucus, ejaculate, skin, muscle, bone, hair, teeth, nails, urine, breath, fecal material, genital products, and the like.

At operation 504, the intaking operation 220 may include determining one or more levels of one or more metabolic indicators linked to the individual. In some embodiments, one or more intaking units 110 can determine one or more levels of one or more metabolic indicators linked to the individual 108.

For example, vitamin $B_{12}$ and folate are two vitamins that have interdependent roles in nucleic acid synthesis. Deficiencies of either vitamin can cause megaloblastic anemia. Accordingly, in some embodiments, the levels of homocysteine and methylmalonic acid may be determined and used as metabolic indicators to indicate levels of vitamin $B_{12}$ and folate within an individual 108. In some embodiments, vitamin A deficiency may be assessed by determining albumin levels which are an indirect measure of vitamin A levels. In some embodiments, magnesium levels may be assessed directly. In some embodiments, magnesium levels may be assessed indirectly through analysis of insulin because magnesium deficiency results in impaired insulin secretion. Accordingly, in some embodiments, magnesium replacement may be used to restore insulin secretion. In some embodiments, fluorescent indicators may be used to determine chloride, zinc, and calcium levels as well as pH. Accordingly, numerous metabolic indicators that are linked to an individual 108 may be determined through use of known methods.

At operation 506, the intaking operation 220 may include determining one or more levels of one or more metabolic activities linked to the individual. In some embodiments, one or more intaking units 110 can determine one or more levels of one or more metabolic activities linked to the individual 108

In some embodiments, one or more intaking units 110 can be used to determine one or more enzyme activities of an individual 108. For example, when digested properly, protein supplies acidity to the blood. If an individual 108 is not able to adequately digest protein, the individual's 108 blood acquires excess alkaline reserves which must be continuously dumped via the kidneys into the urine. Accordingly, in some embodiments, blood alkalinity may be tested to assist in determining if an individual 108 is deficient in protease activity. In instances of protease deficiency, an individual 108 may wish to ingest a protease supplement to assist with digestion of protein. In some embodiments, enzyme activity may be determined directly. For example, protease activity can be measured directly through use of peptide substrates having an amino acid sequence that is recognized by a protease to be assayed. Such peptide substrates may be readily prepared or be obtained from commercial sources (i.e., Biotium, Inc., Hayward, Calif.; Biomol International Inc., Plymouth Meeting, Pa.; JPT Peptide Technologies, Inc., Springfield, Va.). In some embodiments, vitamin K deficiency exhibited by an individual 108 may be determined through measurement of Protein Induced by Vitamin K Absence (PIVKA-II) using several known methods (Widdershoven, Clin. Chem., 33(11): 2074-2078 (1987)). Examples of such methods include, but are not limited to, electrophoresis-immunofixation and enzyme immunoassay. Numerous metabolic activities of an individual 108 may be determined through use of methods that are known and that have been described (i.e., Clinical Laboratory Medicine, Lippincott Williams and Wilkins, Philadelphia, Second Edition, 2002).

At operation 508, the intaking operation 220 may include determining one or more levels of one or more nutraceutical agents linked to the individual. In some embodiments, one or more intaking units 110 can determine one or more levels of one or more nutraceutical agents 118 linked to the individual 108.

Numerous methods may be used to determine one or more nutraceutical agents 118 that are linked to an individual 108. Examples of such methods include, but are not limited to, chromatographic assay, mass spectrometry, spectrophotometry, immunological assay, and the like. These methods may be performed on numerous types of samples obtained from an individual 108 that are exemplified by bodily fluids, bodily tissues, bodily products and the like.

In some embodiments, one or more intaking units 110 may determine one or more levels of one or more nutraceutical agents 118 that administered to an individual 108 at one or more times. For example, in some embodiments, the level of a nutraceutical agent 118 at the time when administered to an individual 108, at time two hours post-administration, at time four hours post-administration, and at time six hours post-administration may be determined. Accordingly, in some embodiments, the rate at which one or more nutraceutical agents 118 are metabolized by an individual 108 may be determined. In some embodiments, the rate at which a level of a nutraceutical agent 118 is reached within an individual 108 may be determined. Numerous times and concentrations of nutraceutical agents 118 may be transmitted.

At operation 510, the intaking operation 220 may include determining one or more levels of one or more pharmaceutical agents linked to the individual. In some embodiments, one or more intaking units 110 can determine one or more levels of one or more pharmaceutical agents linked to the individual 108.

Numerous methods may be used to determine one or more pharmaceutical agents that are linked to an individual 108. Examples of such methods include, but are not limited to, chromatographic assay, mass spectrometry, spectrophotometry, immunological assay, and the like. These methods may be performed on numerous types of samples obtained from an individual 108 that are exemplified by bodily fluids, bodily tissues, bodily products and the like.

In some embodiments, one or more intaking units 110 may determine one or more levels of one or more pharmaceutical agents that administered to an individual 108 at one or more times. For example, in some embodiments, the level of a pharmaceutical agent at the time when administered to an individual 108, at time two hours post-administration, at time four hours post-administration, and at time six hours post-administration may be determined. Accordingly, in some embodiments, the rate at which one or more pharmaceutical agents are metabolized by an individual 108 may be determined. In some embodiments, the rate at which a level of a pharmaceutical agent is reached within an individual 108 may be determined. Numerous times and concentrations of pharmaceutical agents may be determined.

Figure 6:
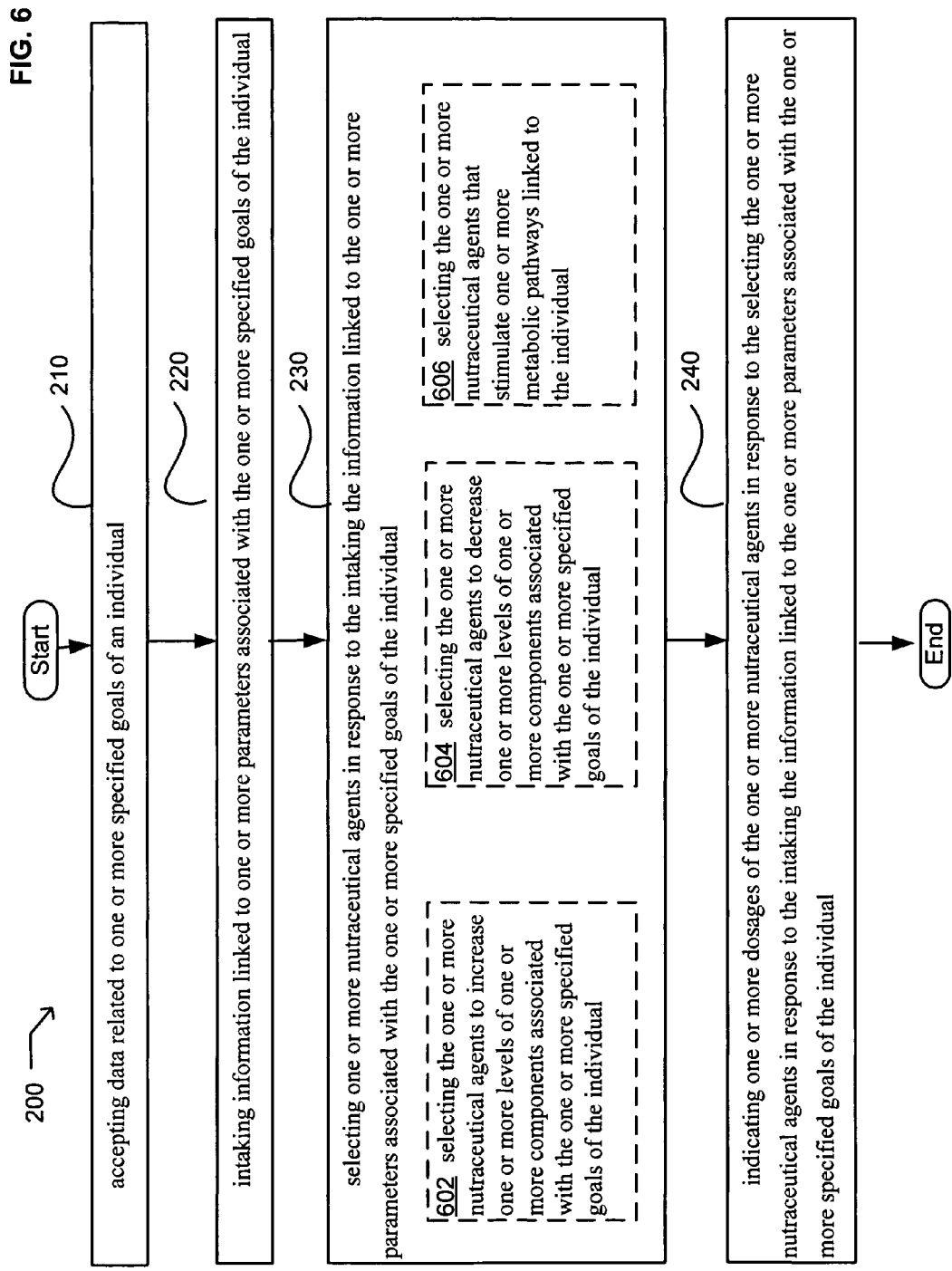
FIG. 6 illustrates alternative embodiments of the example operation flow of FIG. 2.

FIG. 6 illustrates alternative embodiments of the example operational flow 200 of FIG. 2. FIG. 6 illustrates example embodiments where the selecting operation 230 may include at least one additional operation. Additional operations may include an operation 602, an operation 604, and/or an operation 606.

At operation 602, the selecting operation 230 may include selecting the one or more nutraceutical agents to increase one or more levels of one or more components associated with the one or more specified goals of the individual. In some embodiments, one or more selecting units 116 can select one or more nutraceutical agents 118 to increase one or more levels of one or more components associated with the one or more specified goals 106 of the individual 108.

In some embodiments, one or more nutraceutical agents 118 may be selected that may directly complement one or more levels of one or more components associated with one or more specified goals 106 of the individual 108. For example, calcium in various forms (i.e., calcium citrate, calcium aspartate, calcium carbonate) may be selected by an individual 108 who wants to avoid or reduce the effects of osteoporosis. In another embodiment, chromium may be selected to lower blood sugar, increase insulin sensitivity, reduce body fat, control hunger, suppress appetite, increase lean body/muscle mass, or substantially any combination thereof. In some embodiments, one or more nutraceutical agents 118 associated with one or more specified goals 106 of an individual 108 may be selected that may be administered to an individual 108 to indirectly supplement a component associated with the one or more specified goals 106. For example, 5-hydroxy-tryptophan may be selected for administration to an individual 108 if the individual 108 suffers from depression and is found to exhibit low levels of serotonin. The 5-hydroxy-tryptophan will be converted to serotonin following administration to the individual 108. Numerous nutraceutical agents 118 may be selected to increase one or more levels of one or more components associated with one or more specified goals 106 of an individual 108.

At operation 604, the selecting operation 230 may include selecting the one or more nutraceutical agents to decrease one or more levels of one or more components associated with the one or more specified goals of the individual. In some embodiments, one or more selecting units 116 can select one or more nutraceutical agents 118 to decrease one or more levels of one or more components associated with the one or more specified goals 106 of the individual 108.

In some embodiments, one or more components may be associated with one or more specified goals 106 of an individual 108. Low density lipoproteins are examples of components that are linked to vascular disease. Accordingly, in some embodiments, one or more nutraceutical agents 118 may be selected that will act to lower the low density lipoprotein concentration of an individual 108. Examples of such nutraceutical agents 118 include, but are not limited to, plant stanols, dietary fiber, stanol esters, isoflavones, diallyl sulfides, niacin, soy protein, and substantially any combination thereof. Glucose is an example of a component that is linked to hyperglycemia. Accordingly, in some embodiments, buckwheat is an example of a nutraceutical agent 118 that may be selected to lower blood glucose levels of an individual 108. Free radical oxygen species that include singlet oxygen, hydroxyl radicals, peroxides, and superoxide radicals are components that act to damage lipids and other cellular structures. Accordingly, one or more nutraceutical agents 118 may be selected to reduce levels of free radicals within an individual 108. Examples of such nutraceutical agents 118 include, but are not limited to, terpenes, carotenoids, limonoids, phenols, flavonoids, isoprenoids, and the like. Numerous other nutraceutical agents 118 may be selected to decrease one or more levels of one or more components associated with the one or more specified goals 106 of the individual 108.

At operation 606, the selecting operation 230 may include selecting the one or more nutraceutical agents that stimulate one or more metabolic pathways linked to the individual. In some embodiments, one or more selecting units 116 can select one or more nutraceutical agents 118 that stimulate one or more metabolic pathways linked to the individual 108.

In some embodiments, stimulation of one or more metabolic pathways may be associated with one or more specified goals 106 of an individual 108. For example, in some embodiments, decline in L-carnitine synthesis is thought to be linked to senile reduction in bone synthesis (Colucci et al., Calcified Tissue International, 76:458-465 (2005)). Dihydroepiandrosterone (DHEA) is thought to affect levels of L-carnitine through promoting the expression of carnitine-synthesizing enzymes (Chiu et al., Calcified Tissue International, 64:527-533 (1999)). Accordingly, DHEA may be selected to stimulate the L-carnitine synthetic pathway to reduce senile reduction in bone synthesis. In other embodiments, buckwheat extract may be selected to lower blood glucose due to the ability of buckwheat extract to activate mitogen activated protein kinase via phospholipase D (Appleton and Lockwood, The Pharmaceutical Journal, 277:78-83 (2006)). In another embodiment, resveratrol has been shown to stimulate endothelial nitric oxide synthase activity (Klinge et al., J. Biol. Chem., 280(9):7460-7468 (2005); Wallerath et al., Circulation, 106(13):1652-1658 (2002)). Endothelial nitric oxide synthase is an enzyme that catalyzes the formation of nitric oxide by vascular endothelial cells. Nitric oxide is needed to maintain arterial relaxation (vasodilation), and impaired nitric oxide-dependent vasodilation is associated with increased risk of cardiovascular disease (Duffy and Vita, Curr. Opin. Lipidol., 14(1):21-27 (2003)). Accordingly, in some embodiments, resveratrol may be selected to reduce cardiovascular disease. Numerous nutraceutical agents 118 may be selected to one or more metabolic pathways linked to the individual 108.

Figure 7:
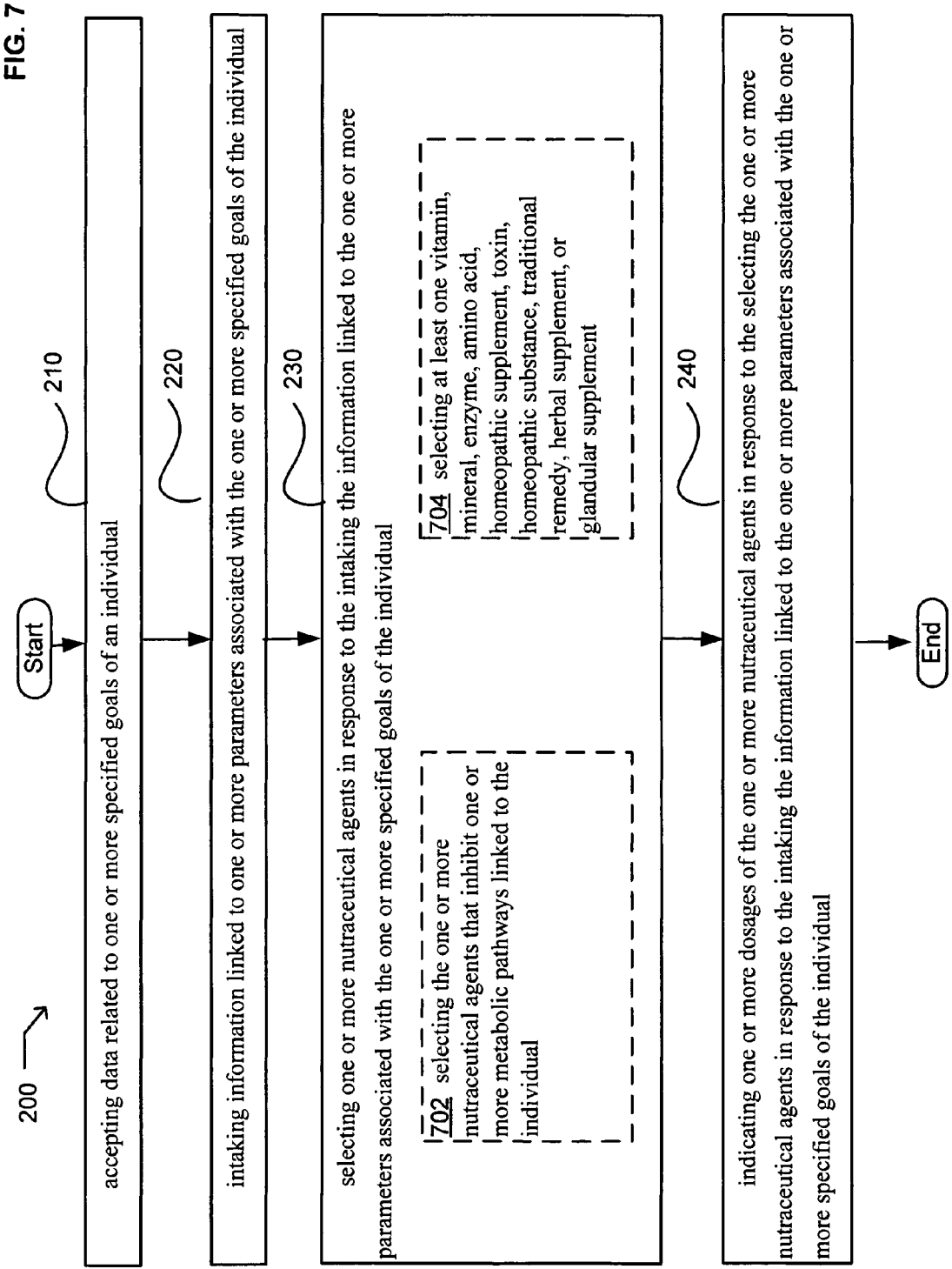
FIG. 7 illustrates alternative embodiments of the example operation flow of FIG. 2.

FIG. 7 illustrates alternative embodiments of the example operational flow 200 of FIG. 2. FIG. 7 illustrates example embodiments where the selecting operation 230 may include at least one additional operation. Additional operations may include an operation 702, and/or an operation 704.

At operation 702, the selecting operation 230 may include selecting the one or more nutraceutical agents that inhibit one or more metabolic pathways linked to the individual. In some embodiments, one or more selecting units 116 can select one or more nutraceutical agents 118 that inhibit one or more metabolic pathways linked to the individual 108.

In some embodiments, one or more metabolic pathways may be inhibited through inhibition of one or more enzymes that participate within the metabolic pathway. Such metabolic pathways may be involved with a specified goal 106 of an individual 108. For example, angiotensin-converting enzyme has been linked to high blood pressure. Flavonoids have been shown to inhibit angiotensin-converting enzyme (Actis-Goretta et al., J. Agric. Food Chem., 54(1):229-234 (2006)). Accordingly, flavonoids may be selected to assist in the reduction of blood pressure (Li et al., Chin. J. Physiol., 48(2): 101-106 (2005); Machha and Mustafa, J. Cardiovasc. Pharmacol., 46(1):36-40 (2005)). Genistein, one of the predominant soy isoflavones, has been shown to compete with 17beta-estradiol for estrogen receptor binding because of its structural similarity, resulting in agonistic or antagonistic activity. This has been shown to cause inhibition of cell growth in breast and prostate cancers in vivo and in vitro. Accordingly, soy isoflavones containing genistein may be selected as a nutraceutical agent 118 for cancer chemoprevention (Sarkar et al., Mini Rev. Med. Chem., 6(4):401-407 (2006)). The isoflavonoids, daidzin, daidzein, and puerarin have been shown to reduce alcohol consumption (Lin R C, Alcohol Clin. Exp. Res., 20(4):659-663 (1996)). A link between daidzin's capacity to reduce alcohol consumption and its ability to increase the liver mitochondrial monoamine oxidase:aldehyde dehydrogenase activity ratio has been established (Keung, Med. Res. Rev., 23(6):669-696 (2003)). This increase in ratio is thought to occur through inhibition of aldehyde dehydrogenase activity. Accordingly, isoflavonoid mixtures that include daidzin, daidzein, and/or puerarin may be selected to lower alcohol consumption. Numerous other nutraceutical agents 118 may be selected that inhibit one or more metabolic pathways linked to the individual 108.

At operation 704, the selecting operation 230 may include selecting at least one vitamin, mineral, enzyme, amino acid, homeopathic supplement, toxin, homeopathic substance, traditional remedy, herbal supplement, or glandular supplement. In some embodiments, one or more selecting units 116 can select at least one vitamin, mineral, enzyme, amino acid, homeopathic supplement, toxin, homeopathic substance, traditional remedy, herbal supplement, or glandular supplement.

Figure 8:
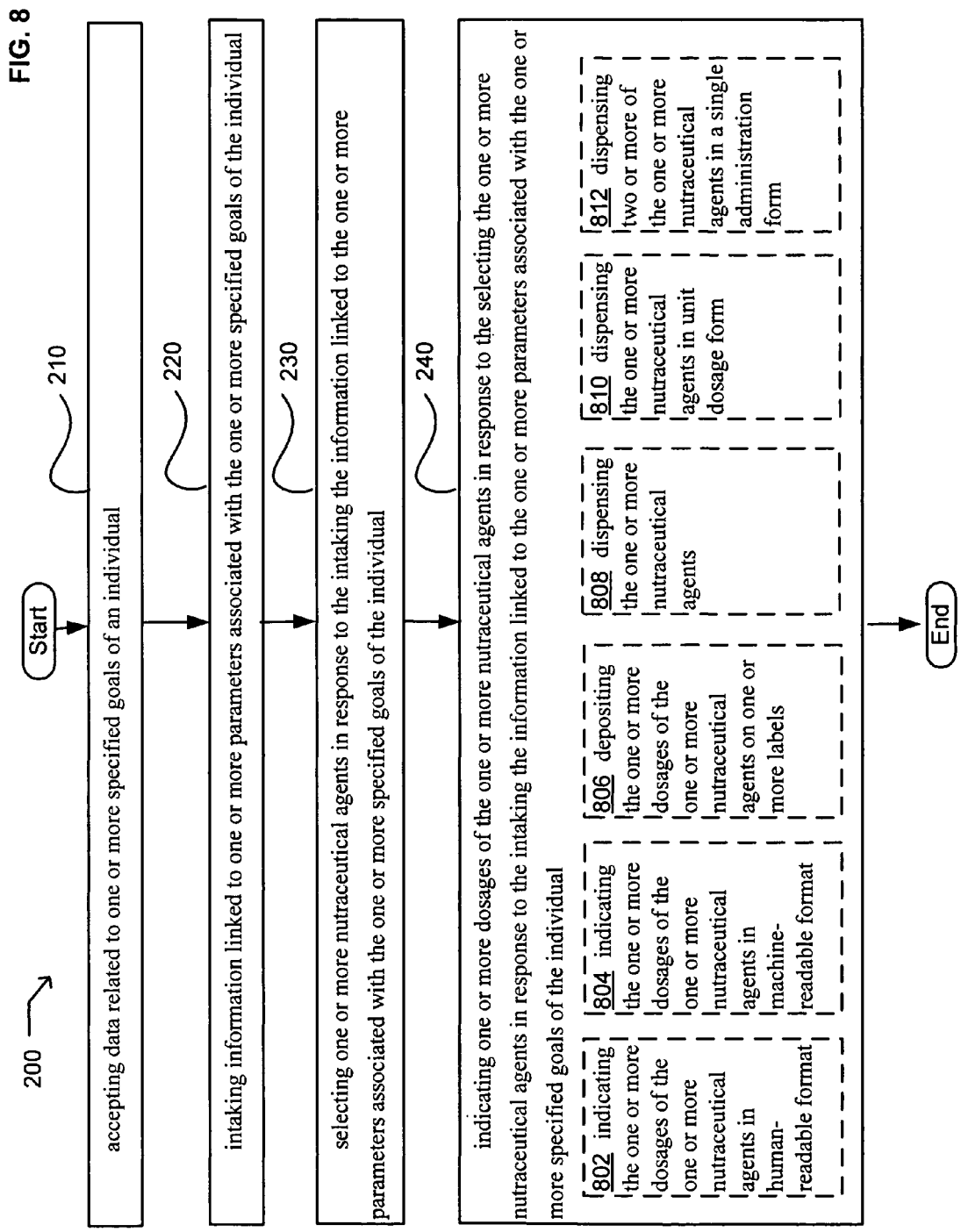
FIG. 8 illustrates alternative embodiments of the example operation flow of FIG. 2.

FIG. 8 illustrates alternative embodiments of the example operational flow 200 of FIG. 2. FIG. 8 illustrates example embodiments where the indicating operation 240 may include at least one additional operation. Additional operations may include an operation 802, an operation 804, an operation 806, an operation 808, an operation 810, and/or an operation 812.

At operation 802, the indicating operation 240 may include indicating the one or more dosages of the one or more nutraceutical agents in human-readable format. In some embodiments, one or more indicating units 120 can indicate the one or more dosages 122 of the one or more nutraceutical agents 118 in human-readable format.

In some embodiments, one or more indicating units 120 may indicate one or more dosages 122 of one or more nutraceutical agents 118 on a visual display, a touch display, an audible display, and the like. For example, in some embodiments, one or more indicating units 120 may display one or more dosages 122 on a light emitting diode display, a liquid crystal display, various monitors, and the like. Such visual displays may indicate one or more dosages 122 through display of colors, pictures, printed language, and the like. In some embodiments, one or more indicating units 120 may display one or more dosages 122 on a touch display (i.e., a touch pad display in Braille for use by blind or visually impaired persons). In some embodiments, one or more indicating units 120 may display one or more dosages 122 through use of an audible display that verbally speaks to an individual 108.

In some embodiments, one or more indicating units 120 may display one or more dosages 122 of one or more nutraceutical agents 118 in typographical symbols in numerous languages that are in human-readable format. In some embodiments, one or more indicating units 120 may display one or more dosages 122 of one or more nutraceutical agents 118 and the formulation type of the one or more nutraceutical agents 118 in typographical symbols in numerous languages that are in human-readable format. In some embodiments, one or more indicating units 120 may display one or more dosages 122 of one or more nutraceutical agents 118 in pictographic form that is in human-readable format. In some embodiments, one or more indicating units 120 may display one or more dosages 122 of one or more nutraceutical agents 118 and the formulation type of the one or more nutraceutical agents 118 in pictographic form that is in human-readable format. In some embodiments, one or more indicating units 120 may display one or more dosages 122 of one or more nutraceutical agents 118 according to a color scheme that is in human-readable format. In some embodiments, one or more indicating units 120 may display one or more dosages 122 of one or more nutraceutical agents 118 and the formulation type of the one or more nutraceutical agents 118 according to a color scheme that is in human-readable format. In some embodiments, one or more indicating units 120 may display one or more dosages 122 of one or more nutraceutical agents 118, one or more routes of administration for the one or more nutraceutical agents 118, one or more times and/or periodicities for administration of the one or more nutraceutical agents 118, one or more formulation types for the one or more nutraceutical agents 118, whether to administer the one or more nutraceutical agents 118 with or without food, whether to administer the one or more nutraceutical agents 118 with or without other nutraceutical agents 118 and/or pharmaceutical agents, and substantially any combination thereof. Dosages 122 may be displayed according to numerous methods that are known and have been described (i.e., U.S. patent application Ser. No. 11/474,109, entitled CUSTOMIZED VISUAL MARKING FOR MEDICATION LABELING, filed 23 Jun. 2006, herein incorporated by reference to the extent such subject matter is not inconsistent herewith). In some embodiments, one or more indicating units 120 may indicate one or more dosages 122 in human-readable format and machine-readable format.

At operation 804, the indicating operation 240 may include indicating the one or more dosages of the one or more nutraceutical agents in machine-readable format. In some embodiments, one or more indicating units 120 can indicate the one or more dosages 122 of the one or more nutraceutical agents 118 in machine-readable format.

In some embodiments, one or more indicating units 120 may indicate one or more dosages 122 of one or more nutraceutical agents 118 in machine-readable format. Numerous methods may be used to indicate one or more dosages 122. Examples of such methods include, but are not limited to, radio frequency identification, bar coding, typographical methods, symbol based methods (i.e., use of symbols that represent dosages 122 and nutraceutical agents 118), optical methods (i.e., pulsed light), and the like.

In some embodiments, one or more indicating units 120 may indicate one or more dosages 122 of one or more nutraceutical agents 118 and the formulation type of the one or more nutraceutical agents 118 in machine-readable form. In some embodiments, one or more indicating units 120 may indicate one or more dosages 122 of one or more nutraceutical agents 118 in a pictographic form that is in machine-readable format. In some embodiments, one or more indicating units 120 may indicate one or more dosages 122 of one or more nutraceutical agents 118 and the formulation type of the one or more nutraceutical agents 118 in a pictographic form that is in machine-readable format. In some embodiments, one or more indicating units 120 may indicate one or more dosages 122 of one or more nutraceutical agents 118 according to a color scheme that is in machine-readable format. In some embodiments, one or more indicating units 120 may indicate one or more dosages 122 of one or more nutraceutical agents 118 and the formulation type of the one or more nutraceutical agents 118 according to a color scheme that is in machine-readable format. In some embodiments, one or more indicating units 120 may indicate one or more dosages 122 of one or more nutraceutical agents 118, one or more routes of administration for the one or more nutraceutical agents 118, one or more times and/or periodicities for administration of the one or more nutraceutical agents 118, one or more formulation types for the one or more nutraceutical agents 118, whether to administer the one or more nutraceutical agents 118 with or without food, whether to administer the one or more nutraceutical agents 118 with or without other nutraceutical agents 118 and/or pharmaceutical agents, and substantially any combination thereof. Numerous labeling methods are known and have been described that may be adapted into a machine-readable format (i.e., U.S. patent application Ser. No. 11/474,109, entitled CUSTOMIZED VISUAL MARKING FOR MEDICATION LABELING, filed 23 Jun. 2006, herein incorporated by reference to the extent such subject matter is not inconsistent herewith). In some embodiments, one or more indicating units 120 may indicate one or more dosages 122 in human-readable and in a machine-readable format.

At operation 806, the indicating operation 240 may include depositing the one or more dosages of the one or more nutraceutical agents on one or more labels. In some embodiments, one or more indicating units 120 can deposit the one or more dosages 122 of the one or more nutraceutical agents 118 on one or more labels.

In some embodiments, one or more indicating units 120 may print one or more labels that include one or more dosages 122 of one or more nutraceutical agents 118 and the formulation type of the one or more nutraceutical agents 118. In some embodiments, one or more indicating units 120 may print one or more labels that include one or more dosages 122 of one or more nutraceutical agents 118 in pictographic form. In some embodiments, one or more indicating units 120 may print one or more labels that include one or more dosages 122 of one or more nutraceutical agents 118 and the formulation type of the one or more nutraceutical agents 118 in pictographic form. In some embodiments, one or more indicating units 120 may print one or more labels that include one or more dosages 122 of one or more nutraceutical agents 118 according to a color scheme. In some embodiments, one or more indicating units 120 may print one or more labels that include one or more dosages 122 of one or more nutraceutical agents 118 and the formulation type of the one or more nutraceutical agents 118 according to a color scheme. In some embodiments, one or more indicating units 120 may indicate one or more dosages 122 of one or more nutraceutical agents 118, one or more routes of administration for the one or more nutraceutical agents 118, one or more times and/or periodicities for administration of the one or more nutraceutical agents 118, one or more formulation types for the one or more nutraceutical agents 118, whether to administer the one or more nutraceutical agents 118 with or without food, whether to administer the one or more nutraceutical agents 118 with or without other nutraceutical agents 118 and/or pharmaceutical agents, and substantially any combination thereof. Numerous labeling methods are known and have been described which may be adapted into machine-readable form (i.e., U.S. patent application Ser. No. 11/474,109, entitled CUSTOMIZED VISUAL MARKING FOR MEDICATION LABELING, filed 23 Jun. 2006, herein incorporated by reference to the extent such subject matter is not inconsistent herewith).

In some embodiments, one or more indicating units 120 may indicate one or more dosages 122 in human-readable and machine-readable form. Numerous types of depositing methods may be used by one or more indicating units 120. Examples of such methods include, but are not limited to, printing methods (i.e., stamping, ink-jet printing, laser printing, and the like). In some embodiments, ink containing magnetic particles may be used.

At operation 808, the indicating operation 240 may include dispensing the one or more nutraceutical agents. In some embodiments, one or more indicating units 120 can dispense the one or more nutraceutical agents 118.

One or more indicating units 120 may dispense one or more nutraceutical agents 118 in numerous dosage forms. In some embodiments, one or more indicating units 120 may dispense one or more nutraceutical agents 118 in powder form. In some embodiments, one or more indicating units 120 may dispense one or more nutraceutical agents 118 in liquid form. In some embodiments, one or more indicating units 120 may dispense one or more nutraceutical agents 118 in tablet form. In some embodiments, one or more indicating units 120 may dispense one or more nutraceutical agents 118 in capsule form.

At operation 810, the indicating operation 240 may include dispensing the one or more nutraceutical agents in unit dosage form. In some embodiments, one or more indicating units 120 can dispense the one or more nutraceutical agents 118 in unit dosage form.

In some embodiments, one or more indicating units 120 may dispense one or more nutraceutical agents 118 in a unit dosage form in which the entire dosage 122 is to be administered to an individual 108 as a single dosage 122. In some embodiments, one or more indicating units 120 may dispense one or more nutraceutical agents 118 in a unit dosage form that may be administered such that the individual 108 will maintain a level of the one or more nutraceuticals for a given time period. For example, in some embodiments, a unit dosage form may be an amount of one or more nutraceutical agents 118 that will allow the one or more nutraceutical agents 118 to be maintained within an individual 108 for four hours. Numerous criteria may be used to determine a unit dosage form. Examples of such criteria include, but are not limited to, physical characteristics of the individual 108, physiological characteristics of the individual 108, activity of the individual 108, and the like.

At operation 812, the indicating operation 240 may include dispensing two or more of the one or more nutraceutical agents in a single administration form. In some embodiments, one or more indicating units 120 can dispense two or more of the one or more nutraceutical agents 118 in a single administration form.

In some embodiments, one or more indicating units 120 may dispense two or more nutraceutical agents 118 in a single administration form to provide for administration of the two or more nutraceutical agents 118 to an individual 108. Such methods have been described (i.e., U.S. patent application Ser. No. 11/453,571, filed 14 Jun. 2006; U.S. patent application Ser. No. 11/478,341, filed 28 Jun. 2006; U.S. patent application Ser. No. 11/478,296, filed 28 Jun. 2006; and U.S.

patent application Ser. No. 11/486,998, filed 14 Jul. 2006, herein incorporated by reference to the extent such subject matter is not inconsistent herewith).

Figure 9:
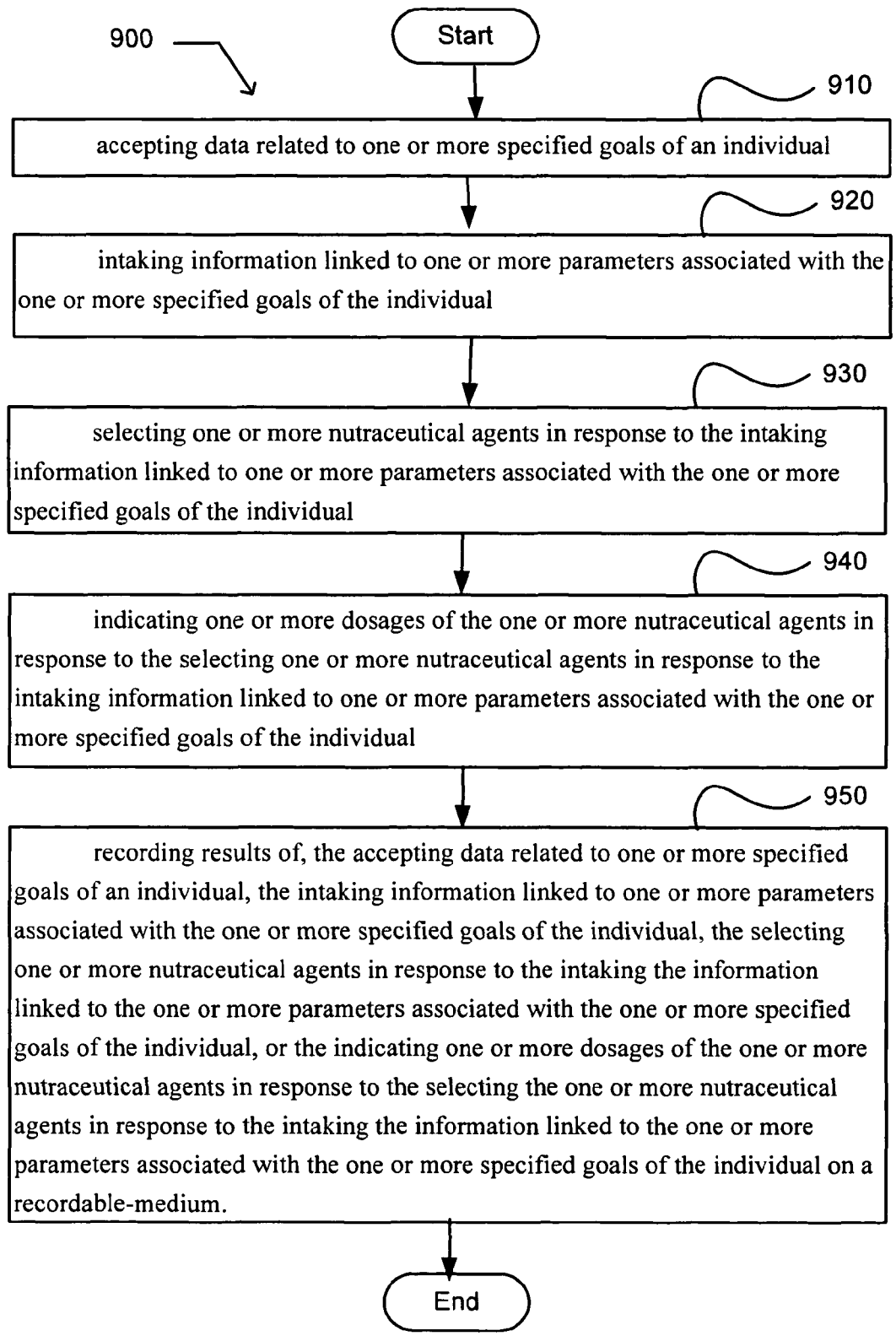
FIG. 9 illustrates an operational flow 900 representing example operations related to methods for nutraceutical agent selection and dosing.

FIG. 9 illustrates an operational flow 900 that includes an accepting operation 910, an intaking operation 920, a selecting operation 930, and an indicating operation 940 (which correspond to the accepting operation 210, the intaking operation 220, the selecting operation 230, and the indicating operation 240 illustrated in FIG. 2) with an additional recording operation 950. In FIG. 9, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 900 includes the operations 910, 920, 930, and 940 (which correspond to operations 210, 220, 230, and 240 as described with regard to FIG. 2) and an additional recording operation 950 involving recording results of, the accepting data related to one or more specified goals of an individual, the intaking information linked to one or more parameters associated with the one or more specified goals of the individual, the selecting one or more nutraceutical agents in response to the intaking the information linked to the one or more parameters associated with the one or more specified goals of the individual, or the indicating one or more dosages of the one or more nutraceutical agents in response to the selecting the one or more nutraceutical agents in response to the intaking the information linked to the one or more parameters associated with the one or more specified goals of the individual on a recordable-medium. In some embodiments, one or more recording units 124 may record results of, the accepting data 104 related to one or more specified goals 106 of an individual 108, the intaking information 112 linked to one or more parameters 114 associated with the one or more specified goals 106 of the individual 108, the selecting one or more nutraceutical agents 118 in response to the intaking information 112 linked to one or more parameters 114 associated with the one or more specified goals 106 of the individual 108, or the indicating one or more dosages 122 of the one or more nutraceutical agents 118 in response to the selecting one or more nutraceutical agents 118 in response to the intaking information 112 linked to one or more parameters 114 associated with the one or more specified goals 106 of the individual 108 on a recordable-medium 126.

Figure 10:
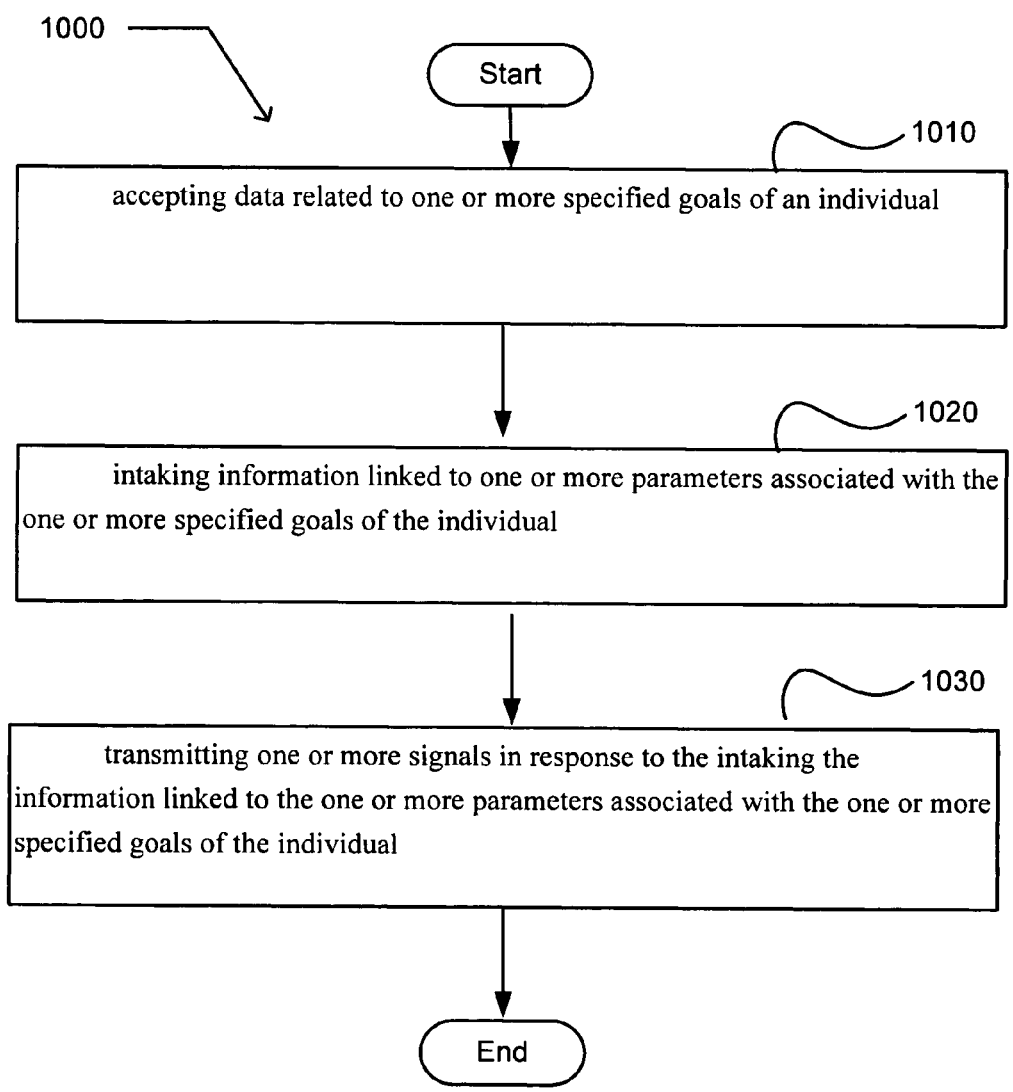
FIG. 10 illustrates an operational flow 1000 representing example operations related to methods for nutraceutical agent selection and dosing.

FIG. 10 illustrates an operational flow 1000 representing examples of operations that are related to the performance of a method for nutraceutical agent 118 and dosing. In FIG. 10 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 1000 includes an accepting operation 1010 involving accepting data related to one or more specified goals of an individual. In some embodiments, one or more accepting units 102 may accept data 104 related to one or more specified goals 106 of an individual 108.

In some embodiments, one or more accepting units 102 may accept data 104 related to one or more specified goals 106 of an individual 108. The one or more specified goals 106 may be virtually any goal to be achieved, or attempted by, an individual 108 that may be affected by administration of one or more nutraceutical agents 118 to the individual 108. In some embodiments, administration of one or more nutraceutical agents 118 to an individual 108 may assist the individual 108 to achieve one or more specified goals 106. In some embodiments, administration of one or more nutraceutical agents 118 to an individual 108 may stimulate the individual 108 to achieve one or more specified goals 106. In some embodiments, administration of one or more nutraceutical agents 118 to an individual 108 may reduce an inhibition coupled to the individual 108 to promote achieving one or more specified goals 106 by the individual 108. Numerous examples of specified goals 106 of an individual 108 exist. In some embodiments, specified goals 106 of an individual 108 may be related to attentiveness, alertness, test performance, relaxation, pain, fever, attractiveness, anxiety, fall, injury, accident, bite, bleeding, inflammation, infection, drowsiness, insomnia, discomfort, stress, grooming, appearance, capability, performance, improvement, enhancement, curtailment, wellbeing, vitality, vigor, disability, phobia, malady, psychosis, environmental extremes, environmental exposure, dysfunction, disease symptom, chronic condition, mental acuity, emotional behavior, physical prowess, addiction, obsession, therapy, remedy, behavior, nutrition, diet, exercise, immunization, prevention, diagnosis, subscription, regimen, social performance, social interaction, endurance, sexual attribute, sexual performance, age-related attribute, age-related condition, prophylaxis, treatment, and substantially any combination thereof. In some embodiments, data 104 may include identification of one or more of the specified goals 106 of an individual 108. In some embodiments, data 104 may include characteristics of an individual 108. Examples of such data 104 may include, but are not limited to, physical characteristics, metabolic characteristics, financial characteristics, and the like. In some embodiments, data 104 may include, an individual's 108 height, weight, gender, kidney function, liver function, level of physical fitness, age, allergic response, metabolic level (i.e., resting metabolic rate and/or activity-related metabolic rate), disease state, body fat percentage, body mass index, personal health habits (i.e., smoking, alcohol consumption, diet, illegal drug use, and the like), family health history, insurance coverage, food supplement usage, nutraceutical agent 118 usage, non-prescription drug use, prescription drug use, pregnancy status, and the like. In some embodiments, the one or more characteristics may be specifically associated with an individual 108. As such, in some embodiments, the one or more characteristics may be unique to the individual 108 as opposed to being common to a group. For example, in some embodiments, an individual 108 may be a member of a group of persons who are diabetic while exhibiting one or more characteristics, such as metabolic characteristics, that are unique to the individual 108. Accordingly, in some embodiments, data 104 may be input that provides for selection of nutraceutical agents 118 in accordance with one or more characteristics and specified goals 106 of an individual 108.

After a start operation, the operational flow 1000 includes an intaking operation 1020 involving intaking information linked to one or more parameters associated with the one or more specified goals of the individual. In some embodiments, one or more intaking units 110 may intake information 112 linked to one or more parameters 114 associated with the one or more specified goals 106 of the individual 108.

In some embodiments, one or more intaking units 110 may intake information 112 linked to one or more parameters 114 associated with the one or more specified goals 106 of the individual 108. Numerous parameters 114 may be associated with one or more specified goals 106 of an individual 108. Examples of such parameters 114 include, but are not limited to, blood sugar levels, blood insulin levels, blood iron levels, hormone levels (amine-derived hormones: such as catecholamines (adrenaline, dopamine, noradrenaline); tryptophan derivatives (melatonin, serotonin); tyrosine derivatives (thyroxine and triiodothyronine); peptide hormones such as anti-mullerian hormone, adiponectin, adrenocorticotropic hormone, angiotensinogen and angiotensin, antidiuretic hormone, atrial-natriuretic peptide, calcitonin, cholecystokinin, corticotropin-releasing hormone, erythropoietin, follicle-stimulating hormone, gastrin, ghrelin, glucagons, gonadotropin-releasing hormone, growth hormone-releasing hormone, human chorionic gonadotropin, growth hormone, inhibin, insulin, insulin-like growth factor, luteinizing hormone, melanocyte stimulating hormone, neuropeptide Y, oxytocin, parathyroid hormone, prolactin, relaxin, secretin, somatostatin, thrombopoietin, thyroid-stimulating hormone, thyrotropin-releasing hormone; steroid hormones: Glucocorticoids (cortisol); Mineralocorticoids (aldosterone); sex steroids: androgens (testosterone, dehydroepiandrosterone, dehydroepiandrosterone sulfate, androstenedione, dihydrotestosterone); estrogens (estradiol); progestagens (progesterone and progestins); sterol hormones: vitamin D derivatives (calcitriol); lipid hormones (prostaglandins, leukotrienes, prostacyclin, and thromboxane)), nutraceutical agent 118 levels, pharmaceutical agent levels, cytokine levels, and the like (i.e., Fitzgerald et al., The Cytokine Facts Book, Academic Press, San Francisco, Second Edition, (2001)). Methods to gain information 112 with regard to components of biological systems are known (i.e., Clinical Laboratory Medicine, Lippincott Williams and Wilkins, Philadelphia, Second Edition, 2002). In some embodiments, one or more intaking units 110 may include instrumentation that provides for analysis of a sample obtained from an individual 108. For example, in some embodiments, an intaking unit 110 may be configured to intake a blood sample obtained from an individual 108 and analyze the blood sample to determine one or more parameters 114 associated with one or more specified goals 106 of an individual 108 (i.e., determine the level of free testosterone or the level of melatonin in a blood sample obtained from an individual 108). Numerous analytical technologies are known and may be included within one or more intaking units 110. Examples of such technologies include, but are not limited to, gas chromatography, mass spectrometry, atomic absorption, immunoassay based methods, microfluidic based methods, spectrophotometry (i.e., infrared, ultraviolet, fluorescence, and the like), surface plasmon resonance, fluorescence resonance energy transfer, and the like. In some embodiments, one or more intaking units 110 may intake information 112 linked to one or more parameters 114 associated with the one or more specified goals 106 of an individual 108 from a source that is independent of the one or more intaking units 110. In some embodiments, one or more intaking units 110 may intake information 112 linked to one or more parameters 114 associated with the one or more specified goals 106 of an individual 108 from a source that is coupled to the one or more intaking units 110.

After a start operation, the operational flow 1000 includes a transmitting operation 1030 involving transmitting one or more signals in response to the intaking the information linked to the one or more parameters associated with the one or more specified goals of the individual. In some embodiments, one or more transmitting units 128 may transmit one or more signals 130 in response to the intaking information 112 linked to one or more parameters 114 associated with the one or more specified goals 106 of the individual 108.

In some embodiments, one or more transmitting units 128 transmit one or more levels of one or more metabolic indicators linked to the individual 108. In some embodiments, one or more transmitting units 128 transmit one or more levels of one or more metabolic activities linked to the individual 108. In some embodiments, one or more transmitting units 128 transmit one or more levels of one or more nutraceutical agents 118 linked to the individual 108. In some embodiments, one or more transmitting units 128 transmit one or more levels of one or more pharmaceutical agents linked to the individual 108. In some embodiments, one or more transmitting units 128 transmit one or more parameters 114 associated with the one or more specified goals 106 of the individual 108. In some embodiments, one or more transmitting units 128 transmit one or more instructions to select one or more nutraceutical agents 118 in response to the intaking information 112 linked to one or more parameters 114 associated with the one or more specified goals 106 of the individual 108. In some embodiments, one or more transmitting units 128 transmit one or more signals 130 to select one or more nutraceutical agents 118 to increase one or more levels of one or more components associated with the one or more specified goals 106 of the individual 108. In some embodiments, one or more transmitting units 128 transmit one or more signals 130 to select one or more nutraceutical agents 118 to decrease one or more levels of one or more components associated with the one or more specified goals 106 of the individual 108. In some embodiments, one or more transmitting units 128 transmit one or more signals 130 to select one or more nutraceutical agents 118 that stimulate one or more metabolic pathways linked to the individual 108. In some embodiments, one or more transmitting units 128 transmit one or more signals 130 to select one or more nutraceutical agents 118 that inhibit one or more metabolic pathways linked to the individual 108. In some embodiments, one or more transmitting units 128 transmit one or more signals 130 to select at least one vitamin, mineral, enzyme, amino acid, homeopathic supplement, toxin, homeopathic substance, traditional remedy, herbal supplement, glandular supplement, or substantially any combination thereof.

In some embodiments, one or more transmitting units 128 may transmit one or more signals 130 that include data 104 related to one or more specified goals 106 of an individual 108. One or more transmitting units 128 may transmit one or more signals 130 through use of numerous technologies. Examples of such technologies include, but are not limited to, wireless transmission, telephone, internet transmission, digital transmission, analog transmission, optical transmission, and the like.

Figure 11:
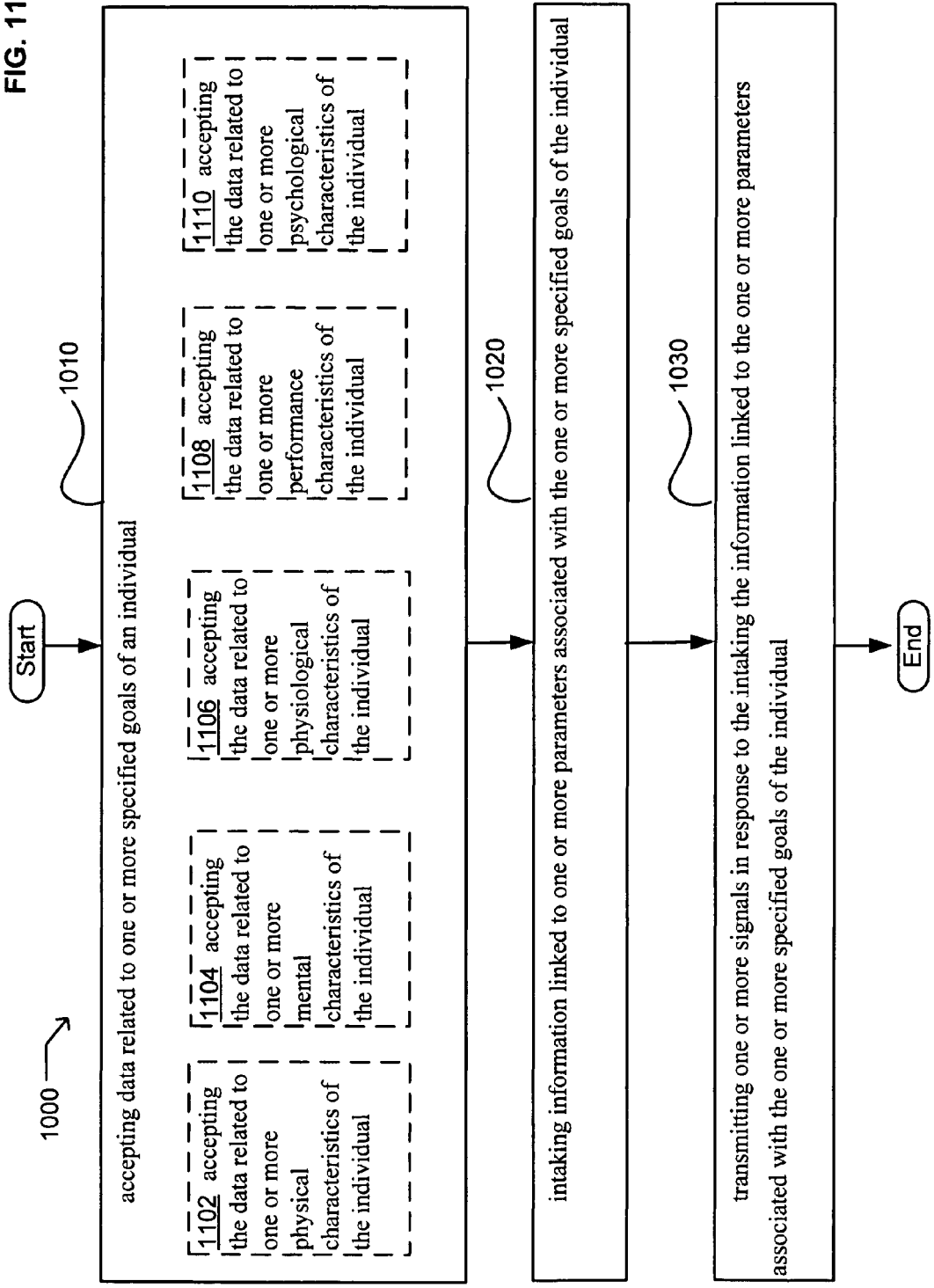
FIG. 11 illustrates alternative embodiments of the example operation flow of FIG. 10.

FIG. 11 illustrates alternative embodiments of the example operational flow 1000 of FIG. 10. FIG. 11 illustrates example embodiments where the accepting operation 1010 may include at least one additional operation. Additional operations may include an operation 1102, an operation 1104, an operation 1106, an operation 1108, and/or an operation 1110.

At operation 1102, the accepting operation 1010 may include accepting the data related to one or more physical characteristics of the individual. In some embodiments, one or more accepting units 102 accept data 104 related to one or more physical characteristics of the individual 108.

One or more accepting units 102 may accept data 104 related to numerous physical characteristics of an individual 108. Examples of such physical characteristics include, but are not limited to, height, weight, gender, kidney function, liver function, level of physical fitness, age, allergic response, metabolic level (i.e., resting metabolic rate and/or activity-related metabolic rate), disease state, body fat percentage, body mass index, personal health habits (i.e., smoking, alcohol consumption, diet, illegal drug use, and the like), family health history, food supplement usage, nutraceutical agent 118 usage, non-prescription drug use, prescription drug use, pregnancy status, and the like. In some embodiments, such data 104 may be used to identify one or more nutraceutical agents 118 that are compatible with an individual 108. For example, if an individual 108 is taking a selective serotonin reuptake inhibitor (SSRI), one or more nutraceutical agents 118 should not be selected that would interfere with the serotonin reuptake inhibitor.

At operation 1104, the accepting operation 1010 may include accepting the data related to one or more mental characteristics of the individual. In some embodiments, one or more accepting units 102 accept data 104 related to one or more mental characteristics of the individual 108.

One or more accepting units 102 may accept data 104 related to numerous mental characteristics of an individual 108. Examples of such mental characteristics include, but are not limited to, daily time periods when the mental processes of an individual 108 are most acute or least acute (i.e., morning, afternoon, evening, night), an individual's 108 sleep schedule, an individual's 108 daily schedule of activities (i.e., meetings, presentations, travel, athletic activity), and the like.

At operation 1106, the accepting operation 1010 may include accepting the data related to one or more physiological characteristics of the individual. In some embodiments, one or more accepting units 102 accept data 104 related to one or more physiological characteristics of the individual 108.

One or more accepting units 102 may accept data 104 related to numerous physiological characteristics of an individual 108. Examples of such physiological characteristics include, but are not limited to, the ability of an individual 108 to metabolize one or more nutraceutical agents 118, the ability of an individual 108 to metabolize one or more pharmaceutical agents, the response of an individual 108 to one or more pharmaceutical agents, the response of an individual 108 to one or more nutraceutical agents 118, the concentration or level of one or more metabolites in one or more samples obtained from an individual 108, the concentration or level of one or more components of a sample obtained from an individual 108 that include, but are not limited to, concentrations or levels of: vitamins, minerals, metals, proteins, one or more hormones, hemoglobin, one or more neurotransmitters, metabolites, proteolytic products, antibodies, white blood cells, red blood cells, enzyme activities, lipids, lipoproteins, carbohydrates, phosphates, tumor markers, bacteria, fungi, viruses, parasites, and the like.

At operation 1108, the accepting operation 1010 may include accepting the data related to one or more performance characteristics of the individual. In some embodiments, one or more accepting units 102 accept data 104 related to one or more performance characteristics of the individual 108.

One or more accepting units 102 may accept data 104 related to numerous performance characteristics of an individual 108. Generally, performance characteristics relate to physical or mental activities in which an individual 108 engages. Examples of such performance characteristics include, but are not limited to, athletic ability, mental ability, sexual ability, ability to interact socially, and the like. For example, in some embodiments, data 104 related to giving a presentation may be accepted.

At operation 1110, the accepting operation 1010 may include accepting the data related to one or more psychological characteristics of the individual. In some embodiments, one or more accepting units 102 accept data 104 related to one or more psychological characteristics of the individual 108.

One or more accepting units 102 may accept data 104 related to numerous psychological characteristics of an individual 108. Examples of such psychological characteristics include, but are not limited to, the presence or absence of a psychological malady. Examples of psychological maladies include, but are not limited to, antisocial personal disorder, anxiety disorder, avoidant personality disorder, bipolar disorder, conduct disorder, depression, depressive disorder, drug addiction, insomnia, primary sleep disorders, schizophrenia, seasonal affective disorder, sexual disorder, sexual dysfunctions, social anxiety disorder, specific phobia, and the like.

Figure 12:
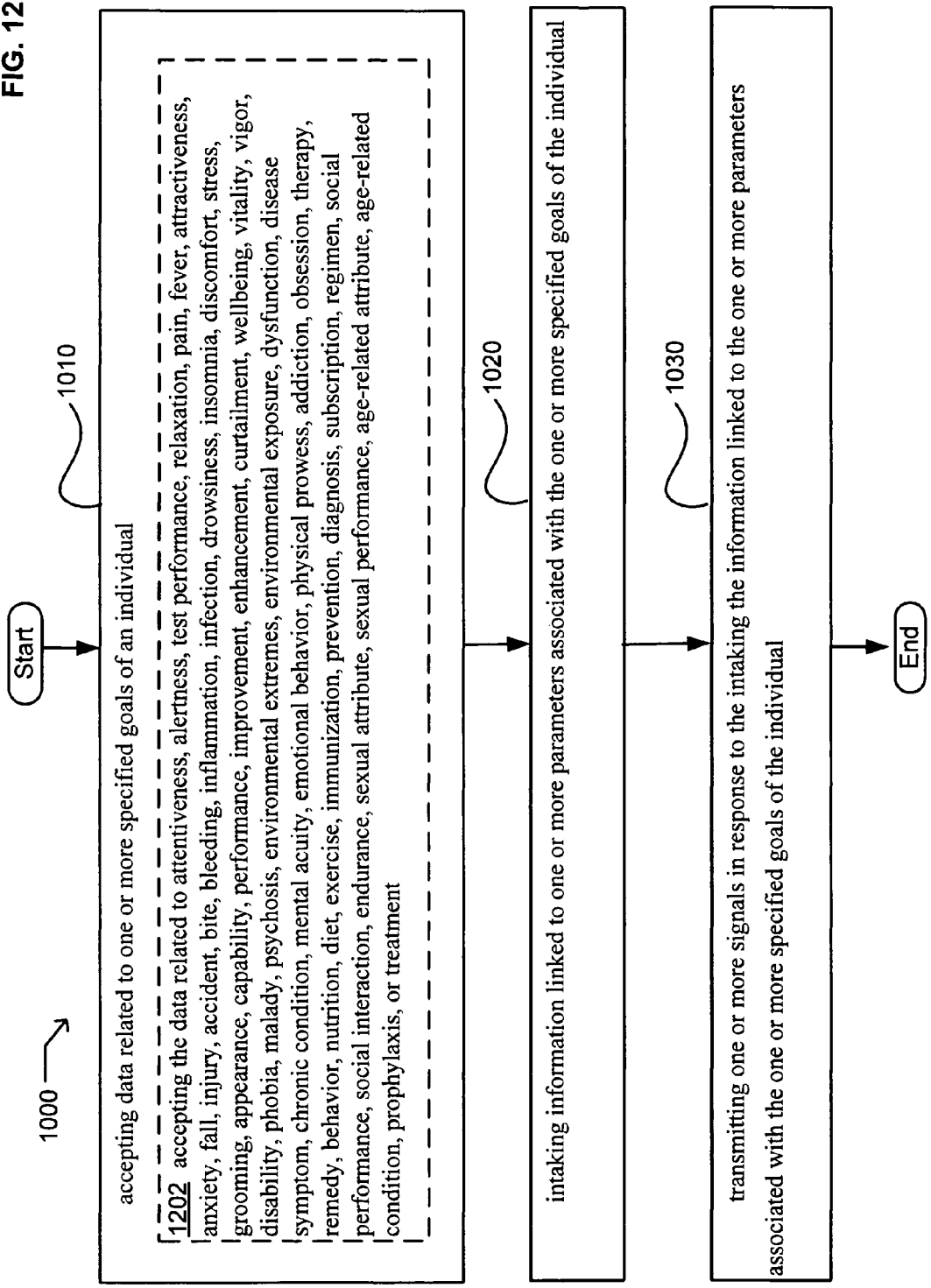
FIG. 12 illustrates alternative embodiments of the example operation flow of FIG. 10.

FIG. 12 illustrates alternative embodiments of the example operational flow 1000 of FIG. 10. FIG. 12 illustrates example embodiments where the accepting operation 1010 may include at least one additional operation 1202.

At operation 1202, the accepting operation 1010 may include accepting the data related to attentiveness, alertness, test performance, relaxation, pain, fever, attractiveness, anxiety, fall, injury, accident, bite, bleeding, inflammation, infection, drowsiness, insomnia, discomfort, stress, grooming, appearance, capability, performance, improvement, enhancement, curtailment, wellbeing, vitality, vigor, disability, phobia, malady, psychosis, environmental extremes, environmental exposure, dysfunction, disease symptom, chronic condition, mental acuity, emotional behavior, physical prowess, addiction, obsession, therapy, remedy, behavior, nutrition, diet, exercise, immunization, prevention, diagnosis, subscription, regimen, social performance, social interaction, endurance, sexual attribute, sexual performance, age-related attribute, age-related condition, prophylaxis, or treatment. In some embodiments, one or more accepting units 102 accept data 104 related to attentiveness, alertness, test performance, relaxation, pain, fever, attractiveness, anxiety, fall, injury, accident, bite, bleeding, inflammation, infection, drowsiness, insomnia, discomfort, stress, grooming, appearance, capability, performance, improvement, enhancement, curtailment, wellbeing, vitality, vigor, disability, phobia, malady, psychosis, environmental extremes, environmental exposure, dysfunction, disease symptom, chronic condition, mental acuity, emotional behavior, physical prowess, addiction, obsession, therapy, remedy, behavior, nutrition, diet, exercise, immunization, prevention, diagnosis, subscription, regimen, social performance, social interaction, endurance, sexual attribute, sexual performance, age-related attribute, age-related condition, prophylaxis, or treatment.

Figure 13:
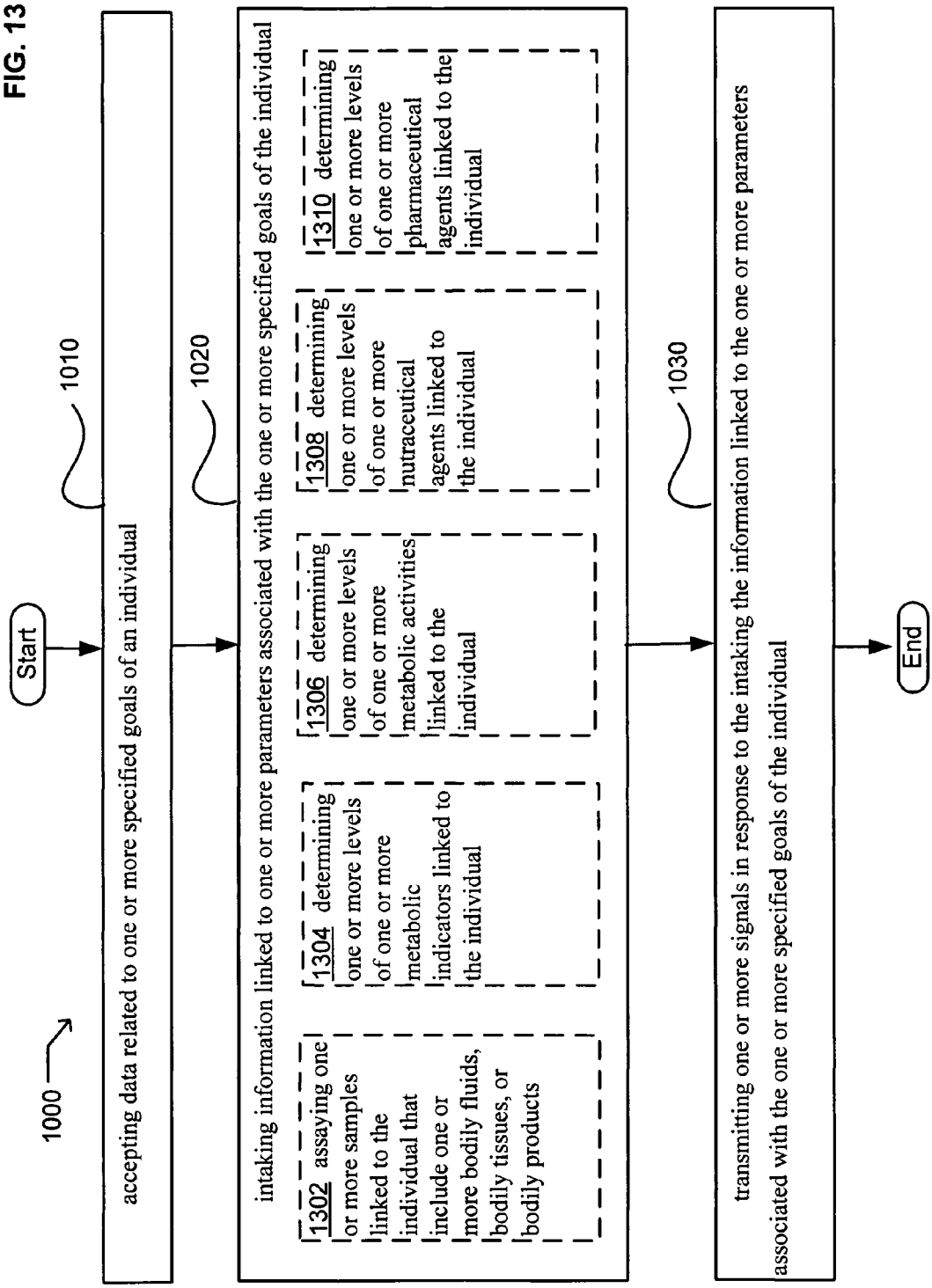
FIG. 13 illustrates alternative embodiments of the example operation flow of FIG. 10.

FIG. 13 illustrates alternative embodiments of the example operational flow 1000 of FIG. 10. FIG. 13 illustrates example embodiments where the intaking operation 1020 may include at least one additional operation. Additional operations may include an operation 1302, an operation 1304, an operation 1306, an operation 1308, and/or an operation 1310.

At operation 1302, the intaking operation 1020 may include assaying one or more samples linked to the individual that include one or more bodily fluids, bodily tissues, or bodily products. In some embodiments, one or more intaking units 110 can assay one or more samples linked to the individual 108 that include one or more bodily fluids, bodily tissues, or bodily products. Examples of such samples include, but are not limited to, blood, urine, saliva, synovial fluid, pleural fluid, peritoneal fluid, tears, mucus, ejaculate, skin, muscle, bone, hair, teeth, nails, urine, breath, fecal material, genital products, and the like.

At operation 1304, the intaking operation 1020 may include determining one or more levels of one or more metabolic indicators linked to the individual. In some embodiments, one or more intaking units 110 determine one or more levels of one or more metabolic indicators linked to the individual 108.

For example, vitamin $B_{12}$ and folate are two vitamins that have interdependent roles in nucleic acid synthesis. Deficiencies of either vitamin can cause megaloblastic anemia. Accordingly, in some embodiments, the levels of homocysteine and methylmalonic acid may be determined and used as metabolic indicators to indicate levels of vitamin $B_{12}$ and folate within an individual 108. In some embodiments, vitamin A deficiency may be assessed by determining albumin levels which are an indirect measure of vitamin A levels. In some embodiments, magnesium levels may be assessed directly. In some embodiments, magnesium levels may be assessed indirectly through analysis of insulin because magnesium deficiency results in impaired insulin secretion. Accordingly, in some embodiments, magnesium replacement may be used to restore insulin secretion. In some embodiments, fluorescent indicators may be used to determine chloride, zinc, and calcium levels as well as pH. Accordingly, numerous metabolic indicators that are linked to an individual 108 may be determined through use of known methods.

At operation 1306, the intaking operation 1020 may include determining one or more levels of one or more metabolic activities linked to the individual. In some embodiments, one or more intaking units 110 determine one or more levels of one or more metabolic activities linked to the individual 108.

In some embodiments, one or more intaking units 110 can be used to determine one or more enzyme activities of an individual 108. For example, when digested properly, protein supplies acidity to the blood. If an individual 108 is not able to adequately digest protein, the individual's 108 blood acquires excess alkaline reserves which must be continuously dumped via the kidneys into the urine. Accordingly, in some embodiments, blood alkalinity may be tested to assist in determining if an individual 108 is deficient in protease activity. In instances of protease deficiency, an individual 108 may wish to ingest a protease supplement to assist with digestion of protein. In some embodiments, enzyme activity may be determined directly. For example, protease activity can be measured directly through use of peptide substrates having an amino acid sequence that is recognized by a protease to be assayed. Such peptide substrates may be readily prepared or be obtained from commercial sources (i.e., Biotium, Inc., Hayward, Calif.; Biomol International Inc., Plymouth Meeting, Pa.; JPT Peptide Technologies, Inc., Springfield, Va.). In some embodiments, vitamin K deficiency exhibited by an individual 108 may be determined through measurement of Protein Induced by Vitamin K Absence (PIVKA-II) using several known methods (Widdershoven J., Clin. Chem., 33(11):2074-2078 (1987)). Examples of such methods include, but are not limited to, electrophoresis-immunofixation and enzyme immunoassay. Numerous metabolic activities of an individual 108 may be determined through use of methods that are known and that have been described (i.e., Clinical Laboratory Medicine, Lippincott Williams and Wilkins, Philadelphia, Second Edition, 2002).

At operation 1308, the intaking operation 1020 may include determining one or more levels of one or more nutraceutical agents linked to the individual. In some embodiments, one or more intaking units 110 determine one or more levels of one or more nutraceutical agents 118 linked to the individual 108.

Numerous methods may be used to determine one or more nutraceutical agents 118 that are linked to an individual 108. Examples of such methods include, but are not limited to, chromatographic assay, mass spectrometry, spectrophotometry, immunological assay, and the like. These methods may be performed on numerous types of samples obtained from an individual 108 that are exemplified by bodily fluids, bodily tissues, bodily products and the like.

At operation 1310, the intaking operation 1020 may include determining one or more levels of one or more pharmaceutical agents linked to the individual. In some embodiments, one or more intaking units 110 determine one or more levels of one or more pharmaceutical agents linked to the individual 108.

Numerous methods may be used to determine one or more pharmaceutical agents that are linked to an individual 108. Examples of such methods include, but are not limited to, chromatographic assay, mass spectrometry, spectrophotometry, immunological assay, and the like. These methods may be performed on numerous types of samples obtained from an individual 108 that are exemplified by bodily fluids, bodily tissues, bodily products and the like.

Figure 14:
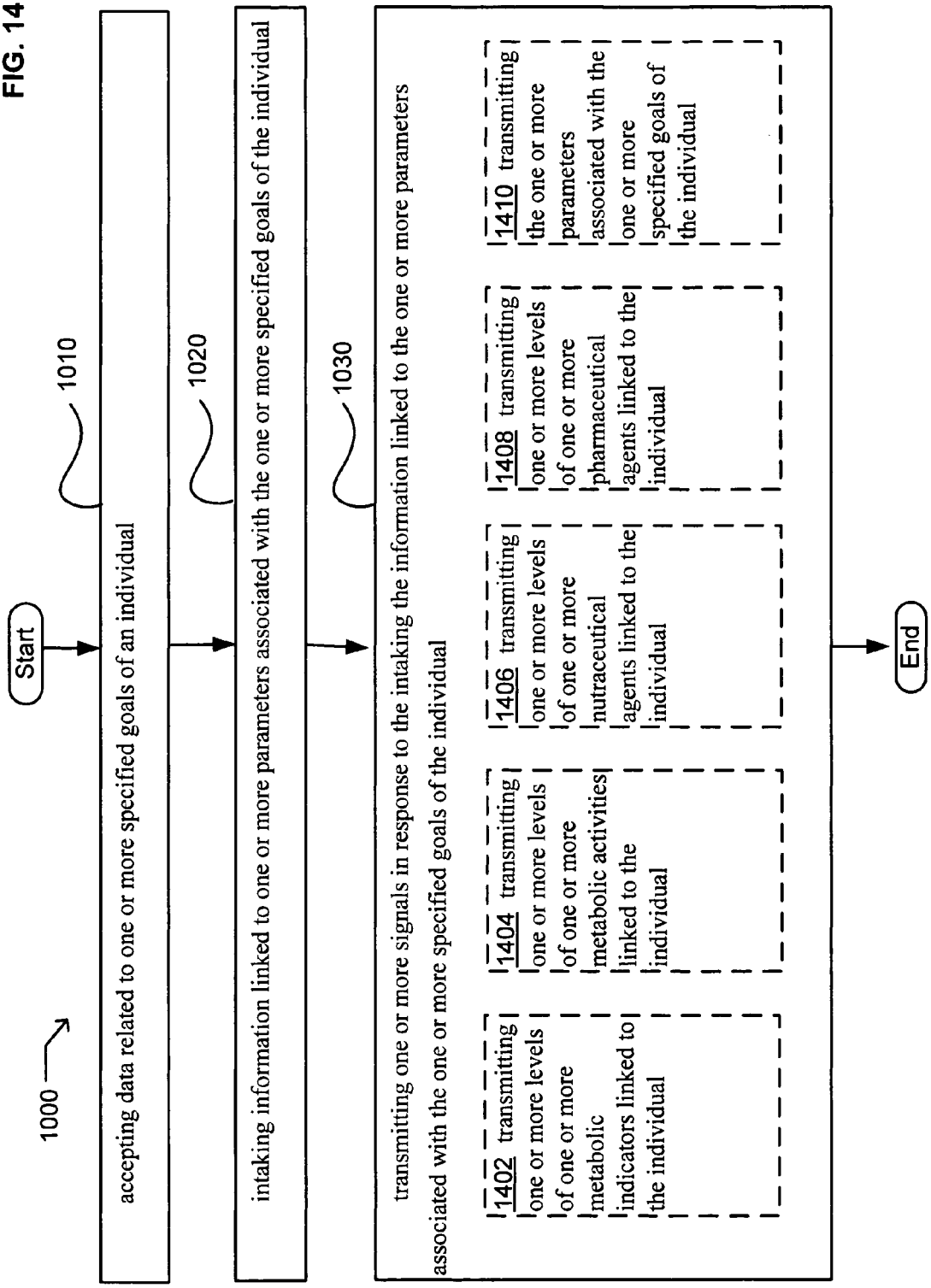
FIG. 14 illustrates alternative embodiments of the example operation flow of FIG. 10.

FIG. 14 illustrates alternative embodiments of the example operational flow 1000 of FIG. 10. FIG. 14 illustrates example embodiments where the transmitting operation 1030 may include at least one additional operation. Additional operations may include an operation 1402, an operation 1404, an operation 1406, an operation 1408, and/or an operation 1410.

At operation 1402, the transmitting operation 1030 may include transmitting one or more levels of one or more metabolic indicators linked to the individual. In some embodiments, one or more transmitting units 128 transmit one or more levels of one or more metabolic indicators linked to the individual 108.

In some embodiments, one or more transmitting units 128 may transmit one or more signals 130 indicating the levels of homocysteine and methylmalonic acid to indicate levels of vitamin $B_{12}$ and folate within an individual 108. In some embodiments, one or more transmitting units 128 may transmit one or more signals 130 indicating the level of albumin as an indirect measure of vitamin A levels. In some embodiments, one or more transmitting units 128 may transmit one or more signals 130 indicating the level of a metabolic indicator directly. For example, in some embodiments, one or more transmitting units 128 may transmit one or more signals 130 indicating vitamin A concentration, pH, magnesium concentration, calcium concentration, and the like. One or more transmitting units 128 may transmit one or more signals 130 indicating the level of numerous metabolic indicators.

At operation 1404, the transmitting operation 1030 may include transmitting one or more levels of one or more metabolic activities linked to the individual. In some embodiments, one or more transmitting units 128 transmit one or more levels of one or more metabolic activities linked to the individual 108.

In some embodiments, one or more transmitting units 128 can be used to transmit one or more signals 130 indicating the level of one or more enzyme activities of an individual 108. For example, in some embodiments, one or more transmitting units 128 can transmit one or more signals 130 indicating the level of a protease activity of an individual 108. In some embodiments, one or more transmitting units 128 can transmit one or more signals 130 indicating the level of Protein Induced by Vitamin K Absence (PIVKA-II) to indicate vitamin K deficiency or adequacy of an individual 108. One or more transmitting units 128 may transmit one or more signals 130 indicating the level of numerous metabolic activities linked to an individual 108.

At operation 1406, the transmitting operation 1030 may include transmitting one or more levels of one or more nutraceutical agents linked to the individual. In some embodiments, one or more transmitting units 128 transmit one or more levels of one or more nutraceutical agents 118 linked to the individual 108.

In some embodiments, one or more transmitting units 128 can transmit one or more signals 130 indicating one or more levels of one or more nutraceutical agents 118 that were determined at one or more times. For example, in some embodiments, one or more signals 130 indicating the level of a nutraceutical agent 118 at the time when administered to an individual 108, at time two hours post-administration, at time four hours post-administration, and at time six hours post-administration may be transmitted. Accordingly, in some embodiments, the rate at which one or more nutraceutical agents 118 are metabolized by an individual 108 may be determined. In some embodiments, the rate at which a level of nutraceutical is reached within an individual 108 may be determined. One or more signals 130 indicating numerous times and concentrations of nutraceutical agents 118 may be transmitted.

At operation 1408, the transmitting operation 1030 may include transmitting one or more levels of one or more pharmaceutical agents linked to the individual. In some embodiments, one or more transmitting units 128 transmit one or more levels of one or more pharmaceutical agents linked to the individual 108.

In some embodiments, one or more transmitting units 128 can transmit one or more signals 130 indicating one or more levels of one or more pharmaceutical agents that were determined at one or more times. For example, in some embodiments, one or more signals 130 indicating the level of a pharmaceutical agent at the time when administered to an individual 108, at time two hours post-administration, at time four hours post-administration, and at time six hours post-administration may be transmitted. Accordingly, in some embodiments, the rate at which one or more pharmaceutical agents are metabolized by an individual 108 may be determined. In some embodiments, the rate at which a level of a pharmaceutical agent is reached within an individual 108 may be determined. One or more signals 130 indicating numerous times and concentrations of pharmaceutical agents may be transmitted.

At operation 1410, the transmitting operation 1030 may include transmitting the one or more parameters associated with the one or more specified goals of the individual. In some embodiments, one or more transmitting units 128 transmit one or more parameters 114 associated with the one or more specified goals 106 of the individual 108.

One or more transmitting units 128 can transmit one or more signals 130 indicating numerous parameters 114 that are associated with one or more specified goals 106 of an individual 108. Examples of such parameters 114 include, but are not limited to, blood sugar levels, blood insulin levels, blood iron levels, hormone levels, nutraceutical agent 118 levels, pharmaceutical agent levels, cytokine levels, and the like (i.e., Fitzgerald et al., The Cytokine Facts Book, Academic Press, San Francisco, Second Edition, (2001)).

Figure 15:
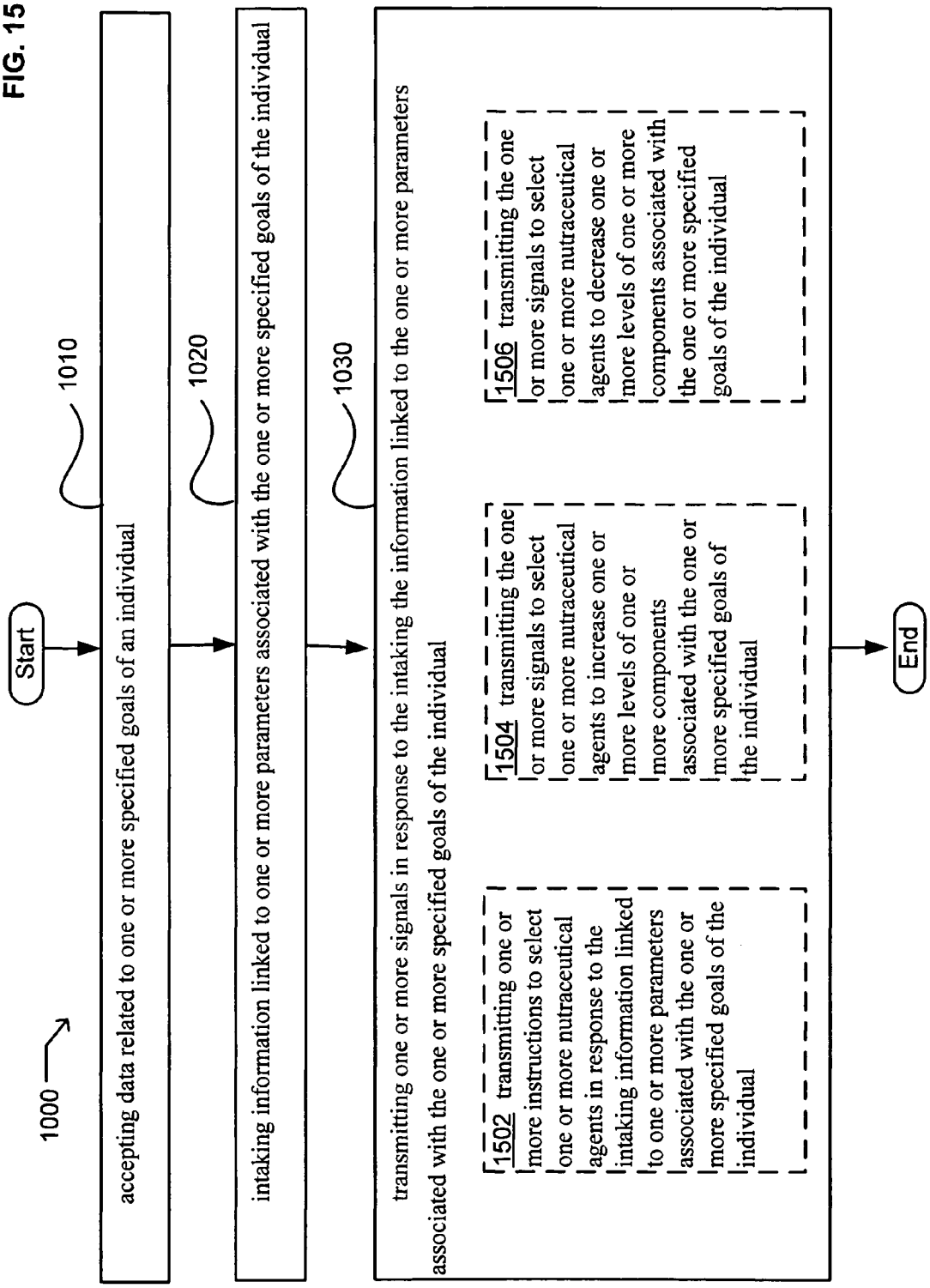
FIG. 15 illustrates alternative embodiments of the example operation flow of FIG. 10.

FIG. 15 illustrates alternative embodiments of the example operational flow 1000 of FIG. 10. FIG. 15 illustrates example embodiments where the transmitting operation 1030 may include at least one additional operation. Additional operations may include an operation 1502, an operation 1504, and/or an operation 1506.

At operation 1502, the transmitting operation 1030 may include transmitting one or more instructions to select one or more nutraceutical agents in response to the intaking information linked to one or more parameters associated with the one or more specified goals of the individual. In some embodiments, one or more transmitting units 128 transmit one or more instructions to select one or more nutraceutical agents 118 in response to the intaking information 112 linked to one or more parameters 114 associated with the one or more specified goals 106 of the individual 108.

In some embodiments, one or more transmitting units 128 transmit one or more signals 130 that include one or more instructions to select one or more nutraceutical agents 118 in response to accepting data 104 related to one or more specified goals 106 of an individual 108. One or more transmitting units 128 can transmit one or more signals 130 that include one or more instructions to select one or more nutraceutical agents 118 based on numerous parameters 114. Examples of such parameters 114 include, but are not limited to, blood sugar levels, blood insulin levels, blood iron levels, hormone levels, nutraceutical agent 118 levels, pharmaceutical agent levels, cytokine levels, and the like.

At operation 1504, the transmitting operation 1030 may include transmitting the one or more signals to select one or more nutraceutical agents to increase one or more levels of one or more components associated with the one or more specified goals of the individual. In some embodiments, one or more transmitting units 128 transmit one or more signals 130 to select one or more nutraceutical agents 118 to increase one or more levels of one or more components associated with the one or more specified goals 106 of the individual 108.

In some embodiments, one or more transmitting units 128 transmit one or more signals 130 to select one or more nutraceutical agents 118 that may directly complement one or more levels of one or more components associated with one or more specified goals 106 of the individual 108. For example, in some embodiments, one or more transmitting units 128 transmit one or more signals 130 to select calcium in various forms (i.e., calcium citrate, calcium aspartate, calcium carbonate) to avoid or reduce the effects of osteoporosis. In another embodiment, one or more transmitting units 128 transmit one or more signals 130 to select chromium to lower blood sugar, increase insulin sensitivity, reduce body fat, control hunger, suppress appetite, increase lean body/muscle mass, or substantially any combination thereof. In some embodiments, one or more transmitting units 128 transmit one or more signals 130 to select one or more nutraceutical agents 118 to indirectly supplement a component associated with one or more specified goals 106 of an individual 108. For example, one or more transmitting units 128 may transmit one or more signals 130 to select 5-hydroxy-tryptophan for administration to an individual 108 if the individual 108 suffers from depression and is found to exhibit low levels of serotonin. Numerous signals 130 may be transmitted to select one or more nutraceutical agents 118 to increase one or more levels of one or more components associated with one or more specified goals 106 of an individual 108.

At operation 1506, the transmitting operation 1030 may include transmitting the one or more signals to select one or more nutraceutical agents to decrease one or more levels of one or more components associated with the one or more specified goals of the individual. In some embodiments, one or more transmitting units 128 transmit one or more signals 130 to select one or more nutraceutical agents 118 to decrease one or more levels of one or more components associated with the one or more specified goals 106 of the individual 108.

Low density lipoproteins are examples of components that are linked to vascular disease. Accordingly, in some embodiments, one or more transmitting units 128 may transmit one or more signals 130 to select one or more nutraceutical agents 118 that will act to lower the low density lipoprotein concentration of an individual 108. Examples of such nutraceutical agents 118 include, but are not limited to, plant stanols, dietary fiber, stanol esters, isoflavones, diallyl sulfides, niacin, soy protein, and substantially any combination thereof. Glucose is an example of a component that is linked to hyperglycemia. Accordingly, in some embodiments, one or more transmitting units 128 may transmit one or more signals 130 to select buckwheat to lower blood glucose levels of an individual 108. Free radical oxygen species that include singlet oxygen, hydroxyl radicals, peroxides, and superoxide radicals are components that act to damage lipids and other cellular structures. Accordingly, in some embodiments, one or more transmitting units 128 may transmit one or more signals 130 to select one or more nutraceutical agents 118 to reduce levels of free radicals within an individual 108. Examples of such nutraceutical agents 118 include, but are not limited to, terpenes, carotenoids, limonoids, phenols, flavonoids, isoprenoids, and the like. One or more transmitting units 128 can transmit one or more signals 130 to select numerous types of nutraceutical agents 118 to decrease one or more levels of one or more components associated with the one or more specified goals 106 of the individual 108.

Figure 16:
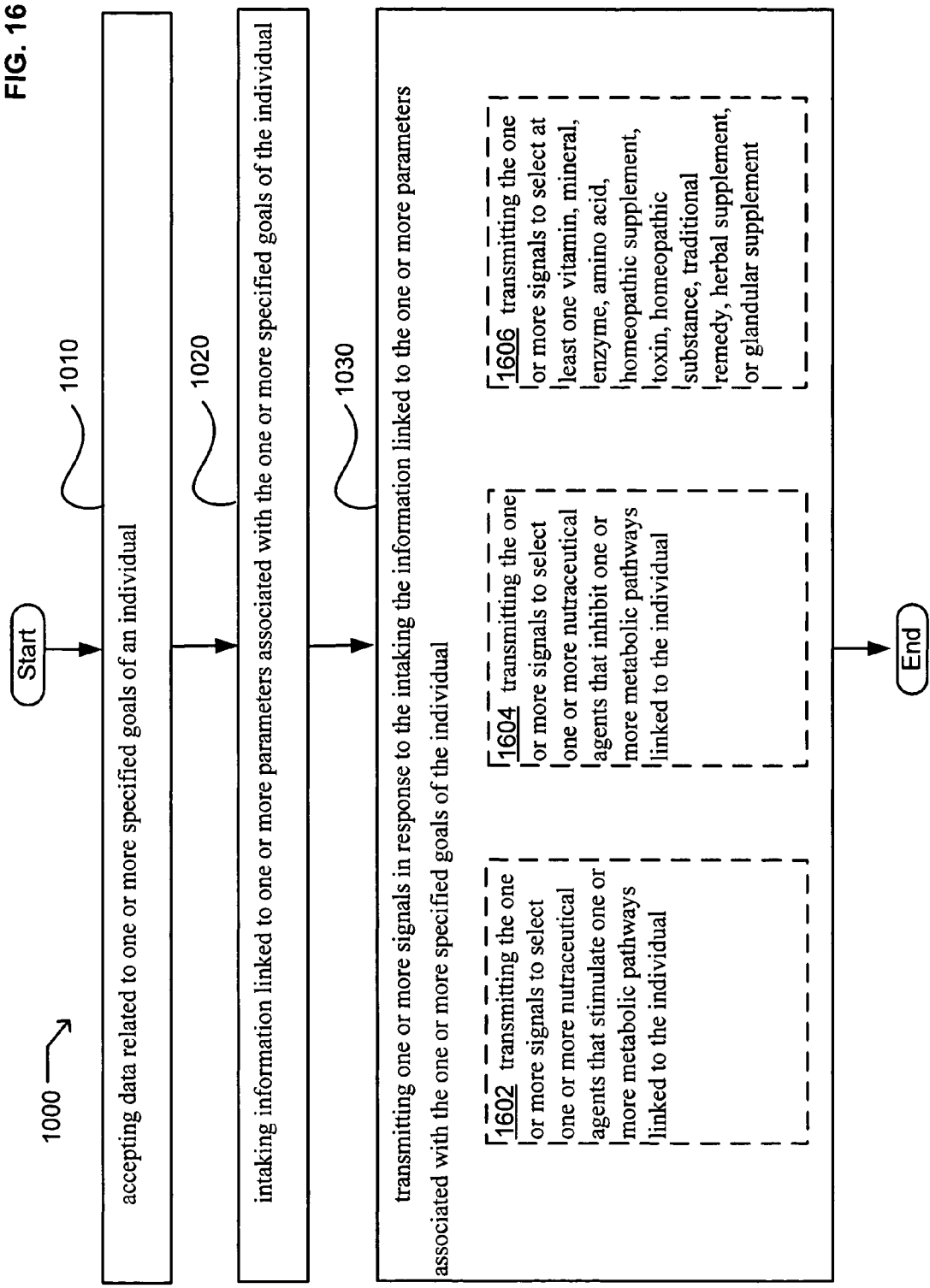
FIG. 16 illustrates alternative embodiments of the example operation flow of FIG. 10.

FIG. 16 illustrates alternative embodiments of the example operational flow 1000 of FIG. 10. FIG. 16 illustrates example embodiments where the transmitting operation 1030 may include at least one additional operation. Additional operations may include an operation 1602, an operation 1604, and/or an operation 1606.

At operation 1602, the transmitting operation 1030 may include transmitting the one or more signals to select one or more nutraceutical agents that stimulate one or more metabolic pathways linked to the individual. In some embodiments, one or more transmitting units 128 transmit one or more signals 130 to select one or more nutraceutical agents 118 that stimulate one or more metabolic pathways linked to the individual 108.

In some embodiments, one or more transmitting units 128 can transmit one or more signals 130 to select one or more nutraceutical agents 118 that stimulate one or more metabolic pathways associated with one or more specified goals 106 of an individual 108. For example, in some embodiments, decline in L-carnitine synthesis is thought to be linked to senile reduction in bone synthesis (Colucci et al., Calcified Tissue International, 76:458-465 (2005)). Dihydroepiandrosterone (DHEA) is thought to affect levels of L-carnitine through promoting the expression of carnitine-synthesizing enzymes (Chiu et al., Calcified Tissue International, 64:527-533 (1999)). Accordingly, in some embodiments, one or more transmitting units 128 can transmit one or more signals 130 to select DHEA to stimulate the L-carnitine synthetic pathway to reduce senile reduction in bone synthesis. In other embodiments, one or more transmitting units 128 can transmit one or more signals 130 to select buckwheat extract to lower blood glucose through activation of mitogen activated protein kinase via phospholipase D (Appleton and Lockwood, The Pharmaceutical Journal, 277:78-83 (2006)). In another embodiment, resveratrol has been shown to stimulate endothelial nitric oxide synthase activity (Klinge et al., J. Biol. Chem., 280(9):7460-7468 (2005); Wallerath et al., Circulation, 106(13):1652-1658 (2002)). Endothelial nitric oxide synthase is an enzyme that catalyzes the formation of nitric oxide by vascular endothelial cells. Nitric oxide is needed to maintain arterial relaxation (vasodilation), and impaired nitric oxide-dependent vasodilation is associated with increased risk of cardiovascular disease (Duffy and Vita, Curr. Opin. Lipidol., 14(1):21-27 (2003)). Accordingly, in some embodiments, one or more transmitting units 128 transmit one or more signals 130 to select resveratrol to reduce cardiovascular disease. One or more transmitting units 128 can transmit one or more signals 130 to select numerous types of nutraceutical agents 118 to stimulate one or more metabolic pathways linked to the individual 108.

At operation 1604, the transmitting operation 1030 may include transmitting the one or more signals to select one or more nutraceutical agents that inhibit one or more metabolic pathways linked to the individual. In some embodiments, one or more transmitting units 128 transmit one or more signals 130 to select one or more nutraceutical agents 118 that inhibit one or more metabolic pathways linked to the individual 108.

In some embodiments, one or more transmitting units 128 can transmit one or more signals 130 to select one or more nutraceutical agents 118 that inhibit one or more enzymes that participate within a metabolic pathway. Such metabolic pathways may be involved with a specified goal 106 of an individual 108. For example, angiotensin-converting enzyme has been linked to high blood pressure. Flavonoids have been shown to inhibit angiotensin-converting enzyme (Actis-Goretta et al., J. Agric. Food Chem., 54(1):229-234 (2006)). Accordingly, in some embodiments, one or more transmitting units 128 can transmit one or more signals 130 to select flavonoids to assist in the reduction of blood pressure (Li et al., Chin. J. Physiol., 48(2):101-106 (2005); Machha and Mustafa, J. Cardiovasc. Pharmacol., 46(1):36-40 (2005)). Genistein, one of the predominant soy isoflavones, has been shown to compete with 17beta-estradiol for estrogen receptor binding because of its structural similarity, resulting in agonistic or antagonistic activity. This has been shown to cause inhibition of cell growth in breast and prostate cancers in vivo and in vitro. Accordingly, in some embodiments, one or more transmitting units 128 can transmit one or more signals 130 to select soy isoflavones containing genistein as a nutraceutical agent 118 for cancer chemoprevention (Sarkar et al., Mini Rev. Med. Chem., 6(4):401-407 (2006)). The isoflavonoids, daidzin, daidzein, and puerarin have been shown to reduce alcohol consumption (Lin R C, Alcohol Clin. Exp. Res., 20(4):659-663 (1996)). A link between daidzin's capacity to reduce alcohol consumption and its ability to increase the liver mitochondrial monoamine oxidase:aldehyde dehydrogenase activity ratio has been established (Keung, Med. Res. Rev., 23(6):669-696 (2003)). This increase in ratio is thought to occur through inhibition of aldehyde dehydrogenase activity. Accordingly, in some embodiments, one or more transmitting units 128 can transmit one or more signals 130 to select isoflavonoid mixtures that include daidzin, daidzein, and/or puerarin to lower alcohol consumption. One or more transmitting units 128 can transmit one or more signals 130 to select numerous other types of nutraceutical agents 118 that inhibit one or more metabolic pathways linked to the individual 108.

At operation 1606, the transmitting operation 1030 may include transmitting the one or more signals to select at least one vitamin, mineral, enzyme, amino acid, homeopathic supplement, toxin, homeopathic substance, traditional remedy, herbal supplement, or glandular supplement. In some embodiments, one or more transmitting units 128 transmit one or more signals 130 to select at least one vitamin, mineral, enzyme, amino acid, homeopathic supplement, toxin, homeopathic substance, traditional remedy, herbal supplement, or glandular supplement.

Figure 17:
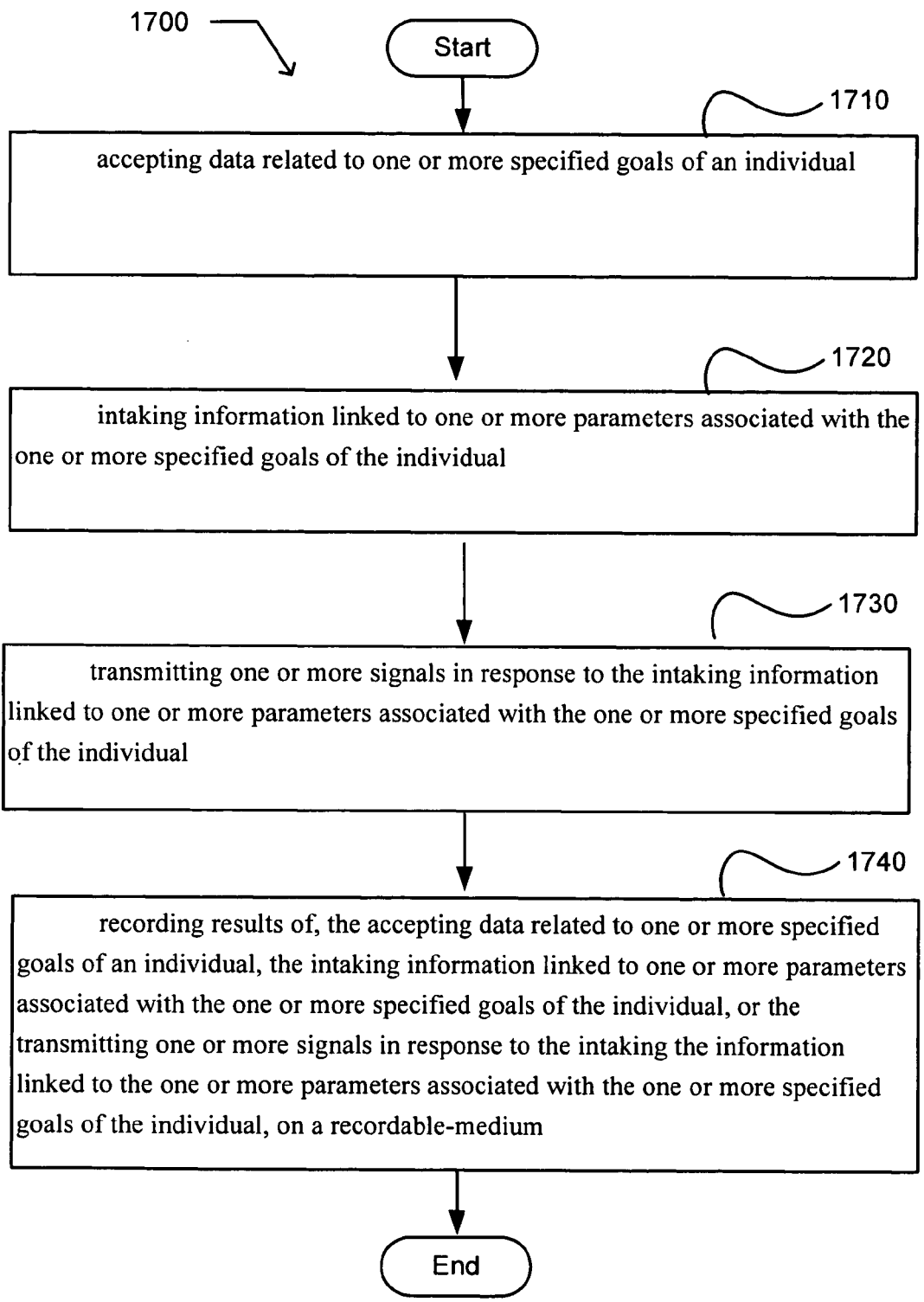
FIG. 17 illustrates an operational flow 1700 representing example operations related to methods for nutraceutical agent selection and dosing.

FIG. 17 illustrates an operational flow 1700 that includes an accepting operation 1710, an intaking operation 1720, and a transmitting operation 1730 (which correspond to the accepting operation 1010, the intaking operation 1020, and the transmitting operation 1030 illustrated in FIG. 10) with an additional recording operation 1740. In FIG. 17, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 1700 includes the operations 1710, 1720, and 1730 (which correspond to operations 1010, 1020, and 1030 as described with regard to FIG. 10) and an additional recording operation 1740 involving recording results of, the accepting data related to one or more specified goals of an individual, the intaking information linked to one or more parameters associated with the one or more specified goals of the individual, or the transmitting one or more signals in response to the intaking the information linked to the one or more parameters associated with the one or more specified goals of the individual, on a recordable-medium. In some embodiments, one or more recording units 124 may record results of, the accepting data 104 related to one or more specified goals 106 of an individual 108, the intaking information 112 linked to one or more parameters 114 associated with the one or more specified goals 106 of the individual 108, or the transmitting one or more signals 130 in response to the intaking information 112 linked to one or more parameters 114 associated with the one or more specified goals 106 of the individual 108, on a recordable-medium 126.

Figure 18:
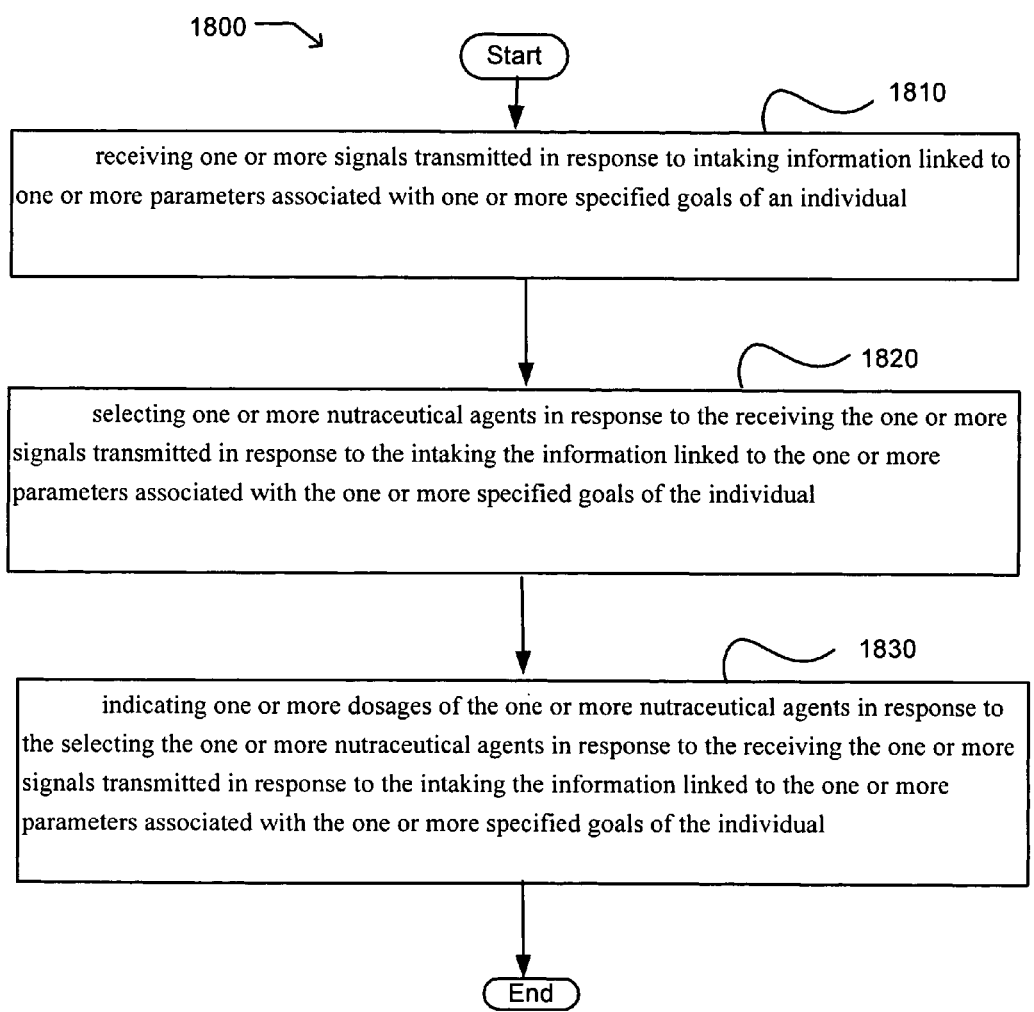
FIG. 18 illustrates an operational flow 1800 representing example operations related to methods for nutraceutical agent selection and dosing.

FIG. 18 illustrates an operational flow 1800 representing examples of operations that are related to the performance of a method for nutraceutical agent 118 and dosing. In FIG. 18 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 1800 includes a receiving operation 1810 involving receiving one or more signals transmitted in response to intaking information linked to one or more parameters associated with one or more specified goals of an individual. In some embodiments, one or more receiving units 132 receive one or more signals 130 transmitted in response to intaking information 112 linked to one or more parameters 114 associated with one or more specified goals 106 of the individual 108.

In some embodiments, one or more receiving units 132 may receive one or more signals 130 that include data 104 related to one or more specified goals 106 of an individual 108. In some embodiments, one or more receiving units 132 receive one or more signals 130 indicating one or more levels of one or more metabolic indicators linked to the individual 108. In some embodiments, one or more receiving units 132 receive one or more signals 130 indicating one or more metabolic activities linked to the individual 108. In some embodiments, one or more receiving units 132 receive one or more signals 130 indicating one or more levels of one or more nutraceutical agents 118 linked to the individual 108. In some embodiments, one or more receiving units 132 receive one or more signals 130 indicating one or more levels of one or more pharmaceutical agents linked to the individual 108. In some embodiments, one or more receiving units 132 receive one or more parameters 114 associated with the one or more specified goals 106 of the individual 108. In some embodiments, one or more receiving units 132 receive one or more instructions to select one or more nutraceutical agents 118 in response to the intaking information 112 linked to one or more parameters 114 associated with the one or more specified goals 106 of the individual 108. In some embodiments, one or more receiving units 132 receive one or more signals 130 to select one or more nutraceutical agents 118 to increase one or more levels of one or more components associated with the one or more specified goals 106 of the individual 108. In some embodiments, one or more receiving units 132 receive one or more signals 130 to select one or more nutraceutical agents 118 to decrease one or more levels of one or more components associated with the one or more specified goals 106 of the individual 108. In some embodiments, one or more receiving units 132 receive one or more signals 130 to select one or more nutraceutical agents 118 that stimulate one or more metabolic pathways linked to the individual 108. In some embodiments, one or more receiving units 132 receive one or more signals 130 to select one or more nutraceutical agents 118 that inhibit one or more metabolic pathways linked to the individual 108. In some embodiments, one or more receiving units 132 receive one or more signals 130 to select at least one vitamin, mineral, enzyme, amino acid, homeopathic supplement, toxin, homeopathic substance, traditional remedy, herbal supplement, glandular supplement, or substantially any combination thereof.

In some embodiments, one or more receiving units 132 may receive one or more signals 130 that include data 104 related to one or more specified goals 106 of an individual 108. One or more receiving units 132 may receive one or more signals 130 through use of numerous technologies. Examples of such technologies include, but are not limited to, wireless transmission, telephone, internet transmission, digital transmission, analog transmission, optical transmission, and the like.

After a start operation, the operational flow 1800 includes a selecting operation 1820 involving selecting one or more nutraceutical agents in response to the receiving the one or more signals transmitted in response to the intaking the information linked to the one or more parameters associated with the one or more specified goals of the individual. In some embodiments, one or more selecting units 116 select one or more nutraceutical agents 118 in response to the receiving one or more signals 130 transmitted in response to intaking information 112 linked to one or more parameters 114 associated with one or more specified goals 106 of the individual 108.

In some embodiments, one or more selecting units 116 may select one or more nutraceutical agents 118 in response to the intaking information 112 linked to one or more parameters 114 associated with the one or more specified goals 106 of the individual 108. In some embodiments, one or more selecting units 116 may select one or more nutraceutical agents 118 in response to one or more intaking units 110. In some embodiments, one or more selecting units 116 may select one or more nutraceutical agents 118 in response to one or more accepting units 102. In some embodiments, one or more selecting units 116 may select one or more nutraceutical agents 118 in response to one or more intaking units 110 and one or more accepting units 102. Accordingly, in some embodiments, one or more selecting units 116 may select one or more nutraceutical agents 118 with regard to one or more characteristics of the individual 108 and one or more parameters 114 associated with one or more specified goals 106 of the individual 108. For example, in some embodiments, one or more selecting units 116 may select one or more nutraceutical agents 118 based on the age of the individual 108 and the level of testosterone in the individual's 108 blood. In other embodiments, one or more selecting units 116 may select one or more nutraceutical agents 118 based on insurance coverage held by an individual 108 and a specified goal 106 of the individual 108. Accordingly, numerous combinations of information 112 and data 104 may be used by one or more selecting units 116 to select one or more nutraceutical agents 118.

After a start operation, the operational flow 1800 includes an indicating operation 1830 involving indicating one or more dosages of the one or more nutraceutical agents in response to the selecting the one or more nutraceutical agents in response to the receiving the one or more signals transmitted in response to the intaking the information linked to the one or more parameters associated with the one or more specified goals of the individual. In some embodiments, one or more indicating units 120 indicate one or more dosages 122 of the one or more nutraceutical agents 118 in response to the selecting one or more nutraceutical agents 118 in response to the receiving one or more signals 130 transmitted in response to intaking information 112 linked to one or more parameters 114 associated with one or more specified goals 106 of the individual 108.

In some embodiments, one or more indicating units 120 may indicate one or more dosages 122 of the one or more nutraceutical agents 118 in response to the intaking information 112 linked to one or more parameters 114 associated with the one or more specified goals 106 of the individual 108. In some embodiments, one or more indicating units 120 may indicate one or more dosages 122 of one or more nutraceutical agents 118 in human-readable format. In some embodiments, one or more indicating units 120 may indicate one or more dosages 122 of one or more nutraceutical agents 118 in machine-readable format. In some embodiments, one or more indicating units 120 may deposit one or more dosages 122 of one or more nutraceutical agents 118 on one or more labels. In some embodiments, one or more indicating units 120 may dispense one or more nutraceutical agents 118. In some embodiments, one or more indicating units 120 may dispense one or more nutraceutical agents 118 in unit dosage form. In some embodiments, one or more indicating units 120 may dispense two or more of one or more nutraceutical agents 118 in a single administration form.

Figure 19:
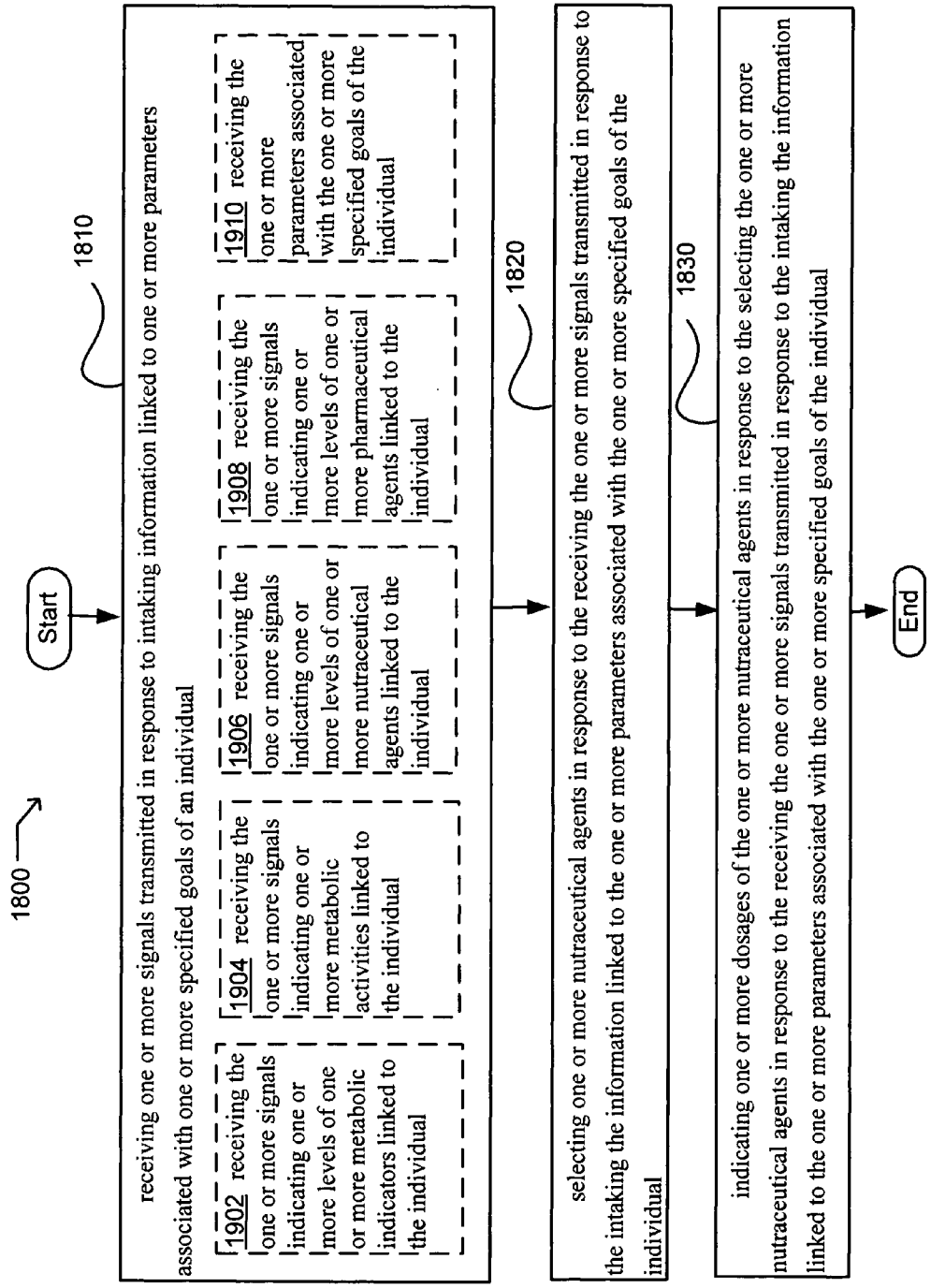
FIG. 19 illustrates alternative embodiments of the example operation flow of FIG. 18.

FIG. 19 illustrates alternative embodiments of the example operational flow 1800 of FIG. 18. FIG. 19 illustrates example embodiments where the receiving operation 1810 may include at least one additional operation. Additional operations may include an operation 1902, an operation 1904, an operation 1906, an operation 1908, and/or an operation 1910.

At operation 1902, the receiving operation 1810 may include receiving the one or more signals indicating one or more levels of one or more metabolic indicators linked to the individual. In some embodiments, one or more receiving units 132 receive one or more signals 130 indicating one or more levels of one or more metabolic indicators linked to the individual 108.

In some embodiments, one or more receiving units 132 may receive one or more signals 130 indicating the levels of homocysteine and methylmalonic acid to indicate levels of vitamin $B_{12}$ and folate within an individual 108. In some embodiments, one or more receiving units 132 may receive one or more signals 130 indicating the level of albumin as an indirect measure of vitamin A levels. In some embodiments, one or more receiving units 132 may receive one or more signals 130 indicating the level of a metabolic indicator directly. For example, in some embodiments, one or more receiving units 132 may receive one or more signals 130 indicating vitamin A concentration, pH, magnesium concentration, calcium concentration, and the like. One or more receiving units 132 may receive one or more signals 130 indicating the level of numerous metabolic indicators.

At operation 1904, the receiving operation 1810 may include receiving the one or more signals indicating one or more metabolic activities linked to the individual. In some embodiments, one or more receiving units 132 receive one or more signals 130 indicating one or more metabolic activities linked to the individual 108.

In some embodiments, one or more receiving units 132 can be used to receive one or more signals 130 that indicate the level of one or more enzyme activities of an individual 108. For example, in some embodiments, one or more receiving units 132 can receive one or more signals 130 that indicate the level of a protease activity of an individual 108. In some embodiments, one or more receiving units 132 can receive one or more signals 130 that indicate the level of Protein Induced by Vitamin K Absence (PIVKA-II) to indicate vitamin K deficiency or adequacy of an individual 108. One or more receiving units 132 may receive one or more signals 130 that indicate the level of numerous metabolic activities linked to an individual 108.

At operation 1906, the receiving operation 1810 may include receiving the one or more signals indicating one or more levels of one or more nutraceutical agents linked to the individual. In some embodiments, one or more receiving units 132 receive one or more signals 130 indicating one or more levels of one or more nutraceutical agents 118 linked to the individual 108.

In some embodiments, one or more receiving units 132 can receive one or more signals 130 indicating one or more levels of one or more nutraceutical agents 118 that were determined at one or more times. For example, in some embodiments, one or more signals 130 indicating the level of a nutraceutical agent 118 at the time when administered to an individual 108, at time two hours post-administration, at time four hours post-administration, and at time six hours post-administration may be received. Accordingly, in some embodiments, the rate at which one or more nutraceutical agents 118 are metabolized by an individual 108 may be determined. In some embodiments, the rate at which a level of nutraceutical is reached within an individual 108 may be determined. One or more signals 130 indicating numerous times and concentrations of nutraceutical agents 118 may be received.

At operation 1908, the receiving operation 1810 may include receiving the one or more signals indicating one or more levels of one or more pharmaceutical agents linked to the individual. In some embodiments, one or more receiving units 132 receive one or more signals 130 indicating one or more levels of one or more pharmaceutical agents linked to the individual 108.

In some embodiments, one or more receiving units 132 can receive one or more signals 130 indicating one or more levels of one or more pharmaceutical agents that were determined at one or more times. For example, in some embodiments, one or more signals 130 indicating the level of a pharmaceutical agent at the time when administered to an individual 108, at time two hours post-administration, at time four hours post-administration, and at time six hours post-administration may be received. Accordingly, in some embodiments, the rate at which one or more pharmaceutical agents are metabolized by an individual 108 may be determined. In some embodiments, the rate at which a level of a pharmaceutical agent is reached within an individual 108 may be determined. One or more signals 130 indicating numerous times and concentrations of pharmaceutical agents may be received.

At operation 1910, the receiving operation 1810 may include receiving the one or more parameters associated with the one or more specified goals of the individual. In some embodiments, one or more receiving units 132 receive one or more parameters 114 associated with the one or more specified goals 106 of the individual 108.

One or more receiving units 132 can receive one or more signals 130 indicating numerous parameters 114 that are associated with one or more specified goals 106 of an individual 108. Examples of such parameters 114 include, but are not limited to, blood sugar levels, blood insulin levels, blood iron levels, hormone levels, nutraceutical agent 118 levels, pharmaceutical agent levels, cytokine levels, and the like (i.e., Fitzgerald et al., The Cytokine Facts Book, Academic Press, San Francisco, Second Edition, (2001)).

Figure 20:
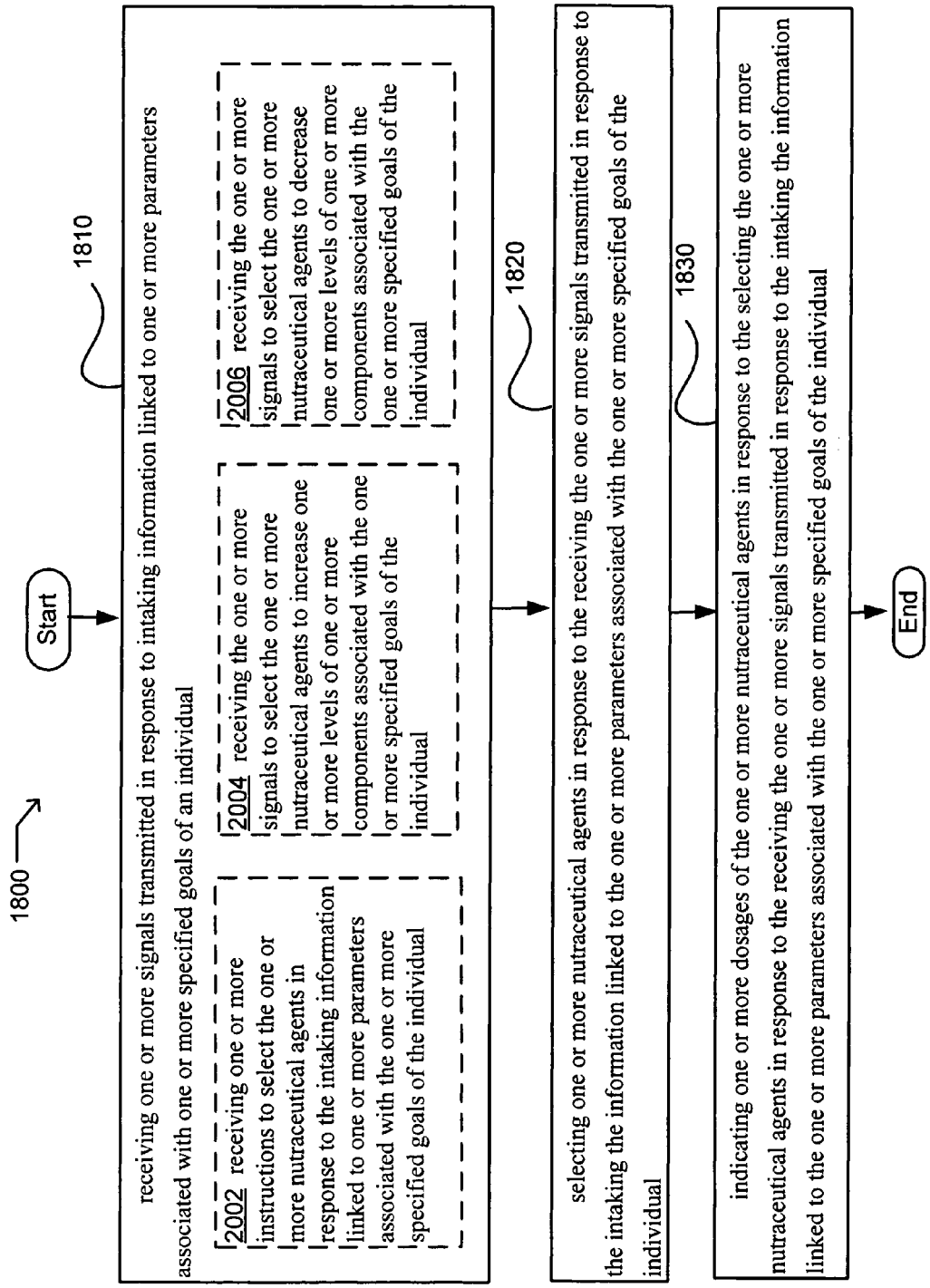
FIG. 20 illustrates alternative embodiments of the example operation flow of FIG. 18.

FIG. 20 illustrates alternative embodiments of the example operational flow 1800 of FIG. 18. FIG. 20 illustrates example embodiments where the receiving operation 1810 may include at least one additional operation. Additional operations may include an operation 2002, an operation 2004, and/or an operation 2006.

At operation 2002, the receiving operation 1810 may include receiving one or more instructions to select the one or more nutraceutical agents in response to the intaking information linked to one or more parameters associated with the one or more specified goals of the individual. In some embodiments, one or more receiving units 132 receive one or more instructions to select one or more nutraceutical agents 118 in response to the intaking information 112 linked to one or more parameters 114 associated with the one or more specified goals 106 of the individual 108.

In some embodiments, one or more receiving units 132 receive one or more signals 130 that include one or more instructions to select one or more nutraceutical agents 118 in response to accepting data 104 related to one or more specified goals 106 of an individual 108. One or more receiving units 132 can receive one or more signals 130 that include one or more instructions to select one or more nutraceutical agents 118 based on numerous parameters 114. Examples of such parameters 114 include, but are not limited to, blood sugar levels, blood insulin levels, blood iron levels, hormone levels, nutraceutical agent 118 levels, pharmaceutical agent levels, cytokine levels, and the like.

At operation 2004, the receiving operation 1810 may include receiving the one or more signals to select the one or more nutraceutical agents to increase one or more levels of one or more components associated with the one or more specified goals of the individual. In some embodiments, one or more receiving units 132 receive one or more signals 130 to select one or more nutraceutical agents 118 to increase one or more levels of one or more components associated with the one or more specified goals 106 of the individual 108.

In some embodiments, one or more receiving units 132 receive one or more signals 130 to select one or more nutraceutical agents 118 that may directly complement one or more levels of one or more components associated with one or more specified goals 106 of the individual 108. For example, in some embodiments, one or more receiving units 132 receive one or more signals 130 to select calcium in various forms (i.e., calcium citrate, calcium aspartate, calcium carbonate) to avoid or reduce the effects of osteoporosis. In another embodiment, one or more receiving units 132 receive one or more signals 130 to select chromium to lower blood sugar, increase insulin sensitivity, reduce body fat, control hunger, suppress appetite, increase lean body/muscle mass, or substantially any combination thereof. In some embodiments, one or more receiving units 132 receive one or more signals 130 to select one or more nutraceutical agents 118 to indirectly supplement a component associated with one or more specified goals 106 of an individual 108. For example, one or more receiving units 132 may receive one or more signals 130 to select 5-hydroxy-tryptophan for administration to an individual 108 if the individual 108 suffers from depression and is found to exhibit low levels of serotonin. Numerous signals 130 may be received to select one or more nutraceutical agents 118 to increase one or more levels of one or more components associated with one or more specified goals 106 of an individual 108.

At operation 2006, the receiving operation 1810 may include receiving the one or more signals to select the one or more nutraceutical agents to decrease one or more levels of one or more components associated with the one or more specified goals of the individual. In some embodiments, one or more receiving units 132 receive one or more signals 130 to select one or more nutraceutical agents 118 to decrease one or more levels of one or more components associated with the one or more specified goals 106 of the individual 108.

Low density lipoproteins are examples of components that are linked to vascular disease. Accordingly, in some embodiments, one or more receiving units 132 may receive one or more signals 130 to select one or more nutraceutical agents 118 that will act to lower the low density lipoprotein concentration of an individual 108. Examples of such nutraceutical agents 118 include, but are not limited to, plant stanols, dietary fiber, stanol esters, isoflavones, diallyl sulfides, niacin, soy protein, and substantially any combination thereof. Glucose is an example of a component that is linked to hyperglycemia. Accordingly, in some embodiments, one or more receiving units 132 may receive one or more signals 130 to select buckwheat to lower blood glucose levels of an individual 108. Free radical oxygen species that include singlet oxygen, hydroxyl radicals, peroxides, and superoxide radicals are components that act to damage lipids and other cellular structures. Accordingly, in some embodiments, one or more receiving units 132 may receive one or more signals 130 to select one or more nutraceutical agents 118 to reduce levels of free radicals within an individual 108. Examples of such nutraceutical agents 118 include, but are not limited to, terpenes, carotenoids, limonoids, phenols, flavonoids, isoprenoids, and the like. One or more receiving units 132 can receive one or more signals 130 to select numerous types of nutraceutical agents 118 to decrease one or more levels of one or more components associated with the one or more specified goals 106 of the individual 108.

Figure 21:
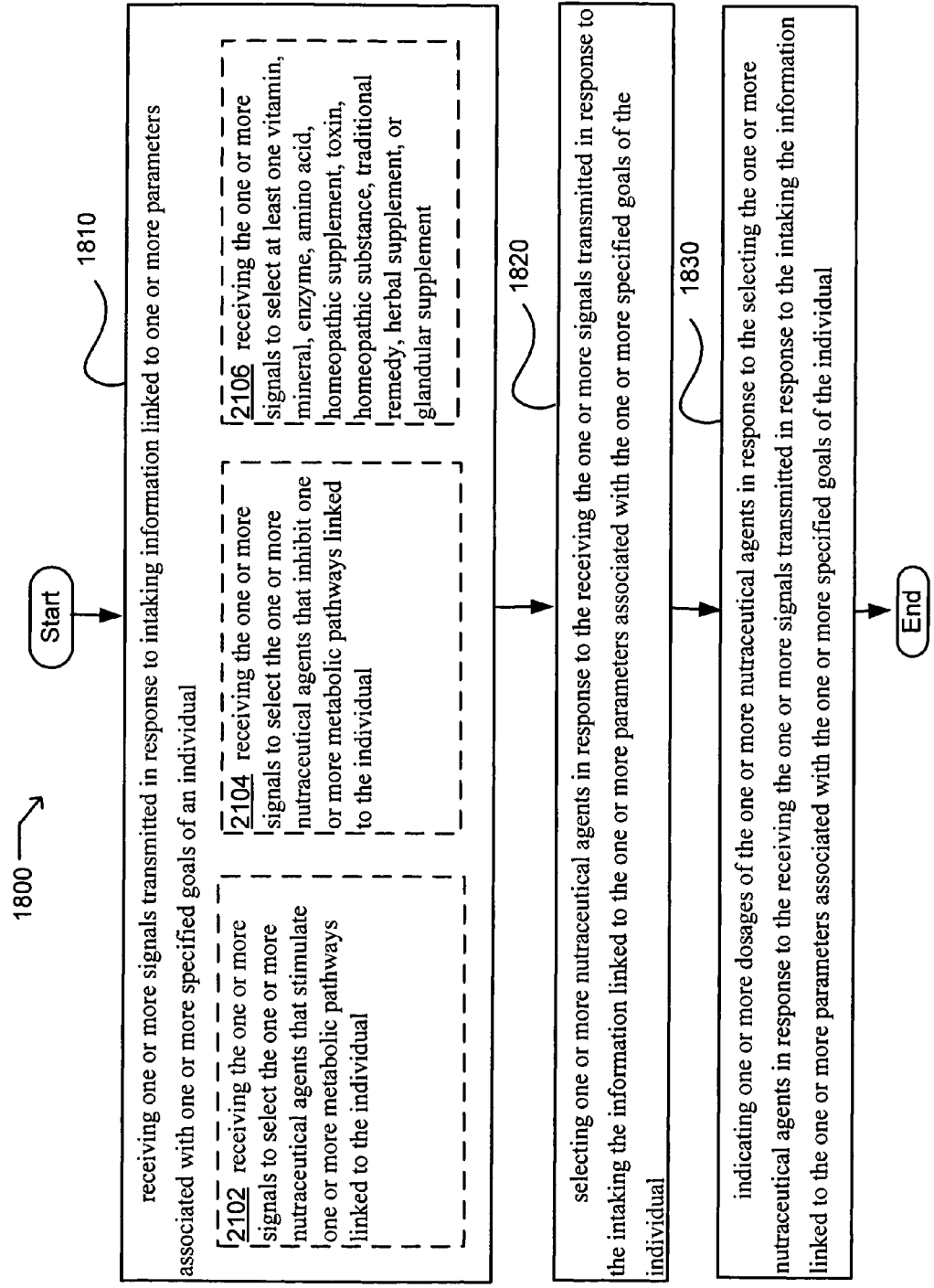
FIG. 21 illustrates alternative embodiments of the example operation flow of FIG. 18.

FIG. 21 illustrates alternative embodiments of the example operational flow 1800 of FIG. 18. FIG. 21 illustrates example embodiments where the receiving operation 1810 may include at least one additional operation. Additional operations may include an operation 2102, an operation 2104, and/or an operation 2106.

At operation 2102, the receiving operation 1810 may include receiving the one or more signals to select the one or more nutraceutical agents that stimulate one or more metabolic pathways linked to the individual. In some embodiments, one or more receiving units 132 receive one or more signals 130 to select one or more nutraceutical agents 118 that stimulate one or more metabolic pathways linked to the individual 108.

In some embodiments, one or more receiving units 132 can receive one or more signals 130 to select one or more nutraceutical agents 118 that stimulate one or more metabolic pathways associated with one or more specified goals 106 of an individual 108. For example, in some embodiments, decline in L-carnitine synthesis is thought to be linked to senile reduction in bone synthesis (Colucci et al., Calcified Tissue International, 76:458-465 (2005)). Dihydroepiandrosterone (DHEA) is thought to affect levels of L-carnitine through promoting the expression of carnitine-synthesizing enzymes (Chiu et al., Calcified Tissue International, 64:527-533 (1999)). Accordingly, in some embodiments, one or more receiving units 132 can receive one or more signals 130 to select DHEA to stimulate the L-carnitine synthetic pathway to reduce senile reduction in bone synthesis. In other embodiments, one or more receiving units 132 can receive one or more signals 130 to select buckwheat extract to lower blood glucose through activation of mitogen activated protein kinase via phospholipase D (Appleton and Lockwood, The Pharmaceutical Journal, 277:78-83 (2006)). In another embodiment, resveratrol has been shown to stimulate endothelial nitric oxide synthase activity (Klinge et al., J. Biol. Chem., 280(9):7460-7468 (2005); Wallerath et al., Circulation, 106(13):1652-1658 (2002)). Endothelial nitric oxide synthase is an enzyme that catalyzes the formation of nitric oxide by vascular endothelial cells. Nitric oxide is needed to maintain arterial relaxation (vasodilation), and impaired nitric oxide-dependent vasodilation is associated with increased risk of cardiovascular disease (Duffy and Vita, Curr. Opin. Lipidol., 14(1):21-27 (2003)). Accordingly, in some embodiments, one or more receiving units 132 receive one or more signals 130 to select resveratrol to reduce cardiovascular disease. One or more receiving units 132 can receive one or more signals 130 to select numerous types of nutraceutical agents 118 to stimulate one or more metabolic pathways linked to the individual 108.

At operation 2104, the receiving operation 1810 may include receiving the one or more signals to select the one or more nutraceutical agents that inhibit one or more metabolic pathways linked to the individual. In some embodiments, one or more receiving units 132 receive one or more signals 130 to select one or more nutraceutical agents 118 that inhibit one or more metabolic pathways linked to the individual 108.

In some embodiments, one or more receiving units 132 can receive one or more signals 130 to select one or more nutraceutical agents 118 that inhibit one or more enzymes that participate within a metabolic pathway. Such metabolic pathways may be involved with a specified goal 106 of an individual 108. For example, angiotensin-converting enzyme has been linked to high blood pressure. Flavonoids have been shown to inhibit angiotensin-converting enzyme (Actis-Goretta et al., J. Agric. Food Chem., 54(1):229-234 (2006)). Accordingly, in some embodiments, one or more receiving units 132 can receive one or more signals 130 to select flavonoids to assist in the reduction of blood pressure (Li et al., Chin. J. Physiol., 48(2):101-106 (2005); Machha and Mustafa, J. Cardiovasc. Pharmacol., 46(1):36-40 (2005)). Genistein, one of the predominant soy isoflavones, has been shown to compete with 17beta-estradiol for estrogen receptor binding because of its structural similarity, resulting in agonistic or antagonistic activity. This has been shown to cause inhibition of cell growth in breast and prostate cancers in vivo and in vitro. Accordingly, in some embodiments, one or more receiving units 132 can receive one or more signals 130 to select soy isoflavones containing genistein as a nutraceutical agent 118 for cancer chemoprevention (Sarkar et al., Mini Rev. Med. Chem., 6(4):401-407 (2006)). The isoflavonoids, daidzin, daidzein, and puerarin have been shown to reduce alcohol consumption (Lin R C, Alcohol Clin. Exp. Res., 20(4):659-663 (1996)). A link between daidzin's capacity to reduce alcohol consumption and its ability to increase the liver mitochondrial monoamine oxidase:aldehyde dehydrogenase activity ratio has been established (Keung, Med. Res. Rev., 23(6):669-696 (2003)). This increase in ratio is thought to occur through inhibition of aldehyde dehydrogenase activity. Accordingly, in some embodiments, one or more receiving units 132 can receive one or more signals 130 to select isoflavonoid mixtures that include daidzin, daidzein, and/or puerarin to lower alcohol consumption. One or more receiving units 132 can receive one or more signals 130 to select numerous other types of nutraceutical agents 118 that inhibit one or more metabolic pathways linked to the individual 108.

At operation 2106, the receiving operation 1810 may include receiving the one or more signals to select at least one vitamin, mineral, enzyme, amino acid, homeopathic supplement, toxin, homeopathic substance, traditional remedy, herbal supplement, or glandular supplement. In some embodiments, one or more receiving units 132 receive one or more signals 130 to select at least one vitamin, mineral, enzyme, amino acid, homeopathic supplement, toxin, homeopathic substance, traditional remedy, herbal supplement, or glandular supplement.

Figure 22:
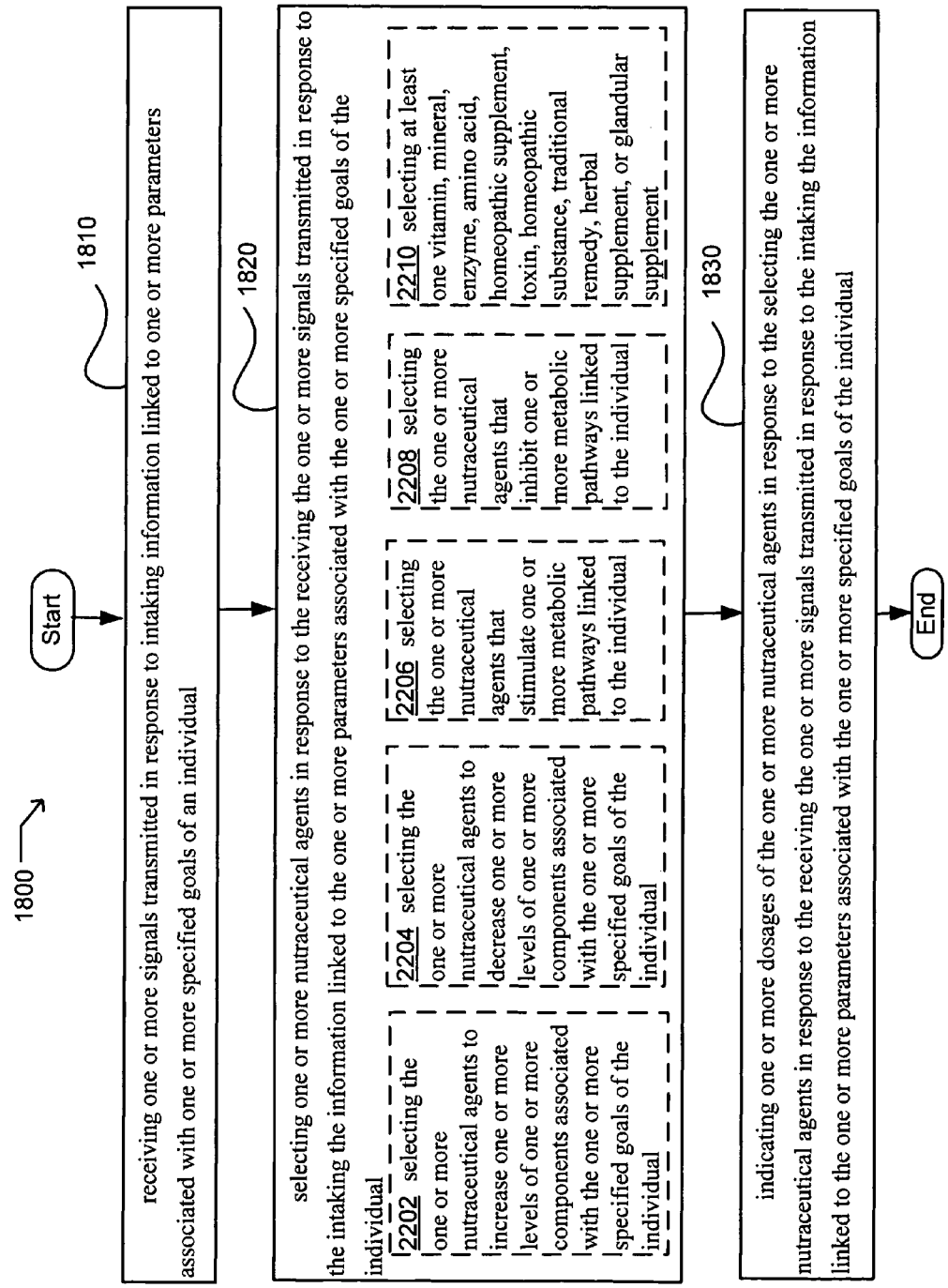
FIG. 22 illustrates alternative embodiments of the example operation flow of FIG. 18.

FIG. 22 illustrates alternative embodiments of the example operational flow 1800 of FIG. 18. FIG. 22 illustrates example embodiments where the selecting operation 1820 may include at least one additional operation. Additional operations may include an operation 2202, an operation 2204, an operation 2206, an operation 2208, and/or an operation 2210.

At operation 2202, the selecting operation 1820 may include selecting the one or more nutraceutical agents to increase one or more levels of one or more components associated with the one or more specified goals of the individual. In some embodiments, one or more receiving units 132 select one or more nutraceutical agents 118 to increase one or more levels of one or more components associated with the one or more specified goals 106 of the individual 108.

In some embodiments, one or more nutraceutical agents 118 may be selected that may directly complement one or more levels of one or more components associated with one or more specified goals 106 of the individual 108. For example, calcium in various forms (i.e., calcium citrate, calcium aspartate, calcium carbonate) may be selected by an individual 108 who wants to avoid or reduce the effects of osteoporosis. In another embodiment, chromium may be selected to lower blood sugar, increase insulin sensitivity, reduce body fat, control hunger, suppress appetite, increase lean body/muscle mass, or substantially any combination thereof. In some embodiments, one or more nutraceutical agents 118 associated with one or more specified goals 106 of an individual 108 may be selected that may be administered to an individual 108 to indirectly supplement a component associated with the one or more specified goals 106. For example, 5-hydroxy-tryptophan may be selected for administration to an individual 108 if the individual 108 suffers from depression and is found to exhibit low levels of serotonin. The 5-hydroxy-tryptophan will be converted to serotonin following administration to the individual 108. Numerous nutraceutical agents 118 may be selected to increase one or more levels of one or more components associated with one or more specified goals 106 of an individual 108.

At operation 2204, the selecting operation 1820 may include selecting the one or more nutraceutical agents to decrease one or more levels of one or more components associated with the one or more specified goals of the individual. In some embodiments, one or more receiving units 132 select one or more nutraceutical agents 118 to decrease one or more levels of one or more components associated with the one or more specified goals 106 of the individual 108.

In some embodiments, one or more components may be associated with one or more specified goals 106 of an individual 108. Low density lipoproteins are examples of components that are linked to vascular disease. Accordingly, in some embodiments, one or more nutraceutical agents 118 may be selected that will act to lower the low density lipoprotein concentration of an individual 108. Examples of such nutraceutical agents 118 include, but are not limited to, plant stanols, dietary fiber, stanol esters, isoflavones, diallyl sulfides, niacin, soy protein, and substantially any combination thereof. Glucose is an example of a component that is linked to hyperglycemia. Accordingly, in some embodiments, buckwheat is an example of a nutraceutical agent 118 that may be selected to lower blood glucose levels of an individual 108. Free radical oxygen species that include singlet oxygen, hydroxyl radicals, peroxides, and superoxide radicals are components that act to damage lipids and other cellular structures. Accordingly, one or more nutraceutical agents 118 may be selected to reduce levels of free radicals within an individual 108. Examples of such nutraceutical agents 118 include, but are not limited to, terpenes, carotenoids, limonoids, phenols, flavonoids, isoprenoids, and the like. Numerous other nutraceutical agents 118 may be selected to decrease one or more levels of one or more components associated with the one or more specified goals 106 of the individual 108.

At operation 2206, the selecting operation 1820 may include selecting the one or more nutraceutical agents that stimulate one or more metabolic pathways linked to the individual. In some embodiments, one or more receiving units 132 select one or more nutraceutical agents 118 that stimulate one or more metabolic pathways linked to the individual 108.

In some embodiments, stimulation of one or more metabolic pathways may be associated with one or more specified goals 106 of an individual 108. For example, in some embodiments, decline in L-carnitine synthesis is thought to be linked to senile reduction in bone synthesis (Colucci et al., Calcified Tissue International, 76:458-465 (2005)). Dihydroepiandrosterone (DHEA) is thought to affect levels of L-carnitine through promoting the expression of carnitine-synthesizing enzymes (Chiu et al., Calcified Tissue International, 64:527-533 (1999)). Accordingly, DHEA may be selected to stimulate the L-carnitine synthetic pathway to reduce senile reduction in bone synthesis. In other embodiments, buckwheat extract may be selected to lower blood glucose due to the ability of buckwheat extract to activate mitogen activated protein kinase via phospholipase D (Appleton and Lockwood, The Pharmaceutical Journal, 277:78-83 (2006)). In another embodiment, resveratrol has been shown to stimulate endothelial nitric oxide synthase activity (Klinge et al., J. Biol. Chem., 280(9):7460-7468 (2005); Wallerath et al., Circulation, 106(13):1652-1658 (2002)). Endothelial nitric oxide synthase is an enzyme that catalyzes the formation of nitric oxide by vascular endothelial cells. Nitric oxide is needed to maintain arterial relaxation (vasodilation), and impaired nitric oxide-dependent vasodilation is associated with increased risk of cardiovascular disease (Duffy and Vita, Curr. Opin. Lipidol., 14(1):21-27 (2003)). Accordingly, in some embodiments, resveratrol may be selected to reduce cardiovascular disease. Numerous nutraceutical agents 118 may be selected to one or more metabolic pathways linked to the individual 108.

At operation 2208, the selecting operation 1820 may include selecting the one or more nutraceutical agents that inhibit one or more metabolic pathways linked to the individual. In some embodiments, one or more receiving units 132 select one or more nutraceutical agents 118 that inhibit one or more metabolic pathways linked to the individual 108.

In some embodiments, one or more metabolic pathways may be inhibited through inhibition of one or more enzymes that participate within the metabolic pathway. Such metabolic pathways may be involved with a specified goal 106 of an individual 108. For example, angiotensin-converting enzyme has been linked to high blood pressure. Flavonoids have been shown to inhibit angiotensin-converting enzyme (Actis-Goretta et al., J. Agric. Food Chem., 54(1):229-234 (2006)). Accordingly, flavonoids may be selected to assist in the reduction of blood pressure (Li et al., Chin. J. Physiol., 48(2): 101-106 (2005); Machha and Mustafa, J. Cardiovasc. Pharmacol., 46(1):36-40 (2005)). Genistein, one of the predominant soy isoflavones, has been shown to compete with 17beta-estradiol for estrogen receptor binding because of its structural similarity, resulting in agonistic or antagonistic activity. This has been shown to cause inhibition of cell growth in breast and prostate cancers in vivo and in vitro. Accordingly, soy isoflavones containing genistein may be selected as a nutraceutical agent 118 for cancer chemoprevention (Sarkar et al., Mini Rev. Med. Chem., 6(4):401-407 (2006)). The isoflavonoids, daidzin, daidzein, and puerarin have been shown to reduce alcohol consumption (Lin R C, Alcohol Clin. Exp. Res., 20(4):659-663 (1996)). A link between daidzin's capacity to reduce alcohol consumption and its ability to increase the liver mitochondrial monoamine oxidase:aldehyde dehydrogenase activity ratio has been established (Keung, Med. Res. Rev., 23(6):669-696 (2003)). This increase in ratio is thought to occur through inhibition of aldehyde dehydrogenase activity. Accordingly, isoflavonoid mixtures that include daidzin, daidzein, and/or puerarin may be selected to lower alcohol consumption. Numerous other nutraceutical agents 118 may be selected that inhibit one or more metabolic pathways linked to the individual 108.

At operation 2210, the selecting operation 1820 may include selecting at least one vitamin, mineral, enzyme, amino acid, homeopathic supplement, toxin, homeopathic substance, traditional remedy, herbal supplement, or glandular supplement. In some embodiments, one or more receiving units 132 select at least one vitamin, mineral, enzyme, amino acid, homeopathic supplement, toxin, homeopathic substance, traditional remedy, herbal supplement, or glandular supplement.

Figure 23:
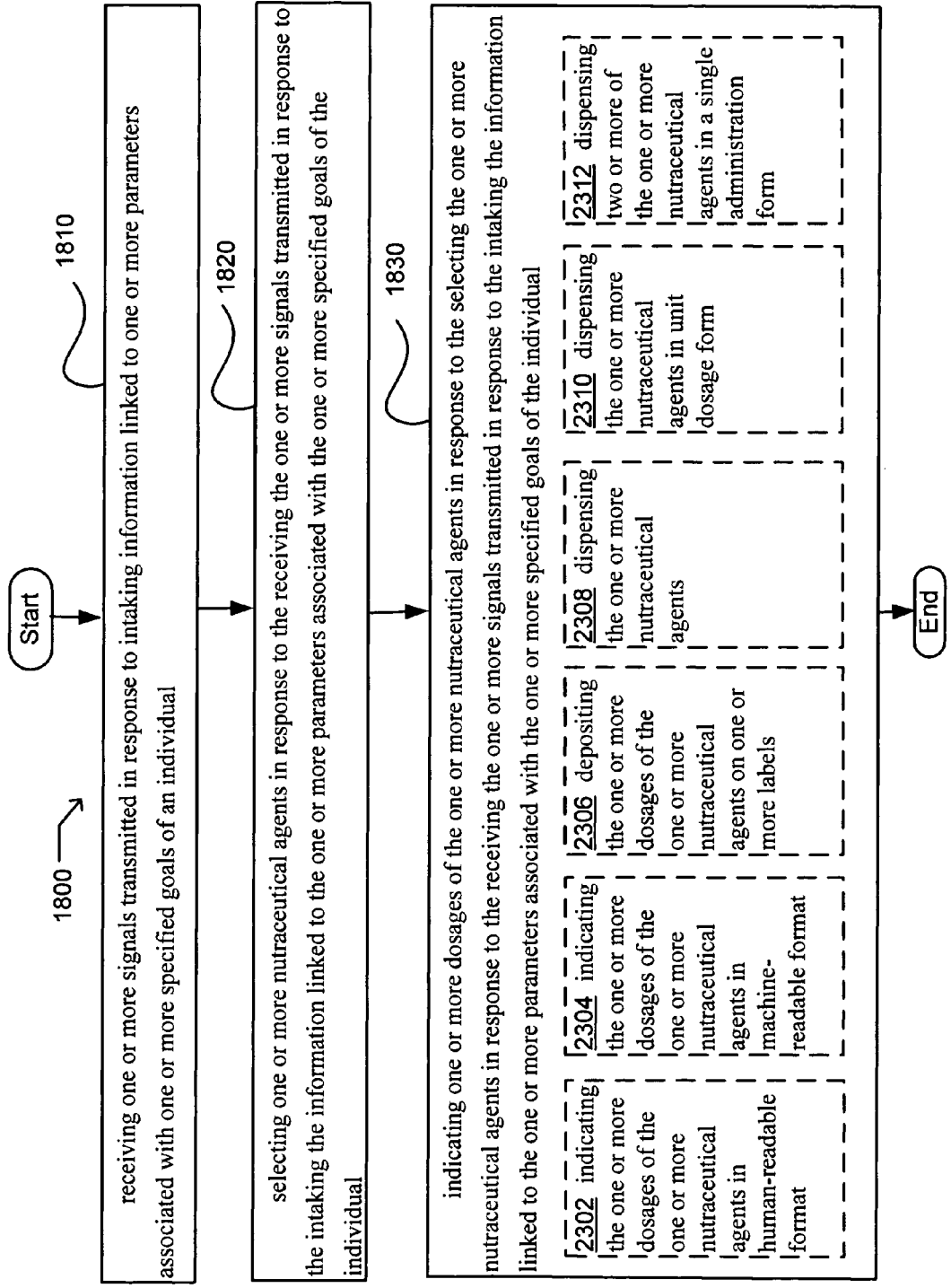
FIG. 23 illustrates alternative embodiments of the example operation flow of FIG. 18.

FIG. 23 illustrates alternative embodiments of the example operational flow 1800 of FIG. 18. FIG. 23 illustrates example embodiments where the indicating operation 1830 may include at least one additional operation. Additional operations may include an operation 2302, an operation 2304, an operation 2306, an operation 2308, an operation 2310, and/or an operation 2312.

At operation 2302, the indicating operation 1830 may include indicating the one or more dosages of the one or more nutraceutical agents in human-readable format. In some embodiments, one or more indicating units 120 indicate the one or more dosages 122 of the one or more nutraceutical agents 118 in human-readable format In some embodiments, one or more indicating units 120 may indicate one or more dosages 122 of one or more nutraceutical agents 118 on a visual display, a touch display, an audible display, and the like. For example, in some embodiments, one or more indicating units 120 may display one or more dosages 122 on a light emitting diode display, a liquid crystal display, various monitors, and the like. Such visual displays may indicate one or more dosages 122 through display of colors, pictures, printed language, and the like. In some embodiments, one or more indicating units 120 may display one or more dosages 122 on a touch display (i.e., a touch pad display in Braille for use by blind or visually impaired persons). In some embodiments, one or more indicating units 120 may display one or more dosages 122 through use of an audible display that verbally speaks to an individual 108.

In some embodiments, one or more indicating units 120 may display one or more dosages 122 of one or more nutraceutical agents 118 in typographical symbols in numerous languages that are in human-readable format. In some embodiments, one or more indicating units 120 may display one or more dosages 122 of one or more nutraceutical agents 118 and the formulation type of the one or more nutraceutical agents 118 in typographical symbols in numerous languages that are in human-readable format. In some embodiments, one or more indicating units 120 may display one or more dosages 122 of one or more nutraceutical agents 118 in pictographic form that is in human-readable format. In some embodiments, one or more indicating units 120 may display one or more dosages 122 of one or more nutraceutical agents 118 and the formulation type of the one or more nutraceutical agents 118 in pictographic form that is in human-readable format. In some embodiments, one or more indicating units 120 may display one or more dosages 122 of one or more nutraceutical agents 118 according to a color scheme that is in human-readable format. In some embodiments, one or more indicating units 120 may display one or more dosages 122 of one or more nutraceutical agents 118 and the formulation type of the one or more nutraceutical agents 118 according to a color scheme that is in human-readable format. In some embodiments, one or more indicating units 120 may display one or more dosages 122 of one or more nutraceutical agents 118, one or more routes of administration for the one or more nutraceutical agents 118, one or more times and/or periodicities for administration of the one or more nutraceutical agents 118, one or more formulation types for the one or more nutraceutical agents 118, whether to administer the one or more nutraceutical agents 118 with or without food, whether to administer the one or more nutraceutical agents 118 with or without other nutraceutical agents 118 and/or pharmaceutical agents, and substantially any combination thereof. Dosages 122 may be displayed according to numerous methods that are known and have been described (i.e., U.S. patent application Ser. No. 11/474,109, entitled CUSTOMIZED VISUAL MARKING FOR MEDICATION LABELING, filed 23 Jun. 2006, herein incorporated by reference to the extent such subject matter is not inconsistent herewith). In some embodiments, one or more indicating units 120 may indicate one or more dosages 122 in human-readable format and machine-readable format.

At operation 2304, the indicating operation 1830 may include indicating the one or more dosages of the one or more nutraceutical agents in machine-readable format. In some embodiments, one or more indicating units 120 indicate the one or more dosages 122 of the one or more nutraceutical agents 118 in machine-readable format.

In some embodiments, one or more indicating units 120 may indicate one or more dosages 122 of one or more nutraceutical agents 118 in machine-readable format. Numerous methods may be used to indicate one or more dosages 122. Examples of such methods include, but are not limited to, radio frequency identification, bar coding, typographical methods, symbol based methods (i.e., use of symbols that represent dosages 122 and nutraceutical agents 118), optical methods (i.e., pulsed light), and the like.

In some embodiments, one or more indicating units 120 may indicate one or more dosages 122 of one or more nutraceutical agents 118 and the formulation type of the one or more nutraceutical agents 118 in machine-readable form. In some embodiments, one or more indicating units 120 may indicate one or more dosages 122 of one or more nutraceutical agents 118 in a pictographic form that is in machine-readable format. In some embodiments, one or more indicating units 120 may indicate one or more dosages 122 of one or more nutraceutical agents 118 and the formulation type of the one or more nutraceutical agents 118 in a pictographic form that is in machine-readable format. In some embodiments, one or more indicating units 120 may indicate one or more dosages 122 of one or more nutraceutical agents 118 according to a color scheme that is in machine-readable format. In some embodiments, one or more indicating units 120 may indicate one or more dosages 122 of one or more nutraceutical agents 118 and the formulation type of the one or more nutraceutical agents 118 according to a color scheme that is in machine-readable format. In some embodiments, one or more indicating units 120 may indicate one or more dosages 122 of one or more nutraceutical agents 118, one or more routes of administration for the one or more nutraceutical agents 118, one or more times and/or periodicities for administration of the one or more nutraceutical agents 118, one or more formulation types for the one or more nutraceutical agents 118, whether to administer the one or more nutraceutical agents 118 with or without food, whether to administer the one or more nutraceutical agents 118 with or without other nutraceutical agents 118 and/or pharmaceutical agents, and substantially any combination thereof. Numerous labeling methods are known and have been described that may be adapted into a machine-readable format (i.e., U.S. patent application Ser. No. 11/474, 109, entitled CUSTOMIZED VISUAL MARKING FOR MEDICATION LABELING, filed 23 Jun. 2006, herein incorporated by reference to the extent such subject matter is not inconsistent herewith). In some embodiments, one or more indicating units 120 may indicate one or more dosages 122 in human-readable and in a machine-readable format.

At operation 2306, the indicating operation 1830 may include depositing the one or more dosages of the one or more nutraceutical agents on one or more labels. In some embodiments, one or more indicating units 120 deposit the one or more dosages 122 of the one or more nutraceutical agents 118 on one or more labels.

In some embodiments, one or more indicating units 120 may print one or more labels that include one or more dosages 122 of one or more nutraceutical agents 118 and the formulation type of the one or more nutraceutical agents 118. In some embodiments, one or more indicating units 120 may print one or more labels that include one or more dosages 122 of one or more nutraceutical agents 118 in pictographic form. In some embodiments, one or more indicating units 120 may print one or more labels that include one or more dosages 122 of one or more nutraceutical agents 118 and the formulation type of the one or more nutraceutical agents 118 in pictographic form. In some embodiments, one or more indicating units 120 may print one or more labels that include one or more dosages 122 of one or more nutraceutical agents 118 according to a color scheme. In some embodiments, one or more indicating units 120 may print one or more labels that include one or more dosages 122 of one or more nutraceutical agents 118 and the formulation type of the one or more nutraceutical agents 118 according to a color scheme. In some embodiments, one or more indicating units 120 may indicate one or more dosages 122 of one or more nutraceutical agents 118, one or more routes of administration for the one or more nutraceutical agents 118, one or more times and/or periodicities for administration of the one or more nutraceutical agents 118, one or more formulation types for the one or more nutraceutical agents 118, whether to administer the one or more nutraceutical agents 118 with or without food, whether to administer the one or more nutraceutical agents 118 with or without other nutraceutical agents 118 and/or pharmaceutical agents, and substantially any combination thereof. Numerous labeling methods are known and have been described which may be adapted into machine-readable form (i.e., U.S. patent application Ser. No. 11/474,109, entitled CUSTOMIZED VISUAL MARKING FOR MEDICATION LABELING, filed 23 Jun. 2006, herein incorporated by reference to the extent such subject matter is not inconsistent herewith).

In some embodiments, one or more indicating units 120 may indicate one or more dosages 122 in human-readable and machine-readable form. Numerous types of depositing methods may be used by one or more indicating units 120. Examples of such methods include, but are not limited to, printing methods (i.e., stamping, ink-jet printing, laser printing, and the like). In some embodiments, ink containing magnetic particles may be used.

At operation 2308, the indicating operation 1830 may include dispensing the one or more nutraceutical agents. In some embodiments, one or more indicating units 120 dispense the one or more nutraceutical agents 118.

One or more indicating units 120 may dispense one or more nutraceutical agents 118 in numerous dosage forms. In some embodiments, one or more indicating units 120 may dispense one or more nutraceutical agents 118 in powder form. In some embodiments, one or more indicating units 120 may dispense one or more nutraceutical agents 118 in liquid form. In some embodiments, one or more indicating units 120 may dispense one or more nutraceutical agents 118 in tablet form. In some embodiments, one or more indicating units 120 may dispense one or more nutraceutical agents 118 in capsule form.

At operation 2310, the indicating operation 1830 may include dispensing the one or more nutraceutical agents in unit dosage form. In some embodiments, one or more indicating units 120 dispense the one or more nutraceutical agents 118 in unit dosage form.

In some embodiments, one or more indicating units 120 may dispense one or more nutraceutical agents 118 in a unit dosage form in which the entire dosage 122 is to be administered to an individual 108 as a single dosage 122. In some embodiments, one or more indicating units 120 may dispense one or more nutraceutical agents 118 in a unit dosage form that may be administered such that the individual 108 will maintain a level of the one or more nutraceuticals for a given time period. For example, in some embodiments, a unit dosage form may be an amount of one or more nutraceutical agents 118 that will allow the one or more nutraceutical agents 118 to be maintained within an individual 108 for four hours. Numerous criteria may be used to determine a unit dosage form. Examples of such criteria include, but are not limited to, physical characteristics of the individual 108, physiological characteristics of the individual 108, activity of the individual 108, and the like.

At operation 2312, the indicating operation 1830 may include dispensing two or more of the one or more nutraceutical agents in a single administration form. In some embodiments, one or more indicating units 120 dispense two or more of the one or more nutraceutical agents 118 in a single administration form.

In some embodiments, one or more indicating units 120 may dispense two or more nutraceutical agents 118 in a single administration form to provide for administration of the two or more nutraceutical agents 118 to an individual 108. Such methods have been described (i.e., U.S. patent application Ser. No. 11/453,571, filed 14 Jun. 2006; U.S. patent application Ser. No. 11/478,341, filed 28 Jun. 2006; U.S. patent application Ser. No. 11/478,296, filed 28 Jun. 2006; and U.S. patent application Ser. No. 11/486,998, filed 14 Jul. 2006, herein incorporated by reference to the extent such subject matter is not inconsistent herewith).

Figure 24:
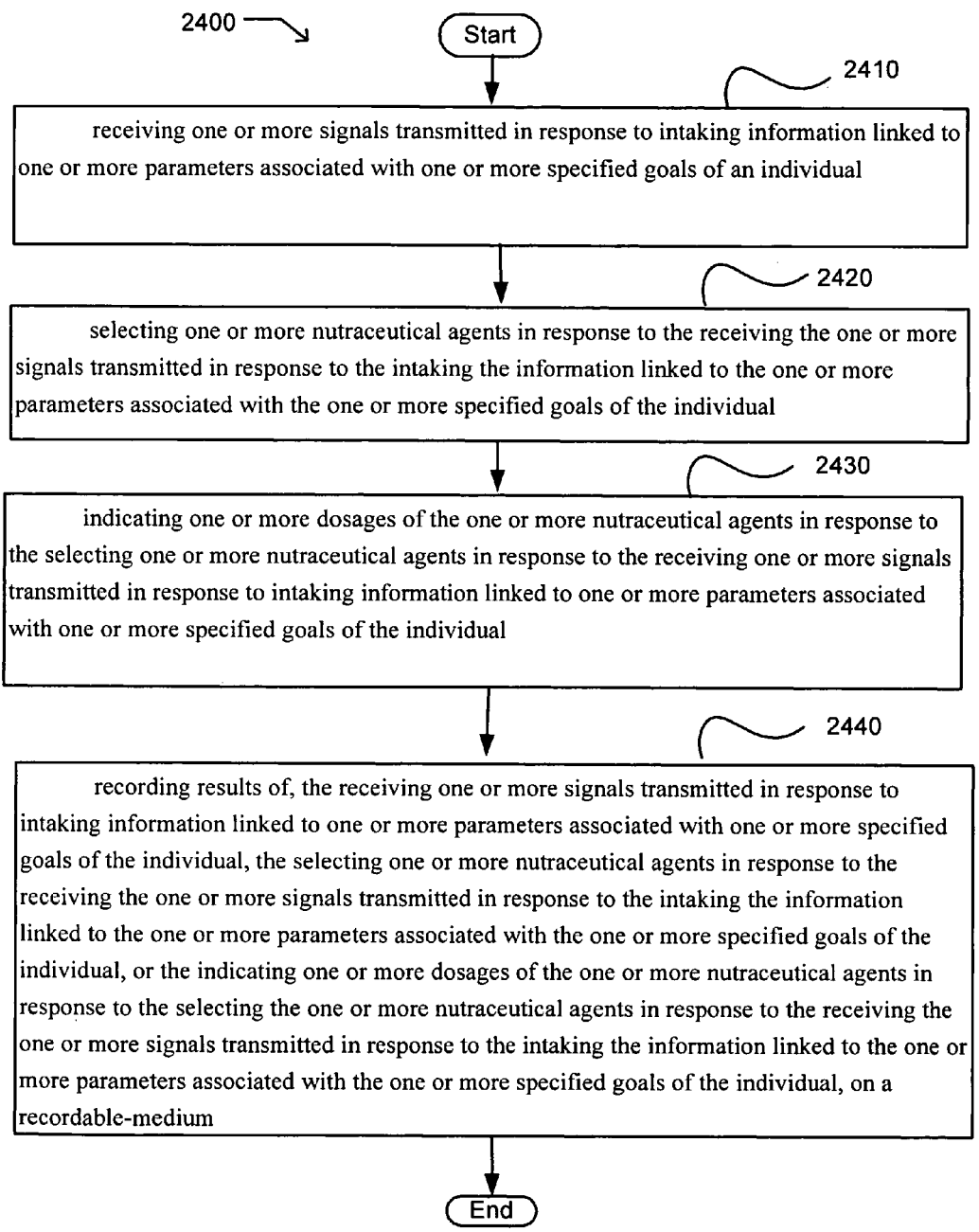
FIG. 24 illustrates an operational flow 2400 representing example operations related to methods for nutraceutical agent selection and dosing.

FIG. 24 illustrates an operational flow 2400 that includes a receiving operation 2410, a selecting operation 2420, and an indicating operation 2430 (which correspond to the receiving operation 1810, the selecting operation 1820, and the indicating operation 1830 illustrated in FIG. 18) with an additional recording operation 2440. In FIG. 24, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 2400 includes the operations 2410, 2420, and 2430 (which correspond to operations 1810, 1820, and 1830 as described with regard to FIG. 18) and an additional recording operation 2440 involving recording results of, the receiving one or more signals transmitted in response to intaking information linked to one or more parameters associated with one or more specified goals of an individual, the selecting one or more nutraceutical agents in response to the receiving the one or more signals transmitted in response to the intaking the information linked to the one or more parameters associated with the one or more specified goals of the individual, or the indicating one or more dosages of the one or more nutraceutical agents in response to the selecting the one or more nutraceutical agents in response to the receiving the one or more signals transmitted in response to the intaking the information linked to the one or more parameters associated with the one or more specified goals of the individual, on a recordable-medium.

In some embodiments, one or more recording units 124 may record results of, the receiving one or more signals 130 transmitted in response to intaking information 112 linked to one or more parameters 114 associated with one or more specified goals 106 of the individual 108, the selecting one or more nutraceutical agents 118 in response to the receiving one or more signals 130 transmitted in response to intaking information 112 linked to one or more parameters 114 associated with one or more specified goals 106 of the individual 108, or the indicating one or more dosages 122 of the one or more nutraceutical agents 118 in response to the selecting one or more nutraceutical agents 118 in response to the receiving one or more signals 130 transmitted in response to intaking information 112 linked to one or more parameters 114 associated with one or more specified goals 106 of the individual 108, on a recordable-medium 126.

Figure 25:
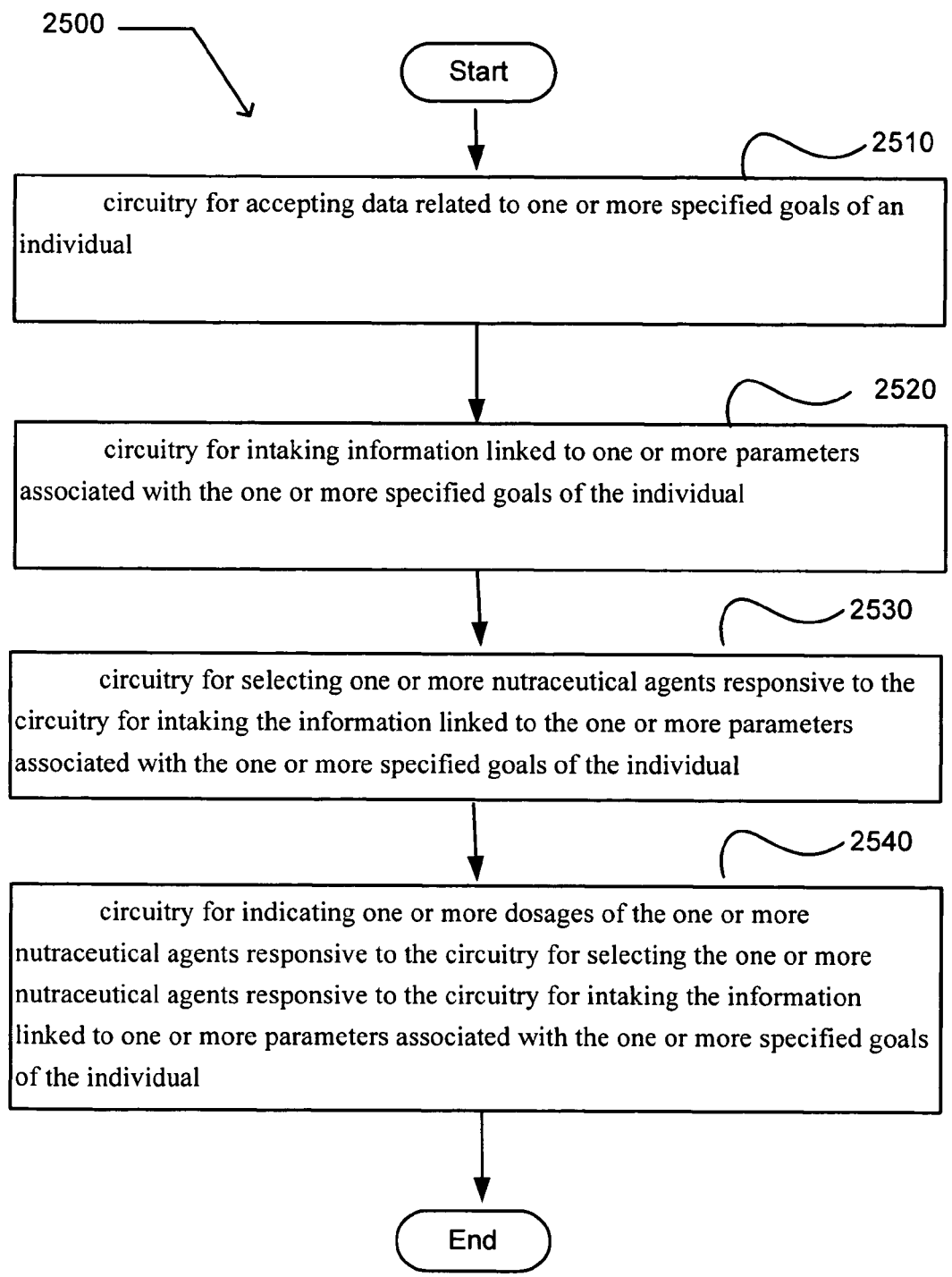
FIG. 25 illustrates an example system 2500 in which embodiments may be implemented.

FIG. 25 illustrates a system 2500 representing examples of circuitry that is related to systems for nutraceutical agent 118 and dosing. In FIG. 25 discussion and explanation may be provided with respect to the above-described example of FIG. 1, and/or with respect to other examples and contexts. However, it should be understood that the circuitry may be assembled in a number of other environments and contexts, and/or modified versions of FIG. 1. Also, although various circuitry is presented in the sequence(s) illustrated, it should be understood that circuitry may be assembled in other configurations than those which are illustrated.

After a start operation, the system 2500 includes a circuitry block 2510 that includes circuitry for accepting data related to one or more specified goals of an individual. In some embodiments, the circuitry may be used for accepting data 104 related to one or more specified goals 106 of an individual 108.

The one or more specified goals 106 may be virtually any goal to be achieved, or attempted by, an individual 108 that may be affected by administration of one or more nutraceutical agents 118 to the individual 108. In some embodiments, administration of one or more nutraceutical agents 118 to an individual 108 may assist the individual 108 to achieve one or more specified goals 106. In some embodiments, administration of one or more nutraceutical agents 118 to an individual 108 may stimulate the individual 108 to achieve one or more specified goals 106. In some embodiments, administration of one or more nutraceutical agents 118 to an individual 108 may reduce an inhibition coupled to the individual 108 to promote achieving one or more specified goals 106 by the individual 108. Numerous examples of specified goals 106 of an individual 108 exist. In some embodiments, specified goals 106 of an individual 108 may be related to attentiveness, alertness, test performance, relaxation, pain, fever, attractiveness, anxiety, fall, injury, accident, bite, bleeding, inflammation, infection, drowsiness, insomnia, discomfort, stress, grooming, appearance, capability, performance, improvement, enhancement, curtailment, wellbeing, vitality, vigor, disability, phobia, malady, psychosis, environmental extremes, environmental exposure, dysfunction, disease symptom, chronic condition, mental acuity, emotional behavior, physical prowess, addiction, obsession, therapy, remedy, behavior, nutrition, diet, exercise, immunization, prevention, diagnosis, subscription, regimen, social performance, social interaction, endurance, sexual attribute, sexual performance, age-related attribute, age-related condition, prophylaxis, treatment, and substantially any combination thereof. In some embodiments, data 104 may include identification of one or more of the specified goals 106 of an individual 108. In some embodiments, data 104 may include characteristics of an individual 108. Examples of such data 104 may include, but are not limited to, physical characteristics, metabolic characteristics, financial characteristics, and the like. In some embodiments, data 104 may include, an individual's 108 height, weight, gender, kidney function, liver function, level of physical fitness, age, allergic response, metabolic level (i.e., resting metabolic rate and/or activity-related metabolic rate), disease state, body fat percentage, body mass index, personal health habits (i.e., smoking, alcohol consumption, diet, illegal drug use, and the like), family health history, insurance coverage, food supplement usage, nutraceutical agent 118 usage, non-prescription drug use, prescription drug use, pregnancy status, and the like. In some embodiments, the one or more characteristics may be specifically associated with an individual 108. As such, in some embodiments, the one or more characteristics may be unique to the individual 108 as opposed to being common to a group. For example, in some embodiments, an individual 108 may be a member of a group of persons who are diabetic while exhibiting one or more characteristics, such as metabolic characteristics, that are unique to the individual 108. Accordingly, in some embodiments, data 104 may be input that provides for selection of nutraceutical agents 118 in accordance with one or more characteristics and specified goals 106 of an individual 108.

After a start operation, the system 2500 includes a circuitry block 2520 that includes circuitry for intaking information linked to one or more parameters associated with the one or more specified goals of the individual. In some embodiments, the circuitry may be used for intaking information 112 linked to one or more parameters 114 associated with the one or more specified goals 106 of the individual 108.

Numerous parameters 114 may be associated with one or more specified goals 106 of an individual 108. Examples of such parameters 114 include, but are not limited to, blood sugar levels, blood insulin levels, blood iron levels, hormone levels (amine-derived hormones: such as catecholamines (adrenaline, dopamine, noradrenaline); tryptophan derivatives (melatonin, serotonin); tyrosine derivatives (thyroxine and triiodothyronine); peptide hormones such as antimullerian hormone, adiponectin, adrenocorticotropic hormone, angiotensinogen and angiotensin, antidiuretic hormone, atrial-natriuretic peptide, calcitonin, cholecystokinin, corticotropin-releasing hormone, erythropoietin, follicle-stimulating hormone, gastrin, ghrelin, glucagons, gonadotropin-releasing hormone, growth hormone-releasing hormone, human chorionic gonadotropin, growth hormone, inhibin, insulin, insulin-like growth factor, luteinizing hormone, melanocyte stimulating hormone, neuropeptide Y, oxytocin, parathyroid hormone, prolactin, relaxin, secretin, somatostatin, thrombopoietin, thyroid-stimulating hormone, thyrotropin-releasing hormone; steroid hormones: Glucocorticoids (cortisol); Mineralocorticoids (aldosterone); sex steroids: androgens (testosterone, dehydroepiandrosterone, dehydroepiandrosterone sulfate, androstenedione, dihydrotestosterone); estrogens (estradiol); progestagens (progesterone and progestins); sterol hormones: vitamin D derivatives (calcitriol); lipid hormones (prostaglandins, leukotrienes, prostacyclin, and thromboxane)), nutraceutical agent 118 levels, pharmaceutical agent levels, cytokine levels, and the like (i.e., Fitzgerald et al., The Cytokine Facts Book, Academic Press, San Francisco, Second Edition, (2001)). Methods to gain information 112 with regard to components of biological systems are known (i.e., Clinical Laboratory Medicine, Lippincott Williams and Wilkins, Philadelphia, Second Edition, 2002). In some embodiments, one or more intaking units 110 may include instrumentation that provides for analysis of a sample obtained from an individual 108. For example, in some embodiments, an intaking unit 110 may be configured to intake a blood sample obtained from an individual 108 and analyze the blood sample to determine one or more parameters 114 associated with one or more specified goals 106 of an individual 108 (i.e., determine the level of free testosterone or the level of melatonin in a blood sample obtained from an individual 108). Numerous analytical technologies are known and may be included within one or more intaking units 110. Examples of such technologies include, but are not limited to, gas chromatography, mass spectrometry, atomic absorption, immunoassay based methods, microfluidic based methods, spectrophotometry (i.e., infrared, ultraviolet, fluorescence, and the like), surface plasmon resonance, fluorescence resonance energy transfer, and the like. In some embodiments, one or more intaking units 110 may intake information 112 linked to one or more parameters 114 associated with the one or more specified goals 106 of an individual 108 from a source that is independent of the one or more intaking units 110. In some embodiments, one or more intaking units 110 may intake information 112 linked to one or more parameters 114 associated with the one or more specified goals 106 of an individual 108 from a source that is coupled to the one or more intaking units 110.

After a start operation, the system 2500 includes a circuitry block 2530 that includes circuitry for selecting one or more nutraceutical agents responsive to the circuitry for intaking the information linked to the one or more parameters associated with the one or more specified goals of the individual. In some embodiments, the circuitry may be used for selecting one or more nutraceutical agents 118 responsive to the circuitry for intaking information 112 linked to one or more parameters 114 associated with the one or more specified goals 106 of the individual 108.

In some embodiments, one or more selecting units 116 may select one or more nutraceutical agents 118 in response to one or more intaking units 110. In some embodiments, one or more selecting units 116 may select one or more nutraceutical agents 118 in response to one or more accepting units 102. In some embodiments, one or more selecting units 116 may select one or more nutraceutical agents 118 in response to one or more intaking units 110 and one or more accepting units 102. Accordingly, in some embodiments, one or more selecting units 116 may select one or more nutraceutical agents 118 with regard to one or more characteristics of the individual 108 and one or more parameters 114 associated with one or more specified goals 106 of the individual 108. For example, in some embodiments, one or more selecting units 116 may select one or more nutraceutical agents 118 based on the age of the individual 108 and the level of testosterone in the individual's 108 blood. In other embodiments, one or more selecting units 116 may select one or more nutraceutical agents 118 based on insurance coverage held by an individual 108 and a specified goal 106 of the individual 108. Accordingly, numerous combinations of information 112 and data 104 may be used by one or more selecting units 116 to select one or more nutraceutical agents 118.

After a start operation, the system 2500 includes a circuitry block 2540 that includes circuitry for indicating one or more dosages of the one or more nutraceutical agents responsive to the circuitry for selecting the one or more nutraceutical agents responsive to the circuitry for intaking the information linked to the one or more parameters associated with the one or more specified goals of the individual. In some embodiments, the circuitry may be used for indicating one or more dosages 122 of the one or more nutraceutical agents 118 responsive to the circuitry for selecting one or more nutraceutical agents 118 responsive to the circuitry for intaking information 112 linked to one or more parameters 114 associated with the one or more specified goals 106 of the individual 108.

In some embodiments, the circuitry may be used for indicating one or more dosages 122 of one or more nutraceutical agents 118 in human-readable format. In some embodiments, the circuitry may be used for indicating one or more dosages 122 of one or more nutraceutical agents 118 in machine-readable format. In some embodiments, the circuitry may be used for depositing one or more dosages 122 of one or more nutraceutical agents 118 on one or more labels. In some embodiments, the circuitry may be used for dispensing one or more nutraceutical agents 118. In some embodiments, the circuitry may be used for dispensing one or more nutraceutical agents 118 in unit dosage form. In some embodiments, the circuitry may be used for dispensing two or more of one or more nutraceutical agents 118 in a single administration form.

Figure 26:
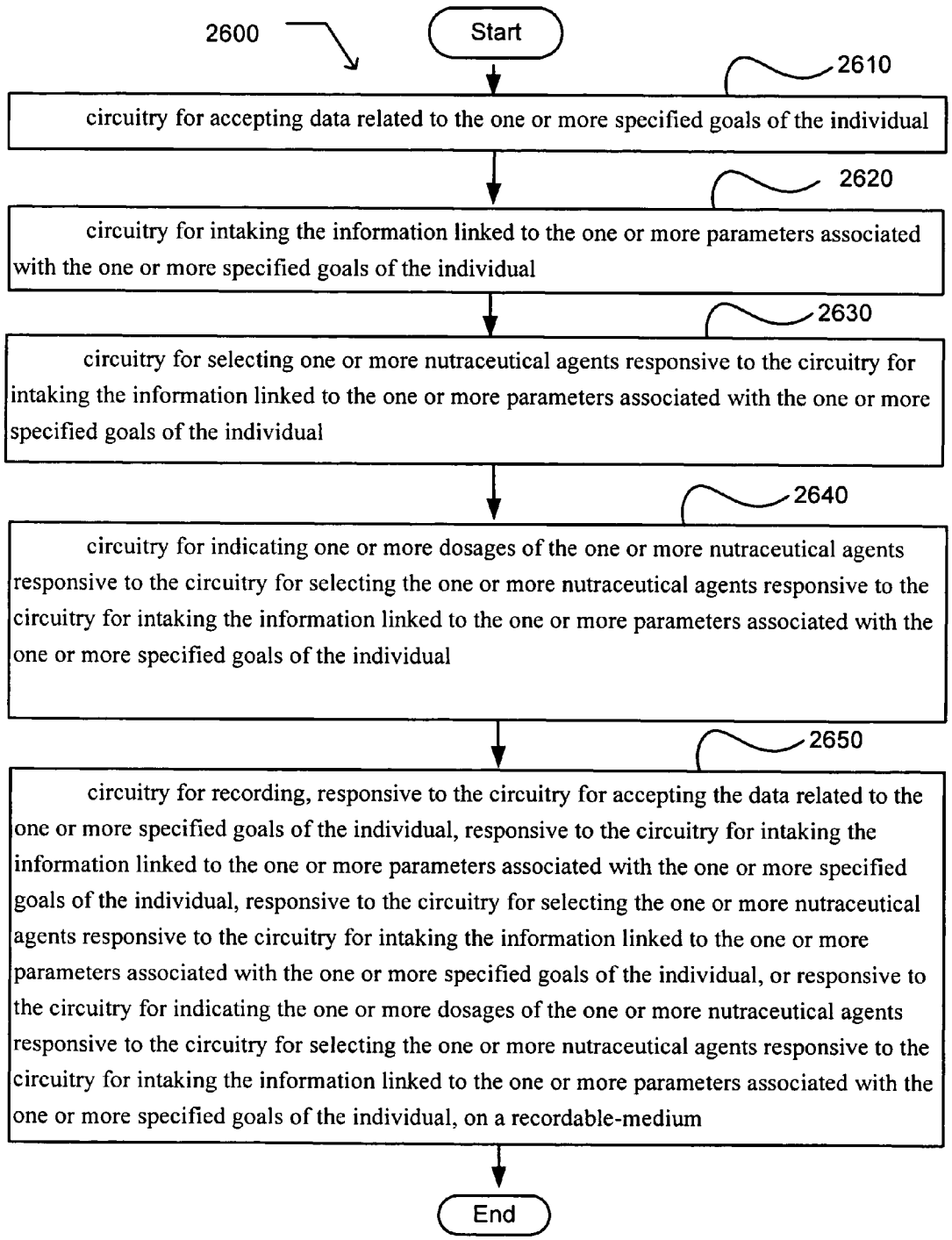
FIG. 26 illustrates an example system 2600 in which embodiments may be implemented.

FIG. 26 illustrates a system 2600 representing examples of circuitry that is related to systems for nutraceutical agent 118 and dosing. In FIG. 26 discussion and explanation may be provided with respect to the above-described example of FIG. 1, and/or with respect to other examples and contexts. However, it should be understood that the circuitry may be assembled in a number of other environments and contexts, and/or modified versions of FIG. 1. Also, although various circuitry is presented in the sequence(s) illustrated, it should be understood that circuitry may be assembled in other configurations than those which are illustrated.

After a start operation, the operational flow 2600 includes circuitry blocks 2610, 2620, 2630, and 2640 (which correspond to circuitry blocks 2510, 2520, 2530, and 2540 as described with regard to FIG. 25) and an additional circuitry block 2650 involving circuitry for recording, responsive to the circuitry for accepting the data related to the one or more specified goals of the individual, responsive to the circuitry for intaking the information linked to the one or more parameters associated with the one or more specified goals of the individual, responsive to the circuitry for selecting the one or more nutraceutical agents responsive to the circuitry for intaking the information linked to the one or more parameters associated with the one or more specified goals of the individual, or responsive to the circuitry for indicating the one or more dosages of the one or more nutraceutical agents responsive to the circuitry for selecting the one or more nutraceutical agents responsive to the circuitry for intaking the information linked to the one or more parameters associated with the one or more specified goals of the individual, on a recordable-medium. In some embodiments, the circuitry may be used for recording, responsive to the circuitry for accepting data 104 related to one or more specified goals 106 of an individual 108, responsive to the circuitry for intaking information 112 linked to one or more parameters 114 associated with the one or more specified goals 106 of the individual 108, responsive to the circuitry for selecting one or more nutraceutical agents 118 responsive to the circuitry for intaking information 112 linked to one or more parameters 114 associated with the one or more specified goals 106 of the individual 108, or responsive to the circuitry for indicating one or more dosages 122 of the one or more nutraceutical agents 118 responsive to the circuitry for selecting one or more nutraceutical agents 118 responsive to the circuitry for intaking information 112 linked to one or more parameters 114 associated with the one or more specified goals 106 of the individual 108, on a recordable-medium 126.

Figure 27:
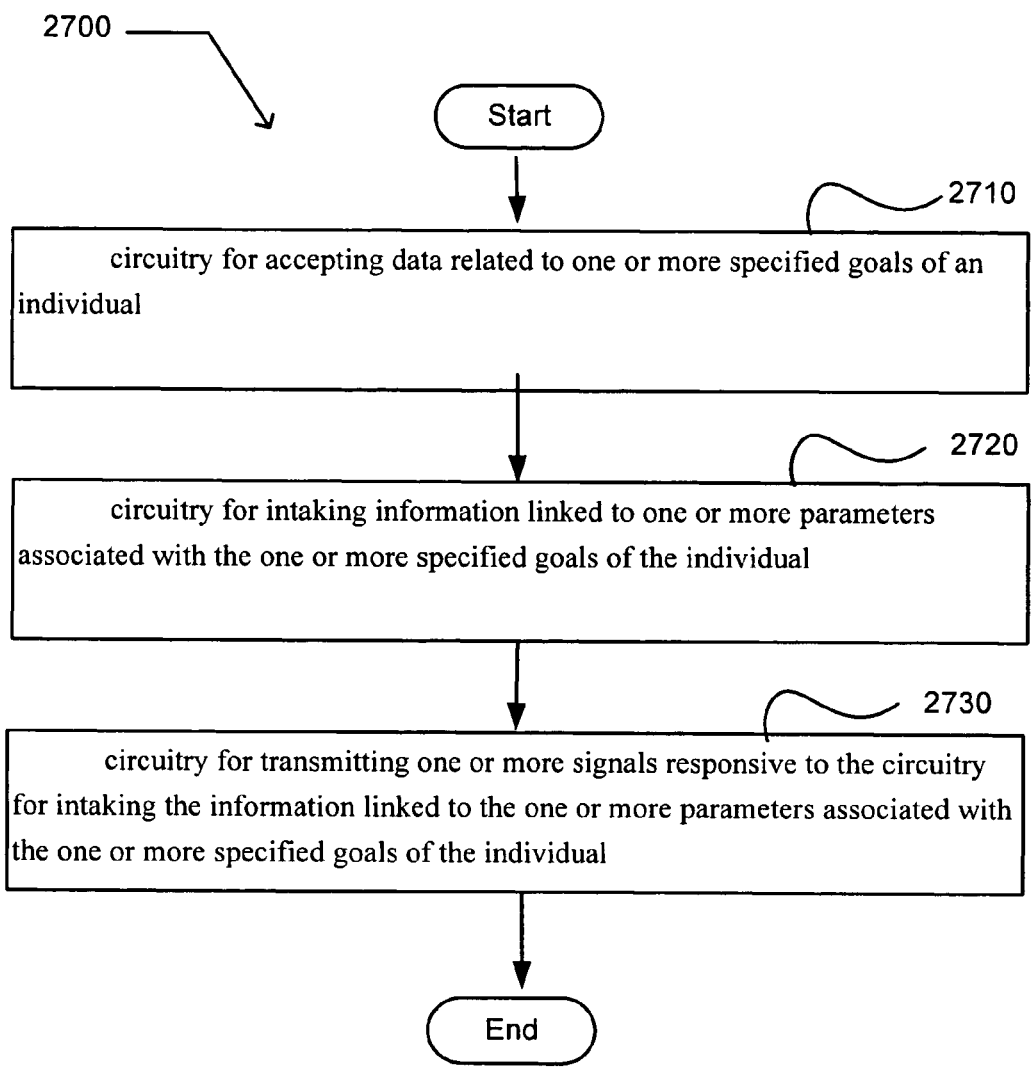
FIG. 27 illustrates an example system 2700 in which embodiments may be implemented.

FIG. 27 illustrates a system 2700 representing examples of circuitry that is related to systems for nutraceutical agent 118 and dosing. In FIG. 27 discussion and explanation may be provided with respect to the above-described example of FIG. 1, and/or with respect to other examples and contexts. However, it should be understood that the circuitry may be assembled in a number of other environments and contexts, and/or modified versions of FIG. 1. Also, although various circuitry is presented in the sequence(s) illustrated, it should be understood that circuitry may be assembled in other configurations than those which are illustrated.

After a start operation, the system 2700 includes a circuitry block 2710 that includes circuitry for accepting data related to one or more specified goals of an individual. In some embodiments, the circuitry may be used for accepting data 104 related to one or more specified goals 106 of an individual 108.

The one or more specified goals 106 may be virtually any goal to be achieved, or attempted by, an individual 108 that may be affected by administration of one or more nutraceutical agents 118 to the individual 108. In some embodiments, administration of one or more nutraceutical agents 118 to an individual 108 may assist the individual 108 to achieve one or more specified goals 106. In some embodiments, administration of one or more nutraceutical agents 118 to an individual 108 may stimulate the individual 108 to achieve one or more specified goals 106. In some embodiments, administration of one or more nutraceutical agents 118 to an individual 108 may reduce an inhibition coupled to the individual 108 to promote achieving one or more specified goals 106 by the individual 108. Numerous examples of specified goals 106 of an individual 108 exist. In some embodiments, specified goals 106 of an individual 108 may be related to attentiveness, alertness, test performance, relaxation, pain, fever, attractiveness, anxiety, fall, injury, accident, bite, bleeding, inflammation, infection, drowsiness, insomnia, discomfort, stress, grooming, appearance, capability, performance, improvement, enhancement, curtailment, wellbeing, vitality, vigor, disability, phobia, malady, psychosis, environmental extremes, environmental exposure, dysfunction, disease symptom, chronic condition, mental acuity, emotional behavior, physical prowess, addiction, obsession, therapy, remedy, behavior, nutrition, diet, exercise, immunization, prevention, diagnosis, subscription, regimen, social performance, social interaction, endurance, sexual attribute, sexual performance, age-related attribute, age-related condition, prophylaxis, treatment, and substantially any combination thereof. In some embodiments, data 104 may include identification of one or more of the specified goals 106 of an individual 108. In some embodiments, data 104 may include characteristics of an individual 108. Examples of such data 104 may include, but are not limited to, physical characteristics, metabolic characteristics, financial characteristics, and the like. In some embodiments, data 104 may include, an individual's 108 height, weight, gender, kidney function, liver function, level of physical fitness, age, allergic response, metabolic level (i.e., resting metabolic rate and/or activity-related metabolic rate), disease state, body fat percentage, body mass index, personal health habits (i.e., smoking, alcohol consumption, diet, illegal drug use, and the like), family health history, insurance coverage, food supplement usage, nutraceutical agent 118 usage, non-prescription drug use, prescription drug use, pregnancy status, and the like. In some embodiments, the one or more characteristics may be specifically associated with an individual 108. As such, in some embodiments, the one or more characteristics may be unique to the individual 108 as opposed to being common to a group. For example, in some embodiments, an individual 108 may be a member of a group of persons who are diabetic while exhibiting one or more characteristics, such as metabolic characteristics, that are unique to the individual 108. Accordingly, in some embodiments, data 104 may be input that provides for selection of nutraceutical agents 118 in accordance with one or more characteristics and specified goals 106 of an individual 108.

After a start operation, the system 2700 includes a circuitry block 2720 that includes circuitry for intaking information linked to one or more parameters associated with the one or more specified goals of the individual. In some embodiments, the circuitry may be used for intaking information 112 linked to one or more parameters 114 associated with the one or more specified goals 106 of the individual 108.

Numerous parameters 114 may be associated with one or more specified goals 106 of an individual 108. Examples of such parameters 114 include, but are not limited to, blood sugar levels, blood insulin levels, blood iron levels, hormone levels, nutraceutical agent 118 levels, pharmaceutical agent levels, cytokine levels, and the like (i.e., Fitzgerald et al., The Cytokine Facts Book, Academic Press, San Francisco, Second Edition, (2001)). Methods to gain information 112 with regard to components of biological systems are known (i.e., Clinical Laboratory Medicine, Lippincott Williams and Wilkins, Philadelphia, Second Edition, 2002). In some embodiments, one or more intaking units 110 may include circuitry for analysis of a sample obtained from an individual 108. For example, in some embodiments, an intaking unit 110 may include circuitry that is configured for analysis of a blood sample obtained from an individual 108 to determine one or more parameters 114 associated with one or more specified goals 106 of an individual 108 (i.e., determine the level of free testosterone or the level of melatonin in a blood sample obtained from an individual 108). Numerous analytical technologies are known and may be included within one or more intaking units 110. Examples of such technologies include, but are not limited to, gas chromatography, mass spectrometry, atomic absorption, immunoassay based methods, microfluidic based methods, spectrophotometry (i.e., infrared, ultraviolet, fluorescence, and the like), surface plasmon resonance, fluorescence resonance energy transfer, and the like. In some embodiments, the circuitry may be used to intake information 112 linked to one or more parameters 114 associated with the one or more specified goals 106 of an individual 108 from a source that is independent of the one or more intaking units 110. In some embodiments, the circuitry may intake information 112 linked to one or more parameters 114 associated with the one or more specified goals 106 of an individual 108 from a source that is coupled to the one or more intaking units 110.

After a start operation, the system 2700 includes a circuitry block 2730 that includes circuitry for transmitting one or more signals responsive to the circuitry for intaking the information linked to the one or more parameters associated with the one or more specified goals of the individual. In some embodiments, the circuitry may be used for transmitting one or more signals 130 responsive to the circuitry for intaking information 112 linked to one or more parameters 114 associated with the one or more specified goals 106 of the individual 108.

In some embodiments, the circuitry may be used for transmitting one or more levels of one or more metabolic indicators linked to the individual 108. In some embodiments, the circuitry may be used for transmitting one or more levels of one or more metabolic activities linked to the individual 108. In some embodiments, the circuitry may be used for transmitting one or more levels of one or more nutraceutical agents 118 linked to the individual 108. In some embodiments, the circuitry may be used for transmitting one or more levels of one or more pharmaceutical agents linked to the individual 108. In some embodiments, the circuitry may be used for transmitting one or more parameters 114 associated with the one or more specified goals 106 of the individual 108. In some embodiments, the circuitry may be used for transmitting one or more instructions to select one or more nutraceutical agents 118 in response to the intaking information 112 linked to one or more parameters 114 associated with the one or more specified goals 106 of the individual 108. In some embodiments, the circuitry may be used for transmitting one or more signals 130 to select one or more nutraceutical agents 118 to increase one or more levels of one or more components associated with the one or more specified goals 106 of the individual 108. In some embodiments, the circuitry may be used for transmitting one or more signals 130 to select one or more nutraceutical agents 118 to decrease one or more levels of one or more components associated with the one or more specified goals 106 of the individual 108. In some embodiments, the circuitry may be used for transmitting one or more signals 130 to select one or more nutraceutical agents 118 that stimulate one or more metabolic pathways linked to the individual 108. In some embodiments, the circuitry may be used for transmitting one or more signals 130 to select one or more nutraceutical agents 118 that inhibit one or more metabolic pathways linked to the individual 108. In some embodiments, the circuitry may be used for transmitting one or more signals 130 to select at least one vitamin, mineral, enzyme, amino acid, homeopathic supplement, toxin, homeopathic substance, traditional remedy, herbal supplement, glandular supplement, or substantially any combination thereof.

In some embodiments, the circuitry may be used for transmitting one or more signals 130 that include data 104 related to one or more specified goals 106 of an individual 108. The circuitry used for transmitting one or more signals 130 may use numerous technologies. Examples of such technologies include, but are not limited to, wireless circuitry, telephone circuitry, internet circuitry, digital circuitry, analog circuitry, optical circuitry, and the like.

Figure 28:
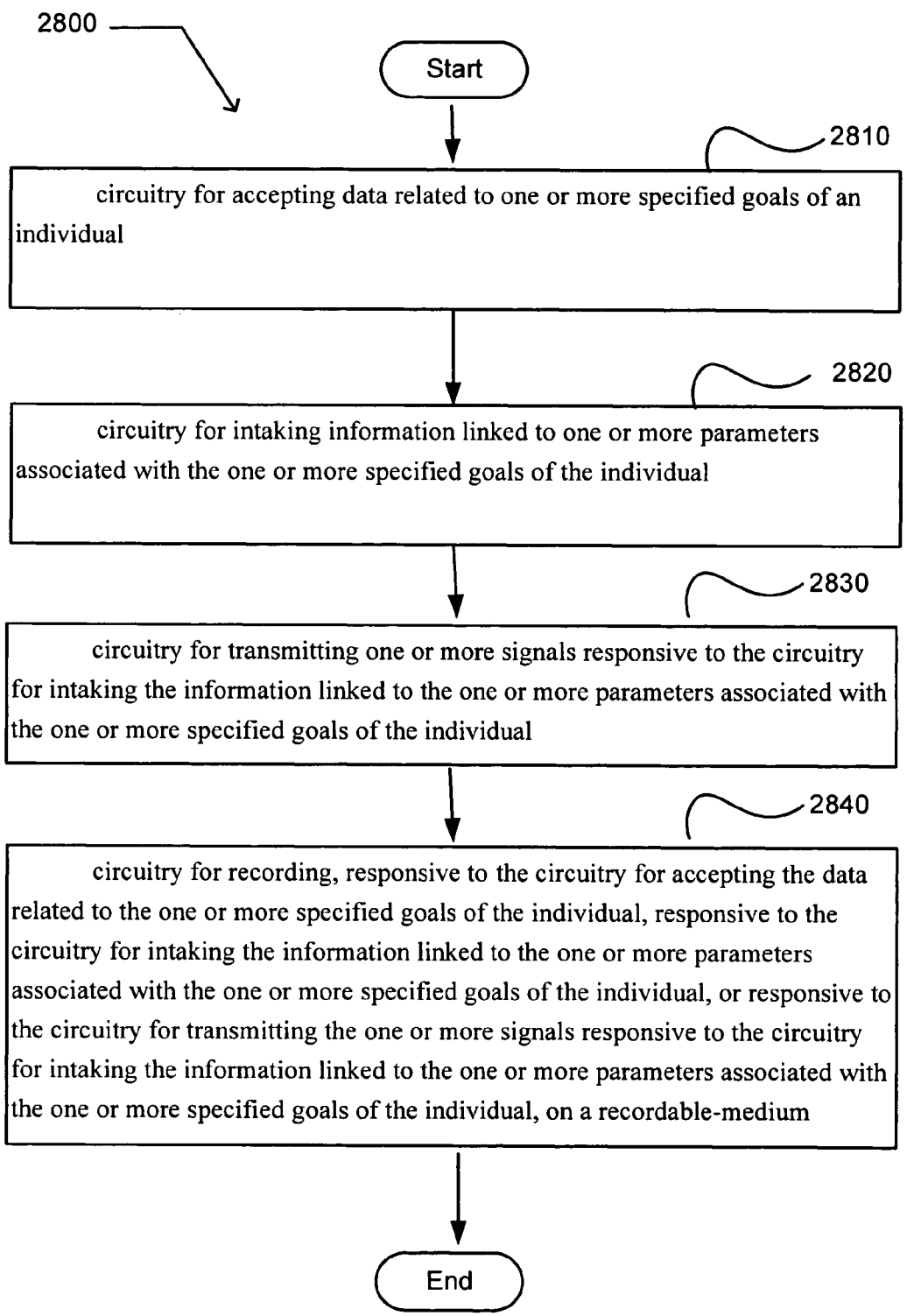
FIG. 28 illustrates an example system 2800 in which embodiments may be implemented.

FIG. 28 illustrates a system 2800 representing examples of circuitry that is related to systems for nutraceutical agent 118 and dosing. In FIG. 28 discussion and explanation may be provided with respect to the above-described example of FIG. 1, and/or with respect to other examples and contexts. However, it should be understood that the circuitry may be assembled in a number of other environments and contexts, and/or modified versions of FIG. 1. Also, although various circuitry is presented in the sequence(s) illustrated, it should be understood that circuitry may be assembled in other configurations than those which are illustrated.

After a start operation, the operational flow 2800 includes circuitry blocks 2810, 2820, and 2830 (which correspond to circuitry blocks 2710, 2720, and 2730 as described with regard to FIG. 27) and an additional circuitry block 2840 involving circuitry for recording, responsive to the circuitry for accepting the data related to the one or more specified goals of the individual, responsive to the circuitry for intaking the information linked to the one or more parameters associated with the one or more specified goals of the individual, or responsive to the circuitry for transmitting the one or more signals responsive to the circuitry for intaking the information linked to the one or more parameters associated with the one or more specified goals of the individual, on a recordable-medium. In some embodiments, the circuitry may be used for recording, responsive to circuitry for accepting data 104 related to one or more specified goals 106 of an individual 108, responsive to circuitry for intaking information 112 linked to one or more parameters 114 associated with the one or more specified goals 106 of the individual 108, or responsive to circuitry for transmitting one or more signals 130 responsive to the circuitry for intaking information 112 linked to one or more parameters 114 associated with the one or more specified goals 106 of the individual 108, on a recordable-medium 126.

Figure 29:
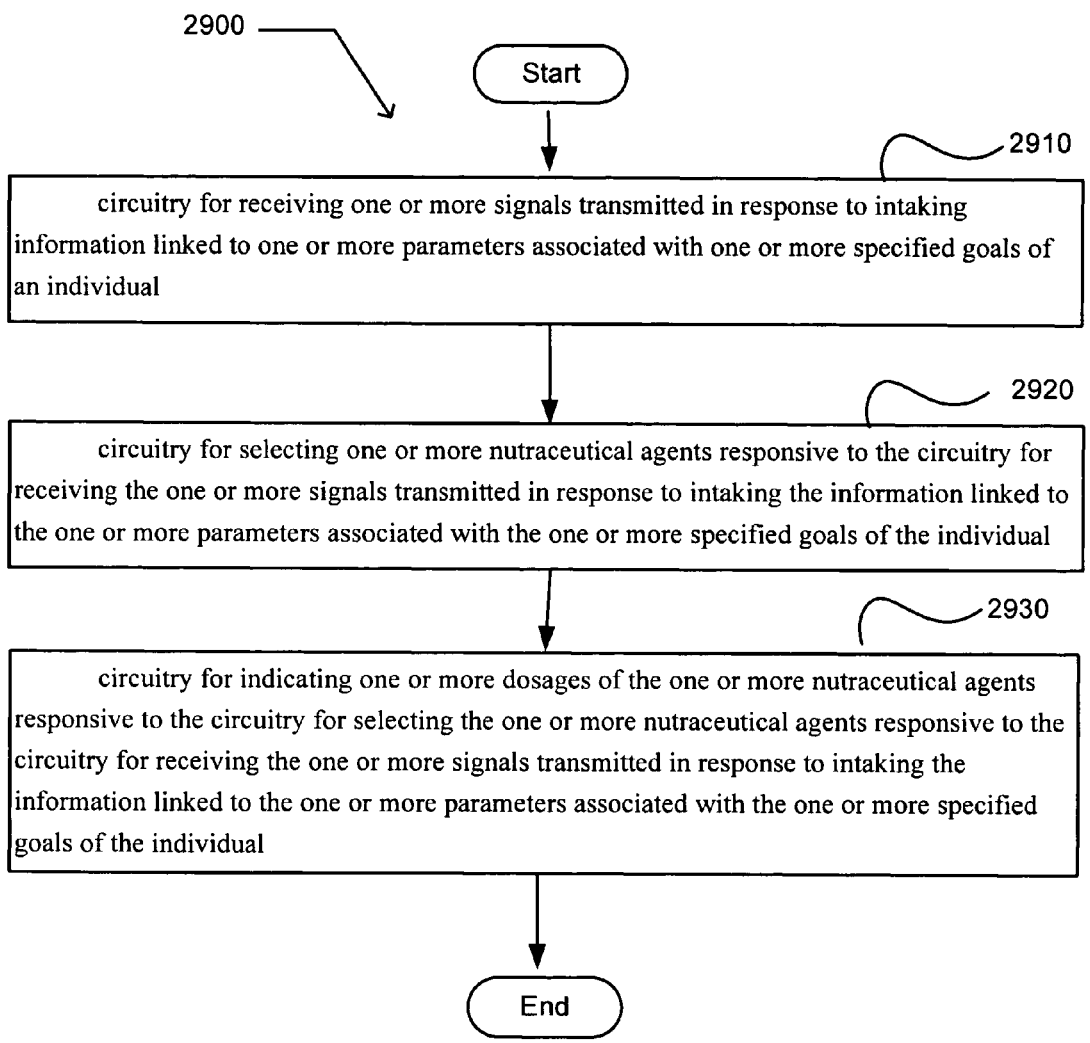
FIG. 29 illustrates an example system 2900 in which embodiments may be implemented.

FIG. 29 illustrates a system 2900 representing examples of circuitry that is related to systems for nutraceutical agent 118 and dosing. In FIG. 29 discussion and explanation may be provided with respect to the above-described example of FIG. 1, and/or with respect to other examples and contexts. However, it should be understood that the circuitry may be assembled in a number of other environments and contexts, and/or modified versions of FIG. 1. Also, although various circuitry is presented in the sequence(s) illustrated, it should be understood that circuitry may be assembled in other configurations than those which are illustrated.

After a start operation, the system 2900 includes a circuitry block 2910 that includes circuitry for receiving one or more signals transmitted in response to intaking information linked to one or more parameters associated with one or more specified goals of an individual. In some embodiments, the circuitry may be used for receiving one or more signals 130 transmitted in response to intaking information 112 linked to one or more parameters 114 associated with one or more specified goals 106 of the individual 108.

In some embodiments, the circuitry may be used for receiving one or more signals 130 that include data 104 related to one or more specified goals 106 of an individual 108. In some embodiments, the circuitry may be used for receiving one or more signals 130 indicating one or more levels of one or more metabolic indicators linked to the individual 108. In some embodiments, the circuitry may be used for receiving one or more signals 130 indicating one or more metabolic activities linked to the individual 108. In some embodiments, the circuitry may be used for receiving one or more signals 130 indicating one or more levels of one or more nutraceutical agents 118 linked to the individual 108. In some embodiments, the circuitry may be used for receiving one or more signals 130 indicating one or more levels of one or more pharmaceutical agents linked to the individual 108. In some embodiments, the circuitry may be used for receiving one or more parameters 114 associated with the one or more specified goals 106 of the individual 108. In some embodiments, the circuitry may be used for receiving one or more instructions to select one or more nutraceutical agents 118 in response to the intaking information 112 linked to one or more parameters 114 associated with the one or more specified goals 106 of the individual 108. In some embodiments, the circuitry may be used for receiving one or more signals 130 to select one or more nutraceutical agents 118 to increase one or more levels of one or more components associated with the one or more specified goals 106 of the individual 108. In some embodiments, the circuitry may be used for receiving one or more signals 130 to select one or more nutraceutical agents 118 to decrease one or more levels of one or more components associated with the one or more specified goals 106 of the individual 108. In some embodiments, the circuitry may be used for receiving one or more signals 130 to select one or more nutraceutical agents 118 that stimulate one or more metabolic pathways linked to the individual 108. In some embodiments, the circuitry may be used for receiving one or more signals 130 to select one or more nutraceutical agents 118 that inhibit one or more metabolic pathways linked to the individual 108. In some embodiments, the circuitry may be used for receiving one or more signals 130 to select at least one vitamin, mineral, enzyme, amino acid, homeopathic supplement, toxin, homeopathic substance, traditional remedy, herbal supplement, glandular supplement, or substantially any combination thereof.

In some embodiments, the circuitry may be used for receiving one or more signals 130 that include data 104 related to one or more specified goals 106 of an individual 108. The circuitry used for receiving may receive one or more signals 130 through use of numerous technologies. Examples of such technologies include, but are not limited to, wireless circuitry, telephone circuitry, internet circuitry, digital circuitry, analog circuitry, optical circuitry, and the like.

After a start operation, the system 2900 includes a circuitry block 2920 that includes circuitry for selecting one or more nutraceutical agents responsive to the circuitry for receiving the one or more signals transmitted in response to intaking the information linked to the one or more parameters associated with the one or more specified goals of the individual. In some embodiments, the circuitry may be used for selecting one or more nutraceutical agents 118 responsive to the circuitry for receiving one or more signals 130 transmitted in response to intaking information 112 linked to one or more parameters 114 associated with one or more specified goals 106 of the individual 108.

In some embodiments, the circuitry may be used for selecting one or more nutraceutical agents 118 in response to circuitry for receiving one or more signals 130 transmitted in response to intaking information 112 linked to one or more parameters 114 associated with one or more specified goals 106 of the individual 108. In some embodiments, circuitry may be used for selecting one or more nutraceutical agents 118 in response to circuitry for accepting. In some embodiments, the circuitry may be used for selecting one or more nutraceutical agents 118 in response to circuitry for intaking units 110 and circuitry for accepting. Accordingly, in some embodiments, circuitry may be used for selecting one or more nutraceutical agents 118 with regard to one or more characteristics of the individual 108 and one or more parameters 114 associated with one or more specified goals 106 of the individual 108. For example, in some embodiments, circuitry may be used for selecting one or more nutraceutical agents 118 based on the age of the individual 108 and the level of testosterone in the individual's 108 blood. In other embodiments, circuitry may be used for selecting one or more nutraceutical agents 118 based on insurance coverage held by an individual 108 and a specified goal 106 of the individual 108.

After a start operation, the system 2900 includes a circuitry block 2930 that includes circuitry for indicating one or more dosages of the one or more nutraceutical agents responsive to the circuitry for selecting the one or more nutraceutical agents responsive to the circuitry for receiving the one or more signals transmitted in response to intaking the information linked to the one or more parameters associated with the one or more specified goals of the individual. In some embodiments, the circuitry may be used for indicating one or more dosages 122 of the one or more nutraceutical agents 118 responsive to the circuitry for selecting one or more nutraceutical agents 118 responsive to the circuitry for receiving one or more signals 130 transmitted in response to intaking information 112 linked to one or more parameters 114 associated with one or more specified goals 106 of the individual 108.

In some embodiments, the circuitry may be used for indicating one or more dosages 122 of one or more nutraceutical agents 118 in human-readable format. In some embodiments, the circuitry may be used for indicating one or more dosages 122 of one or more nutraceutical agents 118 in machine-readable format. In some embodiments, the circuitry may be used for indicating one or more dosages 122 of one or more nutraceutical agents 118 on one or more labels. In some embodiments, the circuitry may be used for dispensing one or more nutraceutical agents 118. In some embodiments, the circuitry may be used for dispensing one or more nutraceutical agents 118 in unit dosage form. In some embodiments, the circuitry may be used for dispensing two or more of one or more nutraceutical agents 118 in a single administration form.

Figure 30:
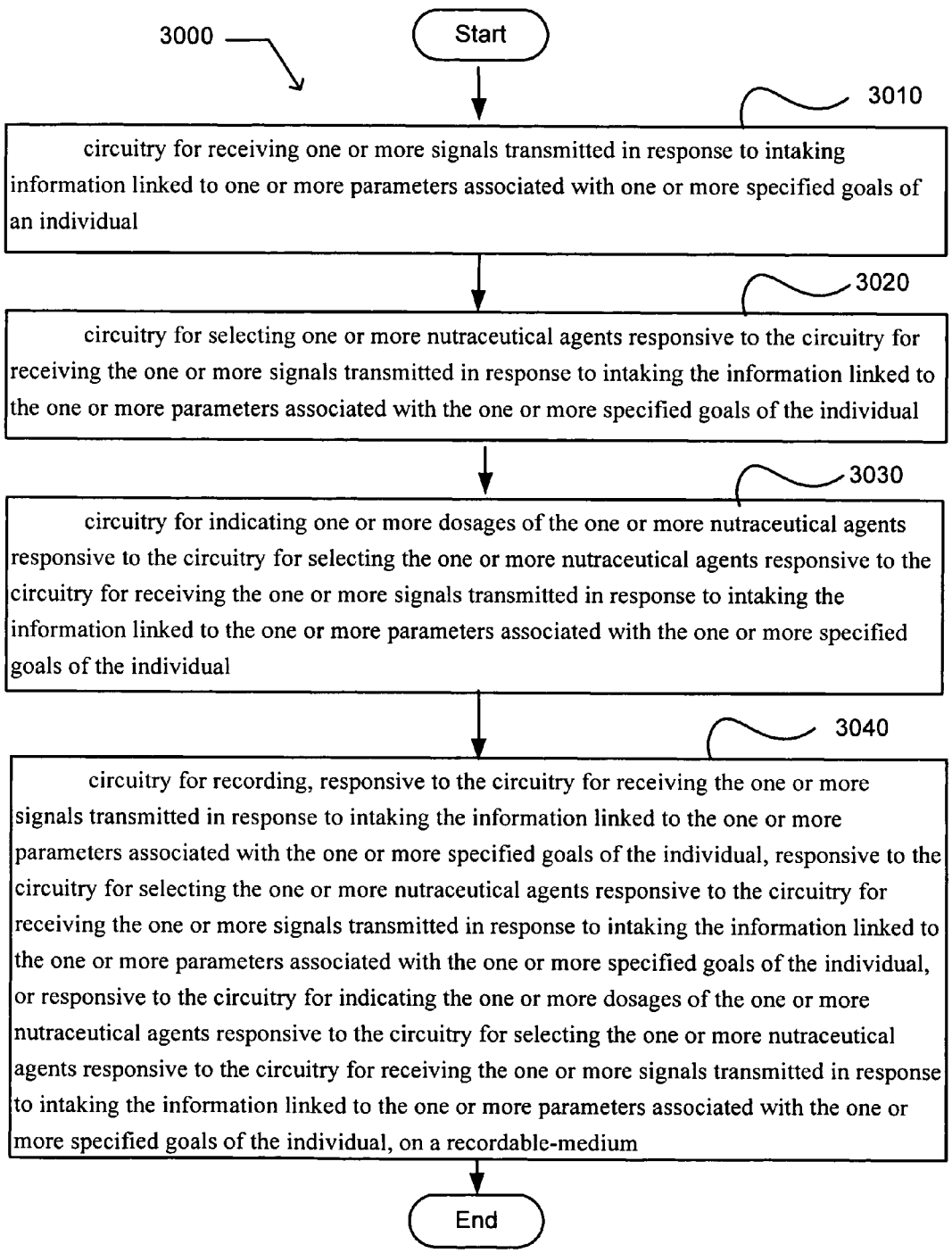
FIG. 30 illustrates an example system 3000 in which embodiments may be implemented.

FIG. 30 illustrates a system 3000 representing examples of circuitry that is related to systems for nutraceutical agent 118 and dosing. In FIG. 30 discussion and explanation may be provided with respect to the above-described example of FIG. 1, and/or with respect to other examples and contexts. However, it should be understood that the circuitry may be assembled in a number of other environments and contexts, and/or modified versions of FIG. 1. Also, although various circuitry is presented in the sequence(s) illustrated, it should be understood that circuitry may be assembled in other configurations than those which are illustrated.

After a start operation, the operational flow 3000 includes circuitry blocks 3010, 3020, and 3030 (which correspond to circuitry blocks 2910, 2920, and 2930 as described with regard to FIG. 29) and an additional circuitry block 3040 involving circuitry for recording, responsive to the circuitry for receiving the one or more signals transmitted in response to intaking the information linked to the one or more parameters associated with the one or more specified goals of the individual, responsive to the circuitry for selecting the one or more nutraceutical agents responsive to the circuitry for receiving the one or more signals transmitted in response to intaking the information linked to the one or more parameters associated with the one or more specified goals of the individual, or responsive to the circuitry for indicating the one or more dosages of the one or more nutraceutical agents responsive to the circuitry for selecting the one or more nutraceutical agents responsive to the circuitry for receiving the one or more signals transmitted in response to intaking the information linked to the one or more parameters associated with the one or more specified goals of the individual, on a recordable-medium. In some embodiments, the circuitry may be used for recording, responsive to circuitry for receiving one or more signals 130 transmitted in response to intaking information 112 linked to one or more parameters 114 associated with one or more specified goals 106 of the individual 108, responsive to the circuitry for selecting one or more nutraceutical agents 118 responsive to the circuitry for receiving one or more signals 130 transmitted in response to intaking information 112 linked to one or more parameters 114 associated with one or more specified goals 106 of the individual 108, or responsive to the circuitry for indicating one or more dosages 122 of the one or more nutraceutical agents 118 responsive to the circuitry for selecting one or more nutraceutical agents 118 responsive to the circuitry for receiving one or more signals 130 transmitted in response to intaking information 112 linked to one or more parameters 114 associated with one or more specified goals 106 of the individual 108, on a recordable-medium 126.

Figure 31:
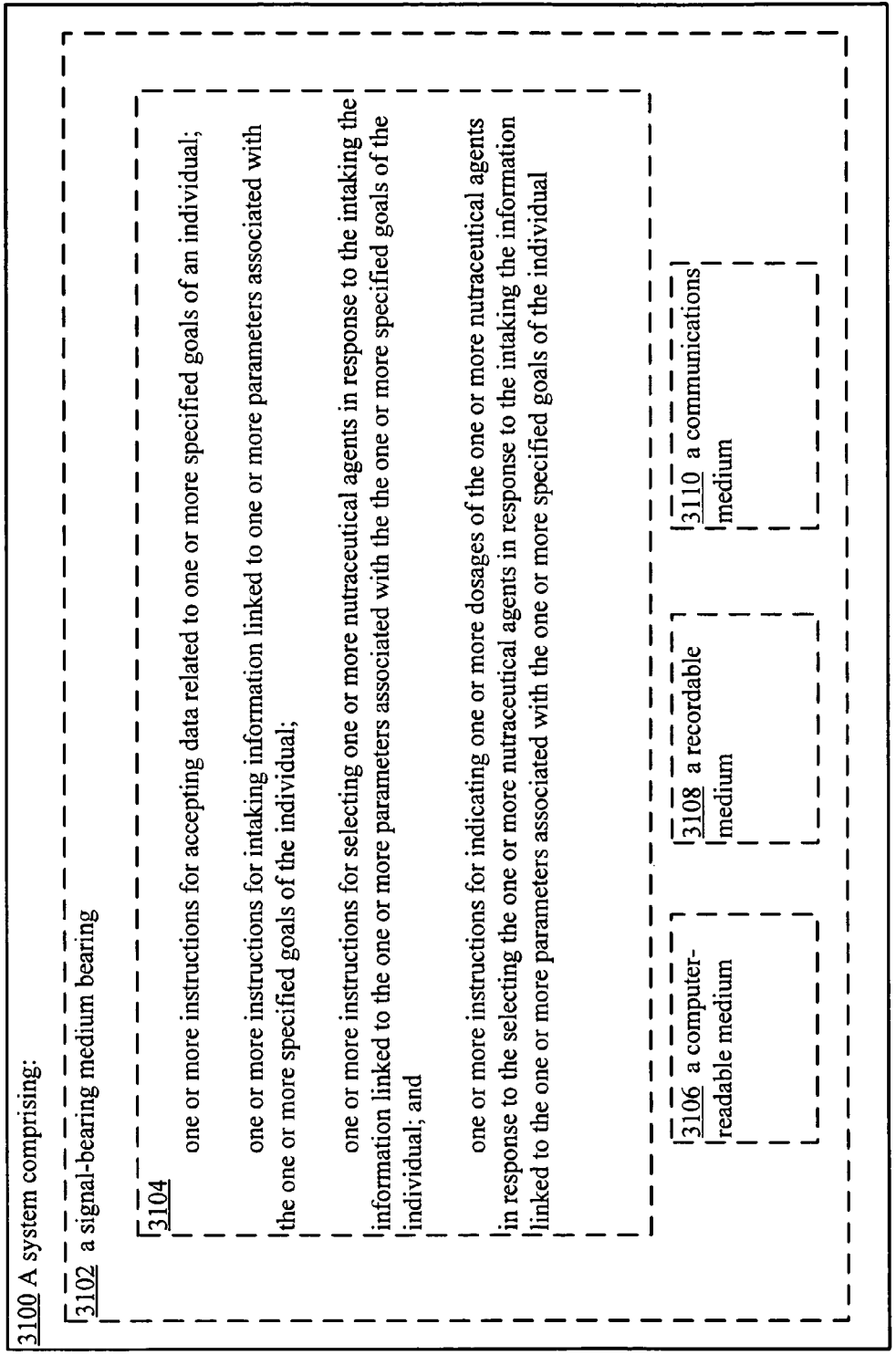
FIG. 31 illustrates an example system 3100 in which embodiments may be implemented.

FIG. 31 illustrates a partial view of a system 3100 that includes a computer program 3104 for executing a computer process on a computing device. An embodiment of the system 3100 is provided using a signal-bearing medium bearing, one or more instructions for accepting data related to one or more specified goals of an individual, one or more instructions for intaking information linked to one or more parameters associated with the one or more specified goals of the individual, one or more instructions for selecting one or more nutraceutical agents in response to the intaking the information linked to the one or more parameters associated with the one or more specified goals of the individual, and one or more instructions for indicating one or more dosages of the one or more nutraceutical agents in response to the selecting the one or more nutraceutical agents in response to the intaking the information linked to the one or more parameters associated with the one or more specified goals of the individual.

The one or more instructions may be, for example, computer executable and/or logic-implemented instructions. In some embodiments, the signal-bearing medium 3102 may include a computer-readable medium 3106. In some embodiments, the signal-bearing medium 3102 may include a recordable medium 3208. In some embodiments, the signal-bearing medium 3102 may include a communications medium 3110.

Figure 32:
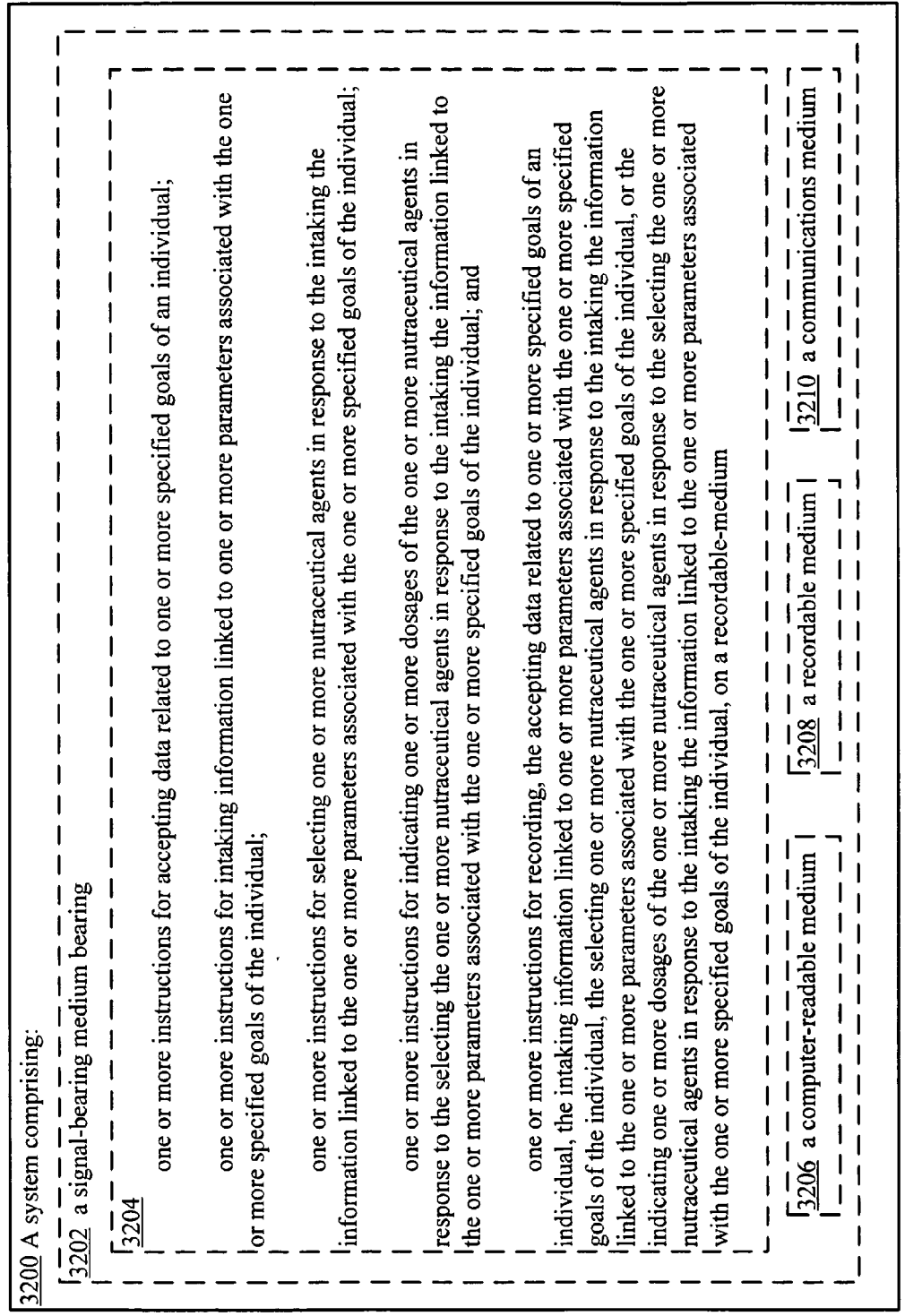
FIG. 32 illustrates an example system 3200 in which embodiments may be implemented.

FIG. 32 illustrates a partial view of a system 3100 that includes a computer program 3204 for executing a computer process on a computing device. An embodiment of the system 3200 is provided using a signal-bearing medium bearing, one or more instructions for accepting data related to one or more specified goals of an individual, one or more instructions for intaking information linked to one or more parameters associated with the one or more specified goals of the individual, one or more instructions for selecting one or more nutraceutical agents in response to the intaking the information linked to the one or more parameters associated with the one or more specified goals of the individual, one or more instructions for indicating one or more dosages of the one or more nutraceutical agents in response to the selecting the one or more nutraceutical agents in response to the intaking the information linked to the one or more parameters associated with the one or more specified goals of the individual, and one or more instructions for recording, the accepting data related to one or more specified goals of an individual, the intaking information linked to one or more parameters associated with the one or more specified goals of the individual, the selecting one or more nutraceutical agents in response to the intaking the information linked to the one or more parameters associated with the one or more specified goals of the individual, or the indicating one or more dosages of the one or more nutraceutical agents in response to the selecting the one or more nutraceutical agents in response to the intaking the information linked to the one or more parameters associated with the one or more specified goals of the individual, on a recordable-medium.

The one or more instructions may be, for example, computer executable and/or logic-implemented instructions. In some embodiments, the signal-bearing medium 3202 may include a computer-readable medium 3206. In some embodiments, the signal-bearing medium 3202 may include a recordable medium 3208. In some embodiments, the signal-bearing medium 3202 may include a communications medium 3210.

Figure 33:
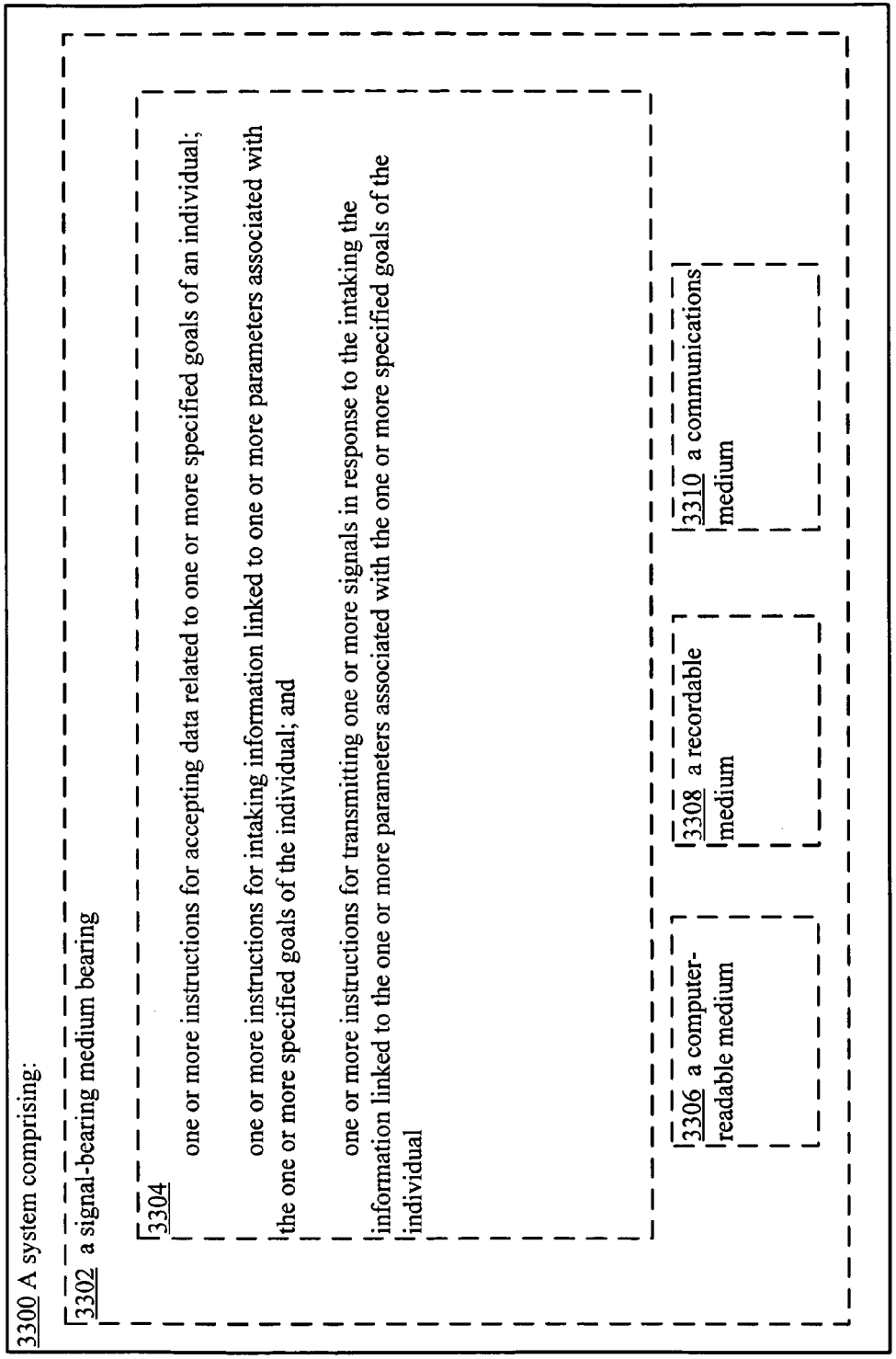
FIG. 33 illustrates an example system 3300 in which embodiments may be implemented.

FIG. 33 illustrates a partial view of a system 3300 that includes a computer program 3304 for executing a computer process on a computing device. An embodiment of the system 3300 is provided using a signal-bearing medium bearing, one or more instructions for accepting data related to one or more specified goals of an individual, one or more instructions for intaking information linked to one or more parameters associated with the one or more specified goals of the individual, and one or more instructions for transmitting one or more signals in response to the intaking the information linked to the one or more parameters associated with the one or more specified goals of the individual.

The one or more instructions may be, for example, computer executable and/or logic-implemented instructions. In some embodiments, the signal-bearing medium 3302 may include a computer-readable medium 3306. In some embodiments, the signal-bearing medium 3302 may include a recordable medium 3308. In some embodiments, the signal-bearing medium 3302 may include a communications medium 3310.

Figure 34:
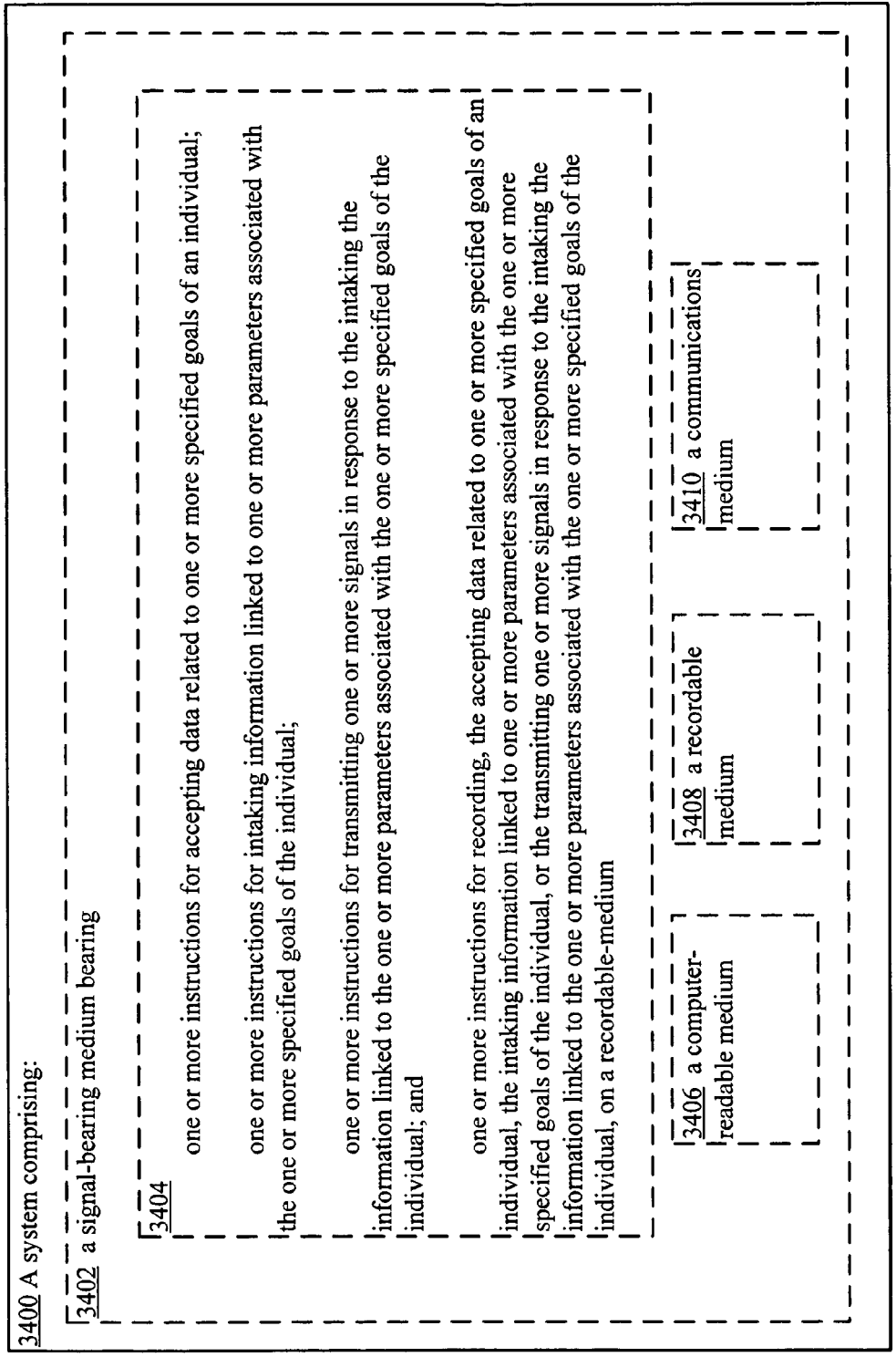
FIG. 34 illustrates an example system 3400 in which embodiments may be implemented.

FIG. 34 illustrates a partial view of a system 3400 that includes a computer program 3404 for executing a computer process on a computing device. An embodiment of the system 3400 is provided using a signal-bearing medium bearing, one or more instructions for accepting data related to one or more specified goals of an individual, one or more instructions for intaking information linked to one or more parameters associated with the one or more specified goals of the individual, one or more instructions for transmitting one or more signals in response to the intaking the information linked to the one or more parameters associated with the one or more specified goals of the individual, and one or more instructions for recording, the accepting data related to one or more specified goals of an individual, the intaking information linked to one or more parameters associated with the one or more specified goals of the individual, or the transmitting one or more signals in response to the intaking the information linked to the one or more parameters associated with the one or more specified goals of the individual, on a recordable-medium.

The one or more instructions may be, for example, computer executable and/or logic-implemented instructions. In some embodiments, the signal-bearing medium 3402 may include a computer-readable medium 3406. In some embodiments, the signal-bearing medium 3402 may include a recordable medium 3408. In some embodiments, the signal-bearing medium 3402 may include a communications medium 3410.

Figure 35:
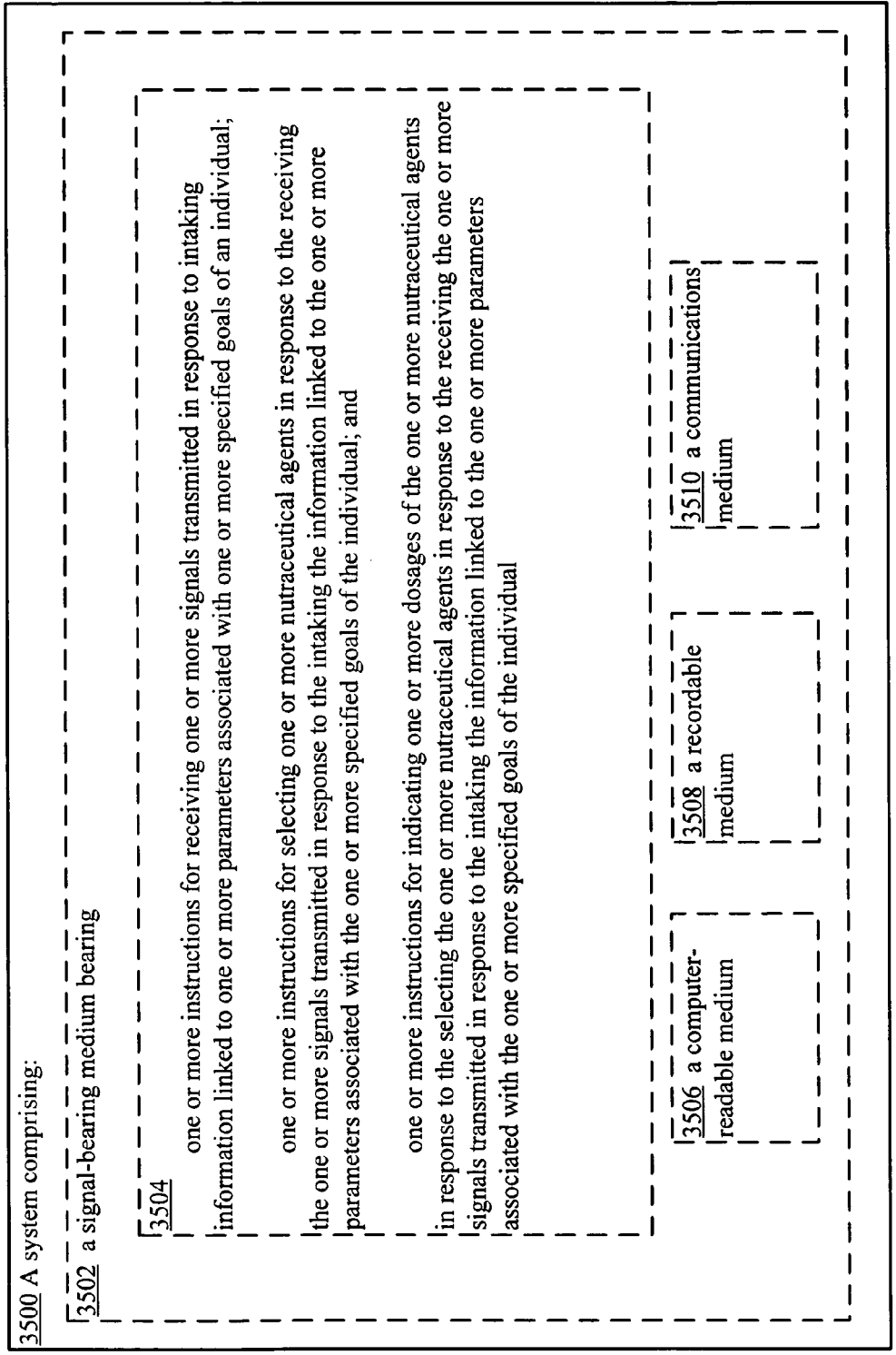
FIG. 35 illustrates an example system 3500 in which embodiments may be implemented.

FIG. 35 illustrates a partial view of a system 3500 that includes a computer program 3504 for executing a computer process on a computing device. An embodiment of the system 3500 is provided using a signal-bearing medium bearing, one or more instructions for receiving one or more signals transmitted in response to intaking information linked to one or more parameters associated with one or more specified goals of an individual, one or more instructions for selecting one or more nutraceutical agents in response to the receiving the one or more signals transmitted in response to the intaking the information linked to the one or more parameters associated with the one or more specified goals of the individual, and one or more instructions for indicating one or more dosages of the one or more nutraceutical agents in response to the selecting the one or more nutraceutical agents in response to the receiving the one or more signals transmitted in response to the intaking the information linked to the one or more parameters associated with the one or more specified goals of the individual.

The one or more instructions may be, for example, computer executable and/or logic-implemented instructions. In some embodiments, the signal-bearing medium 3502 may include a computer-readable medium 3506. In some embodiments, the signal-bearing medium 3502 may include a recordable medium 3508. In some embodiments, the signal-bearing medium 3502 may include a communications medium 3510.

Figure 36:
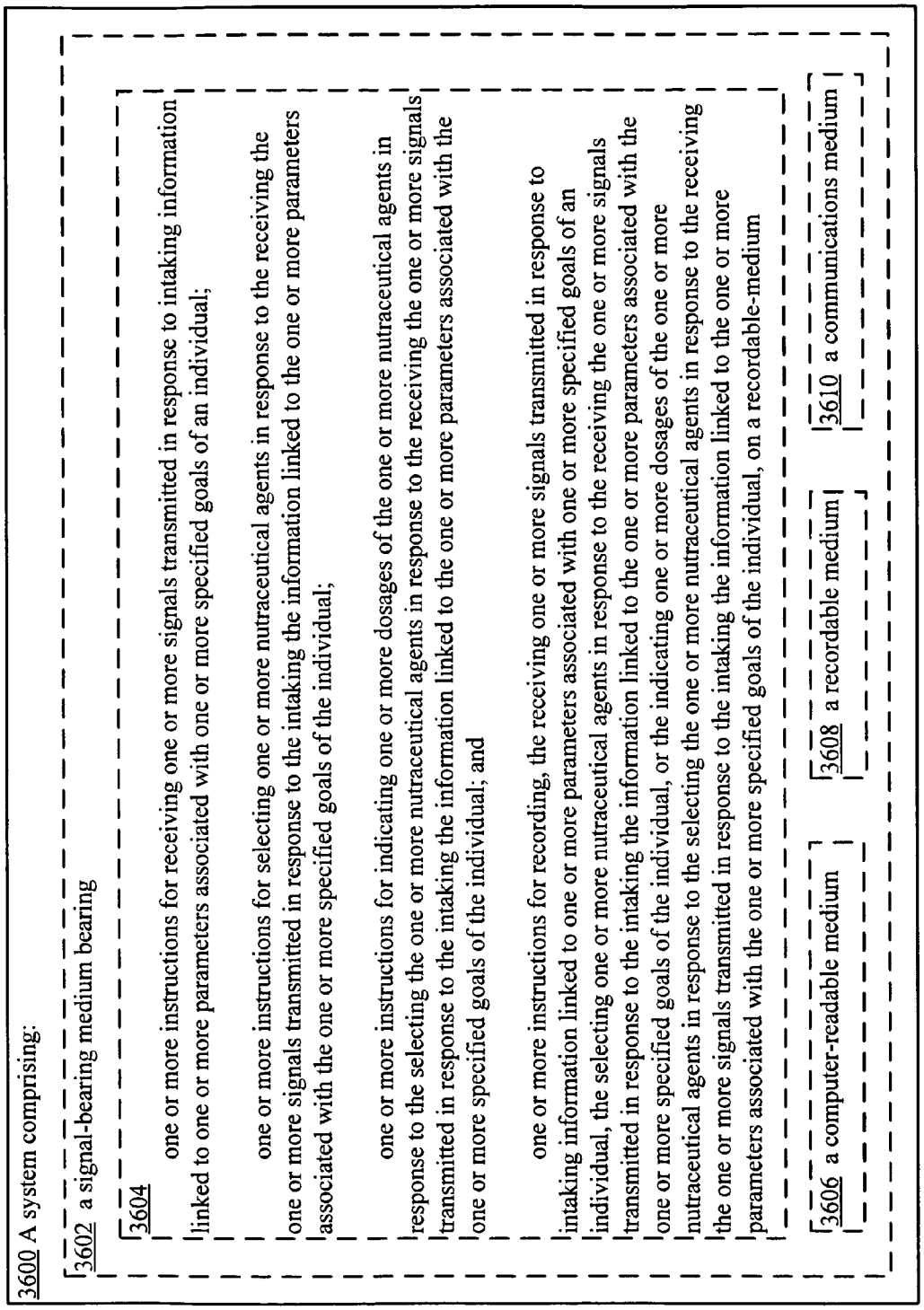
FIG. 36 illustrates an example system 3600 in which embodiments may be implemented.

FIG. 36 illustrates a partial view of a system 3600 that includes a computer program 3604 for executing a computer process on a computing device. An embodiment of the system 3600 is provided using a signal-bearing medium bearing, one or more instructions for receiving one or more signals transmitted in response to intaking information linked to one or more parameters associated with one or more specified goals of an individual, one or more instructions for selecting one or more nutraceutical agents in response to the receiving the one or more signals transmitted in response to the intaking the information linked to the one or more parameters associated with the one or more specified goals of the individual, one or more instructions for indicating one or more dosages of the one or more nutraceutical agents in response to the selecting the one or more nutraceutical agents in response to the receiving the one or more signals transmitted in response to the intaking the information linked to the one or more parameters associated with the one or more specified goals of the individual, and one or more instructions for recording, the receiving one or more signals transmitted in response to intaking information linked to one or more parameters associated with one or more specified goals of an individual, the selecting one or more nutraceutical agents in response to the receiving the one or more signals transmitted in response to the intaking the information linked to the one or more parameters associated with the one or more specified goals of the individual, or the indicating one or more dosages of the one or more nutraceutical agents in response to the selecting the one or more nutraceutical agents in response to the receiving the one or more signals transmitted in response to the intaking the information linked to the one or more parameters associated with the one or more specified goals of the individual, on a recordable-medium.

The one or more instructions may be, for example, computer executable and/or logic-implemented instructions. In some embodiments, the signal-bearing medium 3602 may include a computer-readable medium 3606. In some embodiments, the signal-bearing medium 3602 may include a recordable medium 3608. In some embodiments, the signal-bearing medium 3602 may include a communications medium 3610.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity (e.g., such as Sprint, Cingular, Nextel, etc.), etc.

Although user 136 is shown/described herein as a single illustrated figure, those skilled in the art will appreciate that a user 136 may be representative of a human user 136, a robotic user 136 (e.g., computational entity), and/or substantially any combination thereof (e.g., a user 136 may be assisted by one or more robotic agents). In addition, a user 136 as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A method comprising:
   receiving one or more signals that include information related to nutraceutical usage by one or more individuals;
   receiving one or more signals that include information related to one or more parameters associated with the one or more individuals; and
   processing, using one or more processors, the one or more signals that include information related to nutraceutical usage by the one or more individuals and the one or more signals that include information related to the one or more parameters associated with the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages.

2. The method of claim 1, further comprising:
   receiving one or more signals that include information related to one or more goals of the one or more individuals.

3. The method of claim 2, wherein the processing, using one or more processors, the one or more signals that include information related to nutraceutical usage by the one or more individuals and the one or more signals that include information related to the one or more parameters associated with the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages comprises:
   processing, using one or more processors, the one or more signals that include information related to nutraceutical usage by the one or more individuals and the one or more signals that include information related to the one or more parameters associated with the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships and/or the one or more goals of the one or more individuals one or more nutraceutical dosages or modification of one or more nutraceutical dosages.

4. The method of claim 1, wherein the receiving one or more signals that include information related to one or more parameters associated with the one or more individuals comprises:
   receiving one or more signals that include information related to one or more parameters determined from one or more assays of one or more bodily fluid, bodily tissue, and/or bodily product samples associated with the one or more individuals.

5. The method of claim 1, wherein the receiving one or more signals that include information related to one or more parameters associated with the one or more individuals comprises:
   receiving one or more signals that include information related to one or more levels of one or more metabolic indicators associated with the one or more individuals.

6. The method of claim 1, further comprising:
   indicating in human and/or machine readable format the one or more nutraceutical dosages or the modification of one or more nutraceutical dosages.

7. The method of claim 6, wherein the indicating in human and/or machine readable format the one or more nutraceutical dosages or the modification of one or more nutraceutical dosages comprises:
   indicating in human and/or machine readable format the one or more nutraceutical dosages or the modification of one or more nutraceutical dosages on one or more labels.

8. The method of claim 1, further comprising:
   dispensing the one or more nutraceutical dosages or the modification of one or more nutraceutical dosages.

9. The method of claim 1, wherein the receiving one or more signals that include information related to nutraceutical usage by one or more individuals comprises:
   receiving one or more signals that include information related to nutraceutical usage determined from one or more assays of one or more bodily fluid, bodily tissue, and/or bodily product samples associated with one or more individuals.

10. The method of claim 1, wherein the receiving one or more signals that include information related to nutraceutical usage by one or more individuals comprises:
    receiving one or more signals that include information related to pharmaceutical usage by one or more individuals.

11. The method of claim 1, wherein the receiving one or more signals that include information related to one or more parameters associated with the one or more individuals comprises:
    receiving one or more signals that include information related to one or more physical, mental, behavioral, environmental, goal, and/or nutritional parameters associated with the one or more individuals.

12. The method of claim 1, wherein the receiving one or more signals that include information related to one or more parameters associated with the one or more individuals comprises:

receiving one or more signals that include information related to one or more appearance and/or characteristic parameters associated with the one or more individuals.

13. The method of claim 1, wherein the processing, using one or more processors, the one or more signals that include information related to nutraceutical usage by the one or more individuals and the one or more signals that include information related to the one or more parameters associated with the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages comprises:

processing, using one or more processors, the one or more signals that include information related to nutraceutical usage by the one or more individuals and the one or more signals that include information related to the one or more parameters associated with the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, comparing the one or more relationships with one or more relationships determined for one or more different individuals, and determining based upon the one or more relationships and/or the one or more relationships determined for one or more different individuals one or more nutraceutical dosages or modification of one or more nutraceutical dosages.

14. The method of claim 1, further comprising:

transmitting to one or more food supplement stores and/or grocery stores the one or more nutraceutical dosages or the modification of one or more nutraceutical dosages.

15. A method comprising:

receiving one or more signals that include information related to nutraceutical usage by one or more individuals;

receiving one or more signals that include information related to one or more parameters associated with the one or more individuals; and transmitting, using one or more transmitters, the one or more signals that include information related to nutraceutical usage by the one or more individuals and the one or more signals that include information related to the one or more parameters associated with the one or more individuals for comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages.

16. The method of claim 15, further comprising:

receiving one or more signals that include information related to one or more goals of the one or more individuals.

17. The method of claim 16, wherein the transmitting, using one or more transmitters, the one or more signals that include information related to nutraceutical usage by the one or more individuals and the one or more signals that include information related to the one or more parameters associated with the one or more individuals for comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages comprises:

transmitting, using one or more transmitters, the one or more signals that include information related to nutraceutical usage by the one or more individuals and the one or more signals that include information related to the one or more parameters associated with the one or more individuals for comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships and/or the one or more goals of the one or more individuals one or more nutraceutical dosages or modification of one or more nutraceutical dosages.

18. The method of claim 15, wherein the receiving one or more signals that include information related to one or more parameters associated with the one or more individuals comprises:

receiving one or more signals that include information related to one or more parameters determined from one or more assays of one or more bodily fluid, bodily tissue, and/or bodily product samples associated with the one or more individuals.

19. The method of claim 15, wherein the receiving one or more signals that include information related to one or more parameters associated with the one or more individuals comprises:

receiving one or more signals that include information related to one or more levels of one or more metabolic indicators associated with the one or more individuals.

20. The method of claim 15, further comprising:

receiving one or more signals that include information related to the one or more nutraceutical dosages or the modification of one or more nutraceutical dosages.

21. The method of claim 15, wherein the transmitting, using one or more transmitters, the one or more signals that include information related to nutraceutical usage by the one or more individuals and the one or more signals that include information related to the one or more parameters associated with the one or more individuals for comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages comprises:

transmitting, using one or more transmitters, the one or more signals that include information related to nutraceutical usage by the one or more individuals and the one or more signals that include information related to the one or more parameters associated with the one or more individuals for comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages that stimulate and/or inhibit one or more metabolic pathways associated with the one or more individuals.

22. A method comprising:

processing, using one or more processors, one or more signals that include information related to nutraceutical usage by one or more individuals and one or more signals that include information related to one or more parameters associated with the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages; and transmitting one or more signals that include information related to the one or more nutraceutical dosages or the modification of one or more nutraceutical dosages.

23. The method of claim 22, wherein the processing, using one or more processors, one or more signals that include information related to nutraceutical usage by one or more individuals and one or more signals that include information related to one or more parameters associated with the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages comprises:

processing, using one or more processors, one or more signals that include information related to nutraceutical usage by one or more individuals and one or more signals that include information related to one or more levels of one or more metabolic indicators associated with the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages.

24. The method of claim 22, wherein the processing, using one or more processors, one or more signals that include information related to nutraceutical usage by one or more individuals and one or more signals that include information related to one or more parameters associated with the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages comprises:

processing, using one or more processors, one or more signals that include information related to nutraceutical usage by one or more individuals, one or more signals that include information related to one or more parameters associated with the one or more individuals, and one or more signals that include information related to one or more goals of the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages.

25. The method of claim 22, wherein the processing, using one or more processors, one or more signals that include information related to nutraceutical usage by one or more individuals and one or more signals that include information related to one or more parameters associated with the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages comprises:

processing, using one or more processors, one or more signals that include information related to nutraceutical usage by one or more individuals and one or more signals that include information related to one or more parameters associated with the one or more individuals, including comparing from two or more different times one or more values associated with the one or more parameters, determining one or more changes in the one or more values associated with the one or more parameters, identifying based upon the one or more changes one or more relationships between the one or more parameters and the nutraceutical usage, and determining based upon the one or more relationships one or more nutraceutical dosages or modification of one or more nutraceutical dosages that stimulate and/or inhibit one or more metabolic pathways associated with the one or more individuals.

26. The method of claim 22, further comprising:
indicating in human and/or machine readable format the one or more nutraceutical dosages or the modification of one or more nutraceutical dosages.

27. The method of claim 22, further comprising:
depositing the one or more nutraceutical dosages or the modification of one or more nutraceutical dosages on one or more labels.

28. The method of claim 22, further comprising:
dispensing the one or more nutraceutical dosages or the modification of one or more nutraceutical dosages.

* * * * *